United States Patent
Lehr et al.

(10) Patent No.: US 10,383,950 B2
(45) Date of Patent: Aug. 20, 2019

(54) METHODS AND COMPOSITIONS OF CARRIER SYSTEMS FOR THE PURPOSE OF INTRACELLULAR DRUG TARGETING

(71) Applicant: HELMHOLTZ-ZENTRUM FÜR INFEKTIONSFORSCHUNG GMBH, Braunschweig (DE)

(72) Inventors: Claus-Michael Lehr, Saarbrücken-Dudweiler (DE); Hagar Ibrahim Labouta, Calgary (CA); Sarah Gordon, Saarbrücken (DE); Arianna Castoldi, Saarbrücken (DE); Sara Menina, Homburg Saar (DE); Rebecca Geyer, Braunschweig (DE); Annika Kochut, Braunschweig (DE); Petra Dersch, Hannover (DE)

(73) Assignee: HELMHOLTZ-ZENTRUM FUR INFEKTIONSFORSCHUNG GMBH (DE/DE), Braunschweig (DE)

( * ) Notice: Subject to any disclaimer, the term of this patent is extended or adjusted under 35 U.S.C. 154(b) by 79 days.

(21) Appl. No.: 15/503,010

(22) PCT Filed: Aug. 14, 2015

(86) PCT No.: PCT/EP2015/068722
§ 371 (c)(1),
(2) Date: Feb. 10, 2017

(87) PCT Pub. No.: WO2016/024008
PCT Pub. Date: Feb. 18, 2016

(65) Prior Publication Data
US 2017/0232114 A1  Aug. 17, 2017

(30) Foreign Application Priority Data

Aug. 14, 2014  (WO) ................. PCT/EP2014/067459
Sep. 22, 2014  (EP) ..................................... 14185838

(51) Int. Cl.
A61K 9/127  (2006.01)
A61K 47/69  (2017.01)

(52) U.S. Cl.
CPC ........ *A61K 47/6911* (2017.08); *A61K 9/1271* (2013.01); *Y02A 50/402* (2018.01); *Y02A 50/475* (2018.01); *Y02A 50/478* (2018.01); *Y02A 50/481* (2018.01)

(58) Field of Classification Search
None
See application file for complete search history.

(56) References Cited

U.S. PATENT DOCUMENTS

2014/0010824 A1* 1/2014 Mecsas .............. G01N 33/5005
424/164.1

FOREIGN PATENT DOCUMENTS

WO   WO96/13250   5/1996

OTHER PUBLICATIONS

Dawson et al. The in vitro cell association of Invasin Coated polylactide-Co-Glycolide Nanoparticles: Pharmaceutical Research, vol. 17. No. 11, 2000.
Hussain et al. Utilizing bacterial mechanisms of Epithelial cell Entry: Invasin induced Oral uptake of Latex Nanoparticles: Pharmaceutical Research, vol. 15, No. 1, 1998.

* cited by examiner

*Primary Examiner* — Jana A Hines
*Assistant Examiner* — Khatol S Shahnan Shah
(74) *Attorney, Agent, or Firm* — IP Aid LLC; Yonghao Hou

(57) ABSTRACT

The present invention relates to a carrier system, a carrier and a pharmaceutical composition comprising a pathogen entry protein or fragment thereof, which specifically binds to a molecule on the surface of a mammalian target cell of said pathogen and which is covalently linked to the surface of said carrier and at least one hydrophilic antipathogenic agent. It further relates to a method of manufacturing a carrier system and the carrier system or the pharmaceutical composition for the use as a medicament.

27 Claims, 18 Drawing Sheets

Specification includes a Sequence Listing.

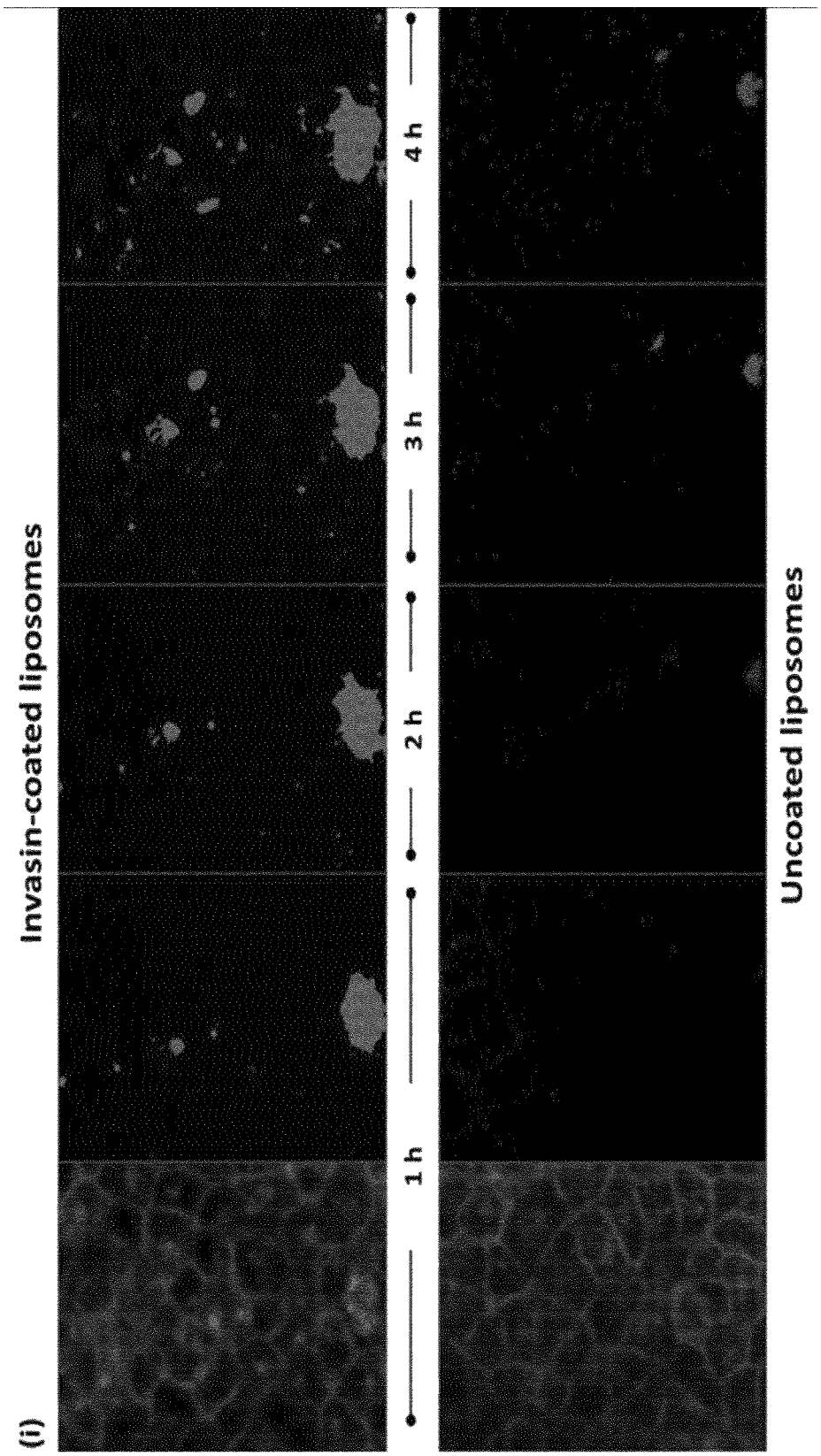

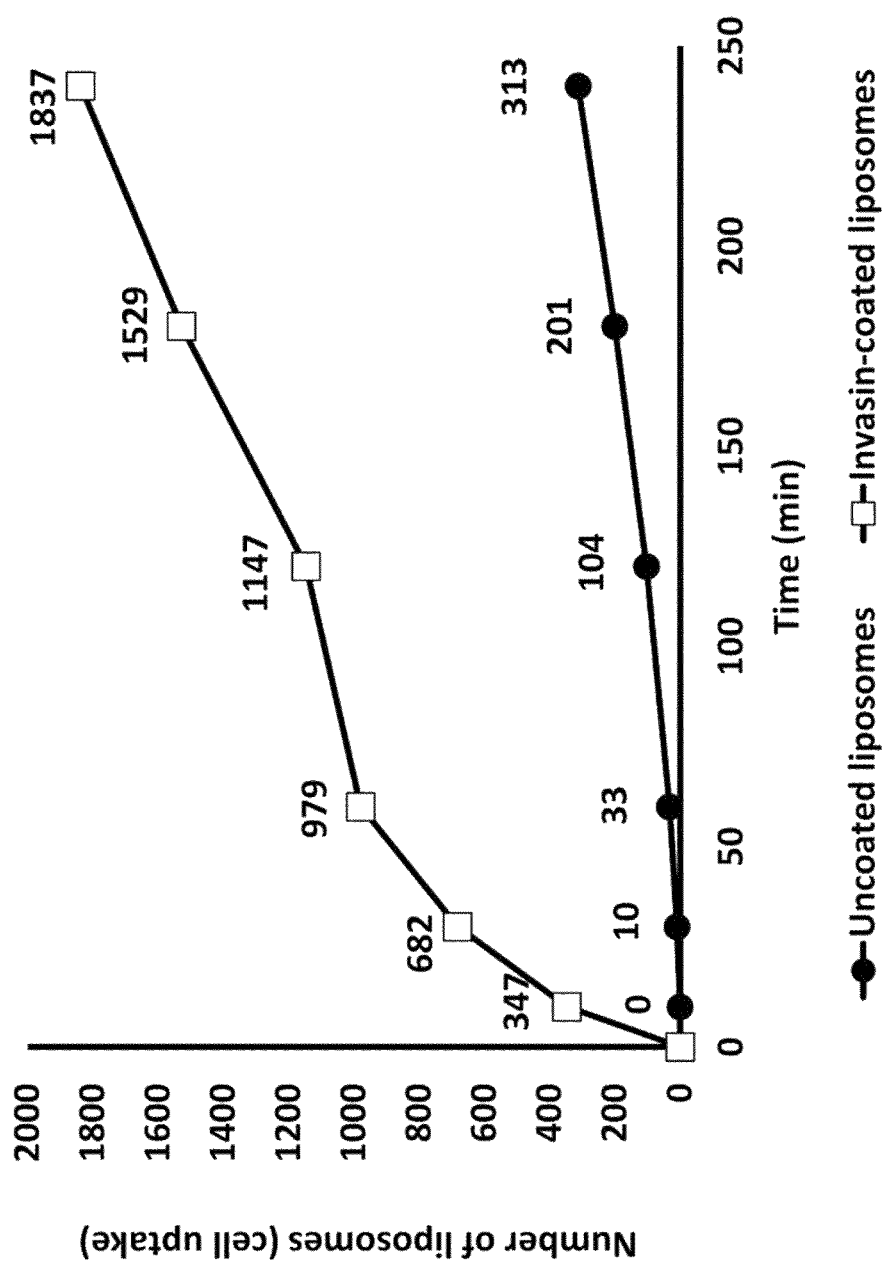
Figure 4 ii)

Figure 12
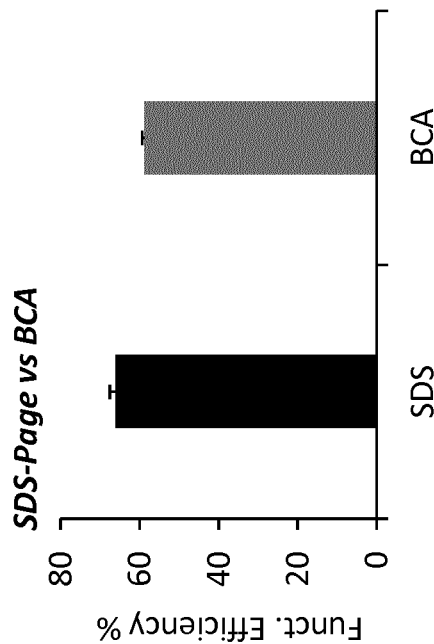
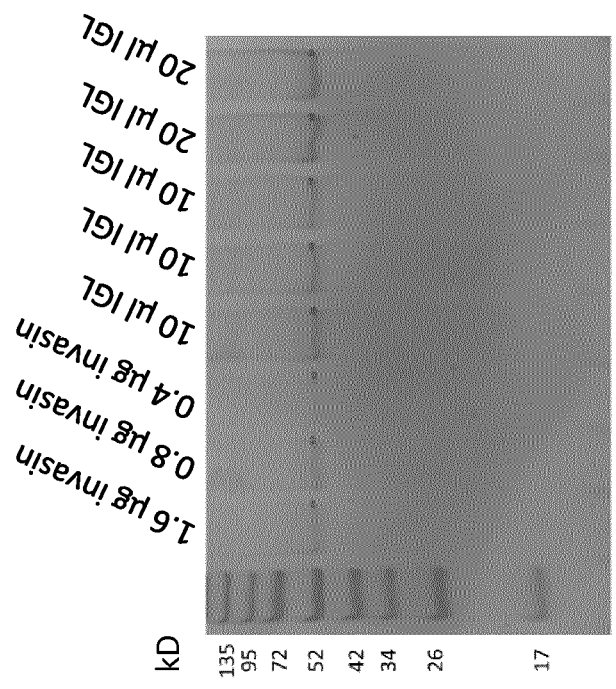

SEQUENCE LISTING

```
<160> NUMBER OF SEQ ID NOS: 9

<210> SEQ ID NO 1
<211> LENGTH: 969
<212> TYPE: PRT
<213> ORGANISM: Yersinia pseudotuberculosis
<220> FEATURE:
<221> NAME/KEY: InvA YPK_2429
<222> LOCATION: (1)..(969)

<400> SEQUENCE: 1

Met Ser Met Tyr Phe Asn Lys Ile Ile Ser Phe Asn Ile Ile Ser Arg
1               5                   10                  15
```

```
Ile Val Ile Cys Ile Phe Leu Ile Cys Gly Met Phe Met Ala Gly Ala
                20                  25                  30

Ser Glu Lys Tyr Asp Ala Asn Ala Pro Gln Gln Val Gln Pro Tyr Ser
            35                  40                  45

Val Ser Ser Ser Ala Phe Glu Asn Leu His Pro Asn Asn Glu Met Glu
    50                  55                  60

Ser Ser Ile Asn Pro Phe Ser Ala Ser Asp Thr Glu Arg Asn Ala Ala
65                  70                  75                  80

Ile Ile Asp Arg Ala Asn Lys Glu Gln Glu Thr Glu Ala Val Asn Lys
                85                  90                  95

Met Ile Ser Thr Gly Ala Arg Leu Ala Ala Ser Gly Arg Ala Ser Asp
            100                 105                 110

Val Ala His Ser Met Val Gly Asp Ala Val Asn Gln Glu Ile Lys Gln
    115                 120                 125

Trp Leu Asn Arg Phe Gly Thr Ala Gln Val Asn Leu Asn Phe Asp Lys
    130                 135                 140

Asn Phe Ser Leu Lys Glu Ser Ser Leu Asp Trp Leu Ala Pro Trp Tyr
145                 150                 155                 160

Asp Ser Ala Ser Phe Leu Phe Phe Ser Gln Leu Gly Ile Arg Asn Lys
                165                 170                 175

Asp Ser Arg Asn Thr Leu Asn Leu Gly Val Gly Ile Arg Thr Leu Glu
            180                 185                 190

Asn Gly Trp Leu Tyr Gly Leu Asn Thr Phe Tyr Asp Asn Asp Leu Thr
    195                 200                 205

Gly His Asn His Arg Ile Gly Leu Gly Ala Glu Ala Trp Thr Asp Tyr
    210                 215                 220

Leu Gln Leu Ala Ala Asn Gly Tyr Phe Arg Leu Asn Gly Trp His Ser
225                 230                 235                 240

Ser Arg Asp Phe Ser Asp Tyr Lys Glu Arg Pro Ala Thr Gly Gly Asp
                245                 250                 255

Leu Arg Ala Asn Ala Tyr Leu Pro Ala Leu Pro Gln Leu Gly Gly Lys
            260                 265                 270

Leu Met Tyr Glu Gln Tyr Thr Gly Glu Arg Val Ala Leu Phe Gly Lys
    275                 280                 285

Asp Asn Leu Gln Arg Asn Pro Tyr Ala Val Thr Ala Gly Ile Asn Tyr
    290                 295                 300

Thr Pro Val Pro Leu Leu Thr Val Gly Val Asp Gln Arg Met Gly Lys
305                 310                 315                 320

Ser Ser Lys His Glu Thr Gln Trp Asn Leu Gln Met Asn Tyr Arg Leu
                325                 330                 335

Gly Glu Ser Phe Gln Ser Gln Leu Ser Pro Ser Ala Val Ala Gly Thr
            340                 345                 350

Arg Leu Leu Ala Glu Ser Arg Tyr Asn Leu Val Asp Arg Asn Asn Asn
    355                 360                 365

Ile Val Leu Glu Tyr Gln Lys Gln Gln Val Val Lys Leu Thr Leu Ser
    370                 375                 380

Pro Ala Thr Ile Ser Gly Leu Pro Gly Gln Val Tyr Gln Val Asn Ala
385                 390                 395                 400

Gln Val Gln Gly Ala Ser Ala Val Arg Glu Ile Val Trp Ser Asp Ala
                405                 410                 415

Glu Leu Ile Ala Ala Gly Gly Thr Leu Thr Pro Leu Ser Thr Thr Gln
            420                 425                 430

Phe Asn Leu Val Leu Pro Pro Tyr Lys Arg Thr Ala Gln Val Ser Arg
```

-continued

```
                435                 440                 445
Val Thr Asp Asp Leu Thr Ala Asn Phe Tyr Ser Leu Ser Ala Leu Ala
450                 455                 460

Val Asp His Gln Gly Asn Arg Ser Asn Ser Phe Thr Leu Ser Val Thr
465             470                  475                 480

Val Gln Gln Pro Gln Leu Thr Leu Thr Ala Val Ile Gly Asp Gly
                485                 490                 495

Ala Pro Ala Asn Gly Lys Thr Ala Ile Thr Val Glu Phe Thr Val Ala
            500                  505                 510

Asp Phe Glu Gly Lys Pro Leu Ala Gly Gln Glu Val Val Ile Thr Thr
                515                 520                 525

Asn Asn Gly Ala Leu Pro Asn Lys Ile Thr Glu Lys Thr Asp Ala Asn
530                 535                 540

Gly Val Ala Arg Ile Ala Leu Thr Asn Thr Thr Asp Gly Val Thr Val
545                 550                 555                 560

Val Thr Ala Glu Val Glu Gly Gln Arg Gln Ser Val Asp Thr His Phe
                565                 570                 575

Val Lys Gly Thr Ile Ala Ala Asp Lys Ser Thr Leu Ala Ala Val Pro
            580                 585                 590

Thr Ser Ile Ile Ala Asp Gly Leu Met Ala Ser Thr Ile Thr Leu Glu
                595                 600                 605

Leu Lys Asp Thr Tyr Gly Asp Pro Gln Ala Gly Ala Asn Val Ala Phe
610                 615                 620

Asp Thr Thr Leu Gly Asn Met Gly Val Ile Thr Asp His Asn Asp Gly
625                 630                 635                 640

Thr Tyr Ser Ala Pro Leu Thr Ser Thr Thr Leu Gly Val Ala Thr Val
                645                 650                 655

Thr Val Lys Val Asp Gly Ala Ala Phe Ser Val Pro Ser Val Thr Val
            660                 665                 670

Asn Phe Thr Ala Asp Pro Ile Pro Asp Ala Gly Arg Ser Ser Phe Thr
                675                 680                 685

Val Ser Thr Pro Asp Ile Leu Ala Asp Gly Thr Met Ser Ser Thr Leu
690                 695                 700

Ser Phe Val Pro Val Asp Lys Asn Gly His Phe Ile Ser Gly Met Gln
705                 710                 715                 720

Gly Leu Ser Phe Thr Gln Asn Gly Val Pro Val Ser Ile Ser Pro Ile
                725                 730                 735

Thr Glu Gln Pro Asp Ser Tyr Thr Ala Thr Val Val Gly Asn Ser Val
            740                 745                 750

Gly Asp Val Thr Ile Thr Pro Gln Val Asp Thr Leu Ile Leu Ser Thr
            755                 760                 765

Leu Gln Lys Lys Ile Ser Leu Phe Pro Val Pro Thr Leu Thr Gly Ile
            770                 775                 780

Leu Val Asn Gly Gln Asn Phe Ala Thr Asp Lys Gly Phe Pro Lys Thr
785                 790                 795                 800

Ile Phe Lys Asn Ala Thr Phe Gln Leu Gln Met Asp Asn Asp Val Ala
                805                 810                 815

Asn Asn Thr Gln Tyr Glu Trp Ser Ser Ser Phe Thr Pro Asn Val Ser
            820                 825                 830

Val Asn Asp Gln Gly Gln Val Thr Ile Thr Tyr Gln Thr Tyr Ser Glu
            835                 840                 845

Val Ala Val Thr Ala Lys Ser Lys Lys Phe Pro Ser Tyr Ser Val Ser
            850                 855                 860
```

```
Tyr Arg Phe Tyr Pro Asn Arg Trp Ile Tyr Asp Gly Gly Arg Ser Leu
865                 870                 875                 880

Val Ser Ser Leu Glu Ala Ser Arg Gln Cys Gln Gly Ser Asp Met Ser
                885                 890                 895

Ala Val Leu Glu Ser Ser Arg Ala Thr Asn Gly Thr Arg Ala Pro Asp
            900                 905                 910

Gly Thr Leu Trp Gly Glu Trp Gly Ser Leu Thr Ala Tyr Ser Ser Asp
            915                 920                 925

Trp Gln Ser Gly Glu Tyr Trp Val Lys Lys Thr Ser Thr Asp Phe Glu
        930                 935                 940

Thr Met Asn Met Asp Thr Gly Ala Leu Gln Pro Gly Pro Ala Tyr Leu
945                 950                 955                 960

Ala Phe Pro Leu Cys Ala Leu Ser Ile
                965

<210> SEQ ID NO 2
<211> LENGTH: 480
<212> TYPE: PRT
<213> ORGANISM: Yersinia pseudotuberculosis
<220> FEATURE:
<221> NAME/KEY: pAK01aa 490-987 for overexpression
<222> LOCATION: (1)..(480)

<400> SEQUENCE: 2

Ala Ala Val Ile Gly Asp Gly Ala Pro Ala Asn Gly Lys Thr Ala Ile
1               5                   10                  15

Thr Val Glu Phe Thr Val Ala Asp Phe Glu Gly Lys Pro Leu Ala Gly
            20                  25                  30

Gln Glu Val Val Ile Thr Thr Asn Asn Gly Ala Leu Pro Asn Lys Ile
        35                  40                  45

Thr Glu Lys Thr Asp Ala Asn Gly Val Ala Arg Ile Ala Leu Thr Asn
50                  55                  60

Thr Thr Asp Gly Val Thr Val Val Thr Ala Glu Val Glu Gly Gln Arg
65                  70                  75                  80

Gln Ser Val Asp Thr His Phe Val Lys Gly Thr Ile Ala Ala Asp Lys
                85                  90                  95

Ser Thr Leu Ala Ala Val Pro Thr Ser Ile Ile Ala Asp Gly Leu Met
            100                 105                 110

Ala Ser Thr Ile Thr Leu Glu Leu Lys Asp Thr Tyr Gly Asp Pro Gln
        115                 120                 125

Ala Gly Ala Asn Val Ala Phe Asp Thr Thr Leu Gly Asn Met Gly Val
    130                 135                 140

Ile Thr Asp His Asn Asp Gly Thr Tyr Ser Ala Pro Leu Thr Ser Thr
145                 150                 155                 160

Thr Leu Gly Val Ala Thr Val Thr Val Lys Val Asp Gly Ala Ala Phe
                165                 170                 175

Ser Val Pro Ser Val Thr Val Asn Phe Thr Ala Asp Pro Ile Pro Asp
            180                 185                 190

Ala Gly Arg Ser Ser Phe Thr Val Ser Thr Pro Asp Ile Leu Ala Asp
        195                 200                 205

Gly Thr Met Ser Ser Thr Leu Ser Phe Val Pro Val Asp Lys Asn Gly
    210                 215                 220

His Phe Ile Ser Gly Met Gln Gly Leu Ser Phe Thr Gln Asn Gly Val
225                 230                 235                 240

Pro Val Ser Ile Ser Pro Ile Thr Glu Gln Pro Asp Ser Tyr Thr Ala
```

```
            245                 250                 255
Thr Val Val Gly Asn Ser Val Gly Asp Val Thr Ile Thr Pro Gln Val
            260                 265                 270

Asp Thr Leu Ile Leu Ser Thr Leu Gln Lys Lys Ile Ser Leu Phe Pro
            275                 280                 285

Val Pro Thr Leu Thr Gly Ile Leu Val Asn Gly Gln Asn Phe Ala Thr
            290                 295                 300

Asp Lys Gly Phe Pro Lys Thr Ile Phe Lys Asn Ala Thr Phe Gln Leu
305                 310                 315                 320

Gln Met Asp Asn Asp Val Ala Asn Asn Thr Gln Tyr Glu Trp Ser Ser
            325                 330                 335

Ser Phe Thr Pro Asn Val Ser Val Asn Asp Gln Gly Gln Val Thr Ile
            340                 345                 350

Thr Tyr Gln Thr Tyr Ser Glu Val Ala Val Thr Ala Lys Ser Lys Lys
            355                 360                 365

Phe Pro Ser Tyr Ser Val Ser Tyr Arg Phe Tyr Pro Asn Arg Trp Ile
            370                 375                 380

Tyr Asp Gly Gly Arg Ser Leu Val Ser Ser Leu Glu Ala Ser Arg Gln
385                 390                 395                 400

Cys Gln Gly Ser Asp Met Ser Ala Val Leu Glu Ser Ser Arg Ala Thr
            405                 410                 415

Asn Gly Thr Arg Ala Pro Asp Gly Thr Leu Trp Gly Glu Trp Gly Ser
            420                 425                 430

Leu Thr Ala Tyr Ser Ser Asp Trp Gln Ser Gly Glu Tyr Trp Val Lys
            435                 440                 445

Lys Thr Ser Thr Asp Phe Glu Thr Met Asn Met Asp Thr Gly Ala Leu
            450                 455                 460

Gln Pro Gly Pro Ala Tyr Leu Ala Phe Pro Leu Cys Ala Leu Ser Ile
465                 470                 475                 480

<210> SEQ ID NO 3
<211> LENGTH: 1075
<212> TYPE: PRT
<213> ORGANISM: Yersinia pseudotuberculosis
<220> FEATURE:
<221> NAME/KEY: InvB YPK_2513
<222> LOCATION: (1)..(1075)

<400> SEQUENCE: 3

Met Ser Leu Tyr Arg Ile Ser Ser Leu His Gln Ala Lys Gln Leu Asn
1               5                   10                  15

Lys Asn Lys Gln Leu Asn Lys Thr Arg Ile Ser Lys Ser Val Val Trp
            20                  25                  30

Ala Asn Ile Val Ile Gln Ala Ile Phe Pro Leu Ser Ile Ala Phe Thr
        35                  40                  45

Pro Ala Val Met Ala Ala Glu Thr Val Gly Ala Ser Asp Glu Lys Pro
    50                  55                  60

Arg Ser Ala Ser Gln Ala Glu Gln Ser Thr Ala Asn Ala Ala Thr Arg
65                  70                  75                  80

Leu Ala Ser Ile Leu Thr Asn Asp Asp Ser Ala Lys Gln Ala Ser Ser
            85                  90                  95

Ile Ala Arg Gly Thr Ala Ala Asn Ala Gly Asn Glu Ala Leu Gln Lys
            100                 105                 110

Trp Phe Asn Gln Phe Gly Ser Ala Lys Val Gln Leu Asn Leu Asp Glu
        115                 120                 125
```

```
Lys Leu Ser Leu Lys Gly Ser Gln Leu Asp Val Leu Leu Pro Leu Thr
    130                 135                 140

Asp Ser Pro Asp Leu Leu Thr Phe Thr Gln Leu Gly Gly Arg Tyr Ile
145                 150                 155                 160

Asp Asp Arg Val Thr Leu Asn Val Gly Leu Gly Gln Arg His Phe Phe
                165                 170                 175

Ala Gln Gln Met Leu Gly Tyr Asn Leu Phe Val Asp His Asp Ala Ser
            180                 185                 190

Tyr Ser His Thr Arg Ile Gly Val Gly Ala Glu Tyr Gly Arg Asp Phe
        195                 200                 205

Ile Asn Leu Ala Ala Asn Gly Tyr Phe Gly Val Ser Gly Trp Lys Asn
210                 215                 220

Ser Pro Asp Leu Asp Lys Tyr Asp Glu Lys Val Ala Asn Gly Phe Asp
225                 230                 235                 240

Leu Arg Ser Glu Ala Tyr Leu Pro Thr Leu Pro Gln Leu Gly Gly Lys
                245                 250                 255

Leu Ile Tyr Glu Gln Tyr Phe Gly Asp Glu Val Gly Leu Phe Gly Val
            260                 265                 270

Asp Asn Arg Gln Lys Asn Pro Leu Ala Val Thr Leu Gly Val Asn Tyr
        275                 280                 285

Thr Pro Ile Pro Leu Phe Thr Val Gly Val Asp His Lys Met Gly Arg
290                 295                 300

Ala Gly Met Asn Asp Thr Arg Phe Asn Leu Gly Phe Asn Tyr Ala Phe
305                 310                 315                 320

Gly Thr Pro Leu Ala His Gln Leu Asp Ser Asp Ala Val Ala Ile Lys
                325                 330                 335

Arg Ser Leu Met Gly Ser Arg Tyr Asn Leu Val Asp Arg Asn Asn Gln
            340                 345                 350

Ile Val Met Lys Tyr Arg Lys Gln Asn Arg Val Thr Leu Glu Leu Pro
        355                 360                 365

Ala Arg Val Ser Gly Ala Ala Arg Gln Thr Met Pro Leu Val Ala Asn
370                 375                 380

Ala Thr Ala Gln Gln Gly Ile Asp Arg Ile Glu Trp Glu Ala Ser Ala
385                 390                 395                 400

Leu Thr Leu Ala Gly Gly Lys Ile Thr Gly Ser Gly Asn Asn Trp Gln
                405                 410                 415

Ile Thr Leu Pro Ser Tyr Leu Ser Gly Gly Glu Gly Asn Asn Thr Tyr
            420                 425                 430

Arg Ile Ser Ala Ile Ala Tyr Asp Thr Leu Gly Asn Ala Ser Pro Val
        435                 440                 445

Ala Tyr Ser Asp Leu Val Val Asp Ser His Gly Val Asn Thr Asn Ala
450                 455                 460

Ser Gly Leu Thr Ala Ala Pro Glu Ile Leu Pro Ala Asn Ala Ser Ala
465                 470                 475                 480

Ser Ser Val Ile Glu Phe Asn Ile Lys Asp Asn Ala Asn Gln Pro Ile
                485                 490                 495

Thr Gly Ile Ala Asp Glu Leu Ala Phe Ser Leu Glu Leu Val Glu Leu
            500                 505                 510

Pro Glu Glu Leu Ala Lys Ala Lys Ala Arg Ser Val Pro Leu Lys Thr
        515                 520                 525

Val Ser His Thr Leu Thr Lys Ile Thr Glu Ser Ala Pro Gly Ile Tyr
530                 535                 540

Gln Ala Thr Leu Thr Ser Gly Ser Lys Pro Gln Leu Ile Asn Ile Thr
```

```
                                -continued 545                 550                 555                 560
Ala Gln Ile Asn Gly Val Pro Leu Ala Asp Val Gln Thr Lys Val Thr
                565                 570                 575

Leu Ile Ala Asp Glu Asn Thr Ala Thr Leu Gln Thr Ser Ser Leu Gln
                580                 585                 590

Ile Ile Thr Asn Gly Ser Leu Ala Asp Asp Thr Asp Ala Asn Gln Ile
                595                 600                 605

Arg Ala Val Val Val Asp Ala Tyr Gly Asn Lys Leu Ser Gly Val Gln
                610                 615                 620

Val Asn Phe Thr Val Gly Asn Asn Ala Lys Ile Thr Glu Thr Thr Leu
625                 630                 635                 640

Ser Asp Lys Gln Gly Gly Val Thr Ala Ala Ile Thr Ser Thr Lys Ala
                645                 650                 655

Gly Thr Tyr Thr Val Thr Ala Glu Leu Asn Gly Val Thr Gln Gln Ile
                660                 665                 670

Asp Val Asn Phe Ile Pro Asp Ala Gly Thr Ala Thr Leu Asp Asp Ser
                675                 680                 685

Asp Glu Tyr Lys Leu Gln Trp Val Thr Asn Gly Gln Val Ala Asp Gly
                690                 695                 700

Glu Ser Thr Asn Ser Val Gln Leu Thr Val Val Asp Lys Phe Gly Asn
705                 710                 715                 720

Thr Val Pro Gly Val Asp Val Ala Phe Thr Thr Asp Ile Gly Ala Ile
                725                 730                 735

Ile Ser Glu Val Thr Pro Thr Asp Ala Asn Gly Val Ala Thr Ala Lys
                740                 745                 750

Ile Ile Ser Ser Gln Ala Lys Ser His Thr Val Lys Ala Thr Leu Asn
                755                 760                 765

Arg Lys Glu Gln Thr Val Glu Val Asn Phe Ile Ala Asp Thr Ala Thr
                770                 775                 780

Ala Glu Ile Thr Ala Asn Asn Phe Thr Val Glu Val Asp Gly Gln Val
785                 790                 795                 800

Ala Gly Ser Gly Thr Asn Gln Val Gln Ala Leu Val Val Asp Lys Lys
                805                 810                 815

Gly Asn Pro Val Ala Asn Met Thr Val Asn Phe Thr Ala Thr Asn Gly
                820                 825                 830

Val Val Ala Glu Thr Thr Ser Ala Lys Thr Asp Glu Asn Gly Lys Val
                835                 840                 845

Thr Thr Asn Leu Ser Met Thr Asn Val Gly Gly Thr Ile Ser Thr Val
850                 855                 860

Thr Ala Thr Met Ile Asn Ser Ala Asn Val Thr Ser Thr Gln Asp Lys
865                 870                 875                 880

Pro Val Ile Phe Tyr Pro Asp Phe Thr Lys Ala Thr Leu Asn Thr Pro
                885                 890                 895

Ala Asn Thr Tyr Ser Gly Phe Asn Ile Asn Ser Gly Phe Pro Thr Thr
                900                 905                 910

Gly Phe Lys Asn Thr His Phe Gln Leu Ser Pro His Gly Ile Thr Gly
                915                 920                 925

Ala Asn Ser Asp Tyr Asp Trp Val Ser Ser His Pro Asn Val Ser Val
                930                 935                 940

Ser Asn Thr Gly Ala Ile Thr Leu Gln Asp Asn Pro Gly Gly Lys Val
945                 950                 955                 960

Thr Ile Thr Ala Thr Trp Lys His Asp Ser Ser Lys Val Phe Thr Tyr
                965                 970                 975
```

-continued

Asp Phe Thr Leu Asn Tyr Trp Val Gly Leu Tyr Ser Ser Thr Asn Leu
              980                 985                 990

Ser Trp Ala Gln Ala Asn Ala Ser Cys Ile Asn Ala Gly Met Arg Leu
        995                1000                1005

Pro Thr Asn Ser Glu Val Ser Ala Gly Gln Asp Val Arg Gly Val
    1010                1015                1020

Gly Ser Leu Phe Gly Glu Trp Gly Asn Leu Asn Ala Tyr Pro Ser
    1025                1030                1035

Phe Pro Thr Ala Gln Ile Ile Trp Thr Ser Val Asp Thr Asn Asp
    1040                1045                1050

Phe His Ile Asp Thr Gly Leu Thr His Ser Ala Ser Asn Val Thr
    1055                1060                1065

Leu Ala Tyr Met Cys Ile Lys
    1070                1075

<210> SEQ ID NO 4
<211> LENGTH: 5337
<212> TYPE: PRT
<213> ORGANISM: Yersinia pseudotuberculosis
<220> FEATURE:
<221> NAME/KEY: InvC YPK_0145
<222> LOCATION: (01)..(5337)

<400> SEQUENCE: 4

Met Leu Asn Tyr Phe Arg Ala Ile Leu Ile Ser Trp Lys Trp Lys Leu
1               5                   10                  15

Ser His His Thr Ser Arg Pro His Asp Val Lys Glu Lys Gly His Pro
            20                  25                  30

Arg Lys Ile Lys Val Val Ala Trp Ile Thr Leu Phe Phe Gln Phe Ala
        35                  40                  45

Phe Pro Leu Ser Leu Ser Phe Thr Pro Ala Ile Ala Ala Ala Asn Thr
    50                  55                  60

Thr Asn Ser Ala Pro Thr Ser Val Ile Thr Pro Val Asn Ala Ser Ile
65                  70                  75                  80

Leu Pro Pro Ala Ala Arg Ala Thr Glu Pro Tyr Thr Leu Gly Pro Gly
                85                  90                  95

Asp Ser Ile Gln Ser Ile Ala Lys Lys Tyr Asn Ile Thr Val Asp Glu
            100                 105                 110

Leu Lys Lys Leu Asn Ala Tyr Arg Thr Phe Ser Lys Pro Phe Ala Ser
        115                 120                 125

Leu Thr Thr Gly Asp Glu Ile Glu Val Pro Arg Lys Glu Ser Ser Phe
    130                 135                 140

Phe Ser Asn Asn Pro Asn Glu Asn Asn Lys Lys Asp Val Asp Asp Leu
145                 150                 155                 160

Leu Ala Arg Asn Ala Met Gly Ala Gly Lys Leu Leu Ser Asn Asp Asn
                165                 170                 175

Thr Ser Asp Ala Ala Ser Asn Met Ala Arg Ser Ala Val Thr Asn Glu
            180                 185                 190

Ile Asn Ala Ser Ser Gln Gln Trp Leu Asn Gln Phe Gly Thr Ala Arg
        195                 200                 205

Val Gln Leu Asn Val Asp Ser Asp Phe Lys Leu Asp Asn Ser Ala Leu
    210                 215                 220

Asp Leu Leu Val Pro Leu Lys Asp Ser Glu Ser Ser Leu Leu Phe Thr
225                 230                 235                 240

Gln Leu Gly Val Arg Asn Lys Asp Ser Arg Asn Thr Val Asn Ile Gly

```
                        245                 250                 255
Ala Gly Ile Arg Gln Tyr Gln Gly Asp Trp Met Tyr Gly Ala Asn Thr
            260                 265                 270

Phe Phe Asp Asn Asp Leu Thr Gly Lys Asn Arg Arg Val Gly Val Gly
        275                 280                 285

Ala Glu Val Ala Thr Asp Tyr Leu Lys Phe Ser Ala Asn Thr Tyr Phe
290                 295                 300

Gly Leu Thr Gly Trp His Gln Ser Arg Asp Phe Ser Ser Tyr Asp Glu
305                 310                 315                 320

Arg Pro Ala Asp Gly Phe Asp Ile Arg Thr Glu Ala Tyr Leu Pro Ala
                325                 330                 335

Tyr Pro Gln Leu Gly Gly Lys Leu Met Tyr Glu Lys Tyr Arg Gly Asp
            340                 345                 350

Glu Val Ala Leu Phe Gly Lys Asp Asp Arg Gln Lys Asp Pro His Ala
        355                 360                 365

Val Thr Leu Gly Val Asn Tyr Thr Pro Val Pro Leu Val Thr Ile Gly
370                 375                 380

Ala Glu His Arg Glu Gly Lys Gly Asn Asn Asn Thr Ser Val Asn
385                 390                 395                 400

Val Gln Leu Asn Tyr Arg Met Gly Gln Pro Trp Asn Asp Gln Ile Asp
                405                 410                 415

Gln Ser Ala Val Ala Ala Asn Arg Thr Leu Ala Gly Ser Arg Tyr Asp
            420                 425                 430

Leu Val Glu Arg Asn Asn Asn Ile Val Leu Asp Tyr Lys Lys Gln Glu
        435                 440                 445

Leu Ile His Leu Val Leu Pro Asp Arg Ile Ser Gly Ser Gly Gly Gly
450                 455                 460

Ala Ile Thr Leu Thr Ala Gln Val Arg Ala Lys Tyr Gly Phe Ser Arg
465                 470                 475                 480

Ile Glu Trp Asp Ala Thr Pro Leu Glu Asn Ala Gly Gly Ser Thr Ser
                485                 490                 495

Pro Leu Thr Gln Ser Ser Leu Ser Val Thr Leu Pro Phe Tyr Gln His
            500                 505                 510

Ile Leu Arg Thr Ser Asn Thr His Thr Ile Ser Ala Val Ala Tyr Asp
        515                 520                 525

Ala Gln Gly Asn Ala Ser Asn Arg Ala Val Thr Ser Ile Glu Val Thr
530                 535                 540

Arg Pro Glu Thr Met Val Ile Ser His Leu Ala Thr Thr Val Asp Asn
545                 550                 555                 560

Ala Thr Ala Asn Gly Ile Ala Ala Asn Thr Val Gln Ala Thr Val Thr
                565                 570                 575

Asp Gly Asp Gly Gln Pro Ile Ile Gly Gln Ile Asn Phe Ala Val
            580                 585                 590

Asn Thr Gln Ala Thr Leu Ser Thr Thr Glu Ala Arg Thr Gly Ala Asn
        595                 600                 605

Gly Ile Ala Ser Thr Thr Leu Thr His Thr Val Ala Gly Val Ser Ala
610                 615                 620

Val Ser Ala Thr Leu Gly Ser Ser Ser Arg Ser Val Asn Thr Thr Phe
625                 630                 635                 640

Val Ala Asp Glu Ser Thr Ala Glu Ile Thr Ala Ala Asn Leu Thr Val
                645                 650                 655

Thr Thr Asn Asp Ser Val Ala Asn Gly Ser Asp Thr Asn Ala Val Arg
            660                 665                 670
```

```
Ala Lys Val Thr Asp Ala Tyr Thr Asn Ala Val Ala Asn Gln Ser Val
        675                 680                 685

Ile Phe Ser Ala Ser Asn Gly Ala Thr Val Ile Asp Gln Thr Val Ile
        690                 695                 700

Thr Asn Ala Glu Gly Ile Ala Asp Ser Thr Leu Thr Asn Thr Thr Ala
705                 710                 715                 720

Gly Val Ser Ala Val Thr Ala Thr Leu Gly Ser Gln Ser Gln Gln Val
                725                 730                 735

Asp Thr Thr Phe Lys Pro Gly Ser Thr Ala Ala Ile Ser Leu Val Lys
            740                 745                 750

Leu Ala Asp Arg Ala Val Ala Asp Gly Ile Asp Gln Asn Glu Ile Gln
        755                 760                 765

Val Val Leu Arg Asp Gly Thr Gly Asn Ala Val Pro Asn Val Pro Met
770                 775                 780

Ser Ile Gln Ala Asp Asn Gly Ala Ile Val Val Ala Ser Thr Pro Asn
785                 790                 795                 800

Thr Gly Val Asp Gly Thr Ile Asn Ala Thr Phe Thr Asn Leu Arg Ala
                805                 810                 815

Gly Glu Ser Val Val Ser Val Thr Ser Pro Ala Leu Val Gly Met Thr
            820                 825                 830

Met Thr Met Thr Phe Ser Ala Asp Gln Arg Thr Ala Val Val Ser Thr
        835                 840                 845

Leu Ala Ala Ile Asp Asn Asn Ala Lys Ala Asp Gly Thr Asp Thr Asn
850                 855                 860

Val Val Arg Ala Trp Val Asp Ala Asn Gly Asn Ser Val Pro Gly
865                 870                 875                 880

Val Ser Val Thr Phe Asp Ala Gly Asn Gly Ala Val Leu Ala Gln Asn
                885                 890                 895

Pro Val Val Thr Asp Arg Asn Gly Tyr Ala Glu Asn Thr Leu Thr Asn
            900                 905                 910

Leu Ala Ile Gly Thr Thr Thr Val Lys Ala Thr Thr Val Thr Asp Pro
        915                 920                 925

Val Gly Gln Thr Val Asn Thr His Phe Val Ala Gly Ala Val Asp Thr
930                 935                 940

Ile Thr Leu Thr Val Leu Val Asn Gly Ala Val Ala Asn Gly Val Asn
945                 950                 955                 960

Thr Asn Ser Val Gln Ala Val Val Ser Asp Ser Gly Gly Asn Pro Val
                965                 970                 975

Asn Gly Ala Ala Val Val Phe Ser Ser Ala Asn Ala Thr Ala Gln Ile
            980                 985                 990

Thr Thr Val Ile Gly Thr Thr Gly Val Asp Gly Ile Ala Thr Ala Thr
        995                 1000                1005

Leu Thr Asn Thr Val Ala Gly Thr Ser Asn Val Val Ala Thr Ile
        1010                1015                1020

Asp Thr Val Asn Ala Asn Ile Asp Thr Thr Phe Val Ala Gly Ala
        1025                1030                1035

Val Ala Thr Ile Thr Leu Thr Thr Leu Val Asn Gly Ala Val Ala
        1040                1045                1050

Asp Gly Ala Asn Ser Asn Ser Val Gln Ala Val Val Ser Asp Ser
        1055                1060                1065

Gly Gly Asn Pro Val Thr Gly Ala Ala Val Val Phe Ser Ser Ala
        1070                1075                1080
```

```
Asn Ala Thr Ala Gln Ile Thr Thr Val Ile Gly Thr Thr Gly Val
    1085                1090                1095

Asp Gly Ile Ala Thr Ala Thr Leu Thr Asn Thr Val Ala Gly Thr
    1100                1105                1110

Ser Asn Val Val Ala Thr Ile Gly Ser Ile Thr Asn Asn Ile Asp
    1115                1120                1125

Thr Ala Phe Val Ala Gly Ala Val Ala Thr Ile Thr Leu Thr Thr
    1130                1135                1140

Pro Val Asn Gly Ala Val Ala Asp Gly Ala Asn Ser Asn Ser Val
    1145                1150                1155

Gln Ala Val Val Thr Asp Ser Gly Gly Asn Pro Val Asn Gly Ala
    1160                1165                1170

Ala Val Val Phe Ser Ser Ala Asn Ala Thr Ala Gln Ile Thr Thr
    1175                1180                1185

Val Ile Gly Thr Thr Gly Ala Asp Gly Ile Ala Thr Ala Thr Leu
    1190                1195                1200

Thr Asn Thr Val Ala Gly Thr Ser Asn Val Val Ala Thr Val Asp
    1205                1210                1215

Thr Val Asn Ala Asn Ile Asp Thr Thr Phe Val Ala Gly Ala Val
    1220                1225                1230

Ala Thr Ile Thr Leu Thr Thr Pro Val Asn Gly Ala Val Ala Asp
    1235                1240                1245

Gly Ala Asp Ser Asn Ser Val Gln Ala Val Val Ser Asp Ser Gly
    1250                1255                1260

Gly Asn Pro Val Ala Gly Ala Ala Val Val Phe Ser Ser Ala Asn
    1265                1270                1275

Ala Thr Ala Gln Val Thr Thr Val Ile Gly Thr Thr Gly Ala Asp
    1280                1285                1290

Gly Ile Ala Thr Ala Thr Leu Thr Asn Thr Val Ala Gly Thr Ser
    1295                1300                1305

Asn Val Val Ala Thr Ile Gly Ser Ile Thr Asn Asn Ile Asp Thr
    1310                1315                1320

Ala Phe Val Ala Gly Ala Val Ala Thr Ile Thr Leu Ser Val Pro
    1325                1330                1335

Val Asn Asp Ala Thr Ala Asp Gly Val Asp Thr Asn Gln Val Asp
    1340                1345                1350

Ala Leu Val Gln Asp Ala Asn Gly Asn Ala Ile Thr Gly Ala Ala
    1355                1360                1365

Val Val Phe Ser Ser Thr Asn Gly Ala Asp Ile Ile Val Pro Thr
    1370                1375                1380

Met Asn Thr Gly Val Asn Gly Val Ala Ser Thr Leu Leu Thr His
    1385                1390                1395

Thr Val Ala Gly Thr Ser Asn Val Val Ala Thr Val Asp Thr Val
    1400                1405                1410

Asn Ala Asn Ile Asp Thr Ala Phe Val Pro Gly Ala Val Ala Thr
    1415                1420                1425

Ile Thr Leu Thr Thr Pro Val Asn Gly Ala Val Ala Asp Gly Ala
    1430                1435                1440

Asn Ser Asn Ser Val Gln Ala Val Val Ser Asp Ser Glu Gly Asn
    1445                1450                1455

Ala Val Ala Gly Ala Ala Val Val Phe Ser Ser Ala Asn Ala Thr
    1460                1465                1470

Ala Gln Ile Thr Thr Val Ile Gly Thr Thr Gly Ala Asp Gly Ile
```

```
                1475                1480                1485

Ala Thr  Ala Thr Leu Thr Asn  Thr Val Ala Gly Thr  Ser Asn Val
    1490                 1495                 1500

Val Ala  Thr Ile Asp Thr Val  Asn Ala Asn Ile Asp  Thr Ala Phe
    1505                 1510                 1515

Val Pro  Gly Ala Val Ala Thr  Ile Thr Leu Ser Val  Leu Val Asn
    1520                 1525                 1530

Asp Ala  Thr Ala Asp Gly Ala  Asp Thr Asn Gln Val  Asp Ala Leu
    1535                 1540                 1545

Val Gln  Asp Ala Asn Gly Asn  Ala Ile Thr Gly Ala  Ala Val Val
    1550                 1555                 1560

Phe Ser  Ser Ala Asn Gly Ala  Asp Ile Ile Ala Pro  Thr Met Asn
    1565                 1570                 1575

Thr Gly  Val Asn Gly Val Ala  Ser Thr Leu Leu Thr  His Thr Gln
    1580                 1585                 1590

Ser Gly  Val Ser Asn Val Val  Ala Thr Ile Asp Thr  Val Asn Ala
    1595                 1600                 1605

Asn Ile  Asp Thr Thr Phe Val  Ala Gly Ala Val Ala  Ala Ile Thr
    1610                 1615                 1620

Leu Thr  Thr Pro Val Asp Gly  Ala Val Ala Asp Gly  Thr Asp Ser
    1625                 1630                 1635

Asn Ser  Val Gln Ala Val Val  Ser Asp Ser Glu Gly  Asn Ala Val
    1640                 1645                 1650

Ala Gly  Ala Ala Val Val Phe  Ser Ser Ala Asn Ala  Thr Ala Gln
    1655                 1660                 1665

Ile Thr  Thr Val Ile Gly Thr  Thr Gly Ala Asp Gly  Ile Ala Thr
    1670                 1675                 1680

Ala Thr  Leu Thr Asn Thr Val  Ala Gly Thr Ser Asn  Val Ala Ala
    1685                 1690                 1695

Thr Ile  Gly Ser Ile Thr Asp  Asn Ile Asp Thr Val  Phe Val Ala
    1700                 1705                 1710

Gly Ala  Val Ala Thr Ile Thr  Leu Ser Val Pro Val  Asn Asp Ala
    1715                 1720                 1725

Thr Ala  Asp Gly Ala Asp Thr  Asn Gln Val Asp Ala  Leu Val Gln
    1730                 1735                 1740

Asp Val  Asn Gly Asn Ala Ile  Thr Gly Ala Ala Val  Val Phe Ser
    1745                 1750                 1755

Ser Ala  Asn Gly Ala Thr Ile  Leu Ser Ser Thr Val  Asn Thr Gly
    1760                 1765                 1770

Ala Asp  Gly Ile Ala Ser Thr  Thr Leu Thr His Thr  Gln Ser Gly
    1775                 1780                 1785

Val Ser  Asn Val Val Ala Thr  Ile Asp Thr Val Asn  Ala Asn Ile
    1790                 1795                 1800

Asp Thr  Thr Phe Val Ala Gly  Ala Val Ala Thr Ile  Thr Leu Ser
    1805                 1810                 1815

Val Leu  Val Asn Asp Ala Thr  Ala Asp Gly Ala Asp  Thr Asn Gln
    1820                 1825                 1830

Val Asp  Ala Leu Val Gln Asp  Ala Asn Gly Asn Ala  Ile Thr Gly
    1835                 1840                 1845

Ala Ala  Val Val Phe Ser Ser  Ala Asn Gly Ala Thr  Ile Ile Val
    1850                 1855                 1860

Pro Thr  Met Asn Thr Gly Ala  Asn Gly Val Ala Ser  Thr Leu Leu
    1865                 1870                 1875
```

-continued

Thr His Thr Val Ala Gly Thr Ser Asn Val Val Ala Thr Ile Gly
    1880                1885                1890

Ser Ile Thr Asn Asn Ile Asp Thr Ala Phe Val Ala Gly Ala Val
    1895                1900                1905

Ala Thr Ile Thr Leu Thr Thr Pro Val Asn Gly Ala Val Ala Asp
    1910                1915                1920

Gly Ala Asn Ser Asn Ser Val Gln Ala Val Val Ser Asp Ser Glu
    1925                1930                1935

Gly Asn Ala Val Ala Gly Ala Val Val Phe Ser Ser Ala Asn
    1940                1945                1950

Ala Thr Ala Gln Ile Thr Thr Val Ile Gly Thr Thr Gly Ala Asp
    1955                1960                1965

Gly Ile Ala Thr Ala Thr Leu Thr Asn Thr Val Ala Gly Thr Ser
    1970                1975                1980

Asn Val Val Ala Thr Ile Gly Ser Ile Thr Asp Asn Ile Asp Thr
    1985                1990                1995

Val Phe Val Ala Gly Ala Val Ala Thr Ile Thr Leu Thr Thr Pro
    2000                2005                2010

Val Asn Gly Ala Val Ala Asp Gly Ala Asn Ser Asn Ser Val Gln
    2015                2020                2025

Ala Val Val Ser Asp Ser Glu Gly Asn Pro Val Thr Gly Ala Thr
    2030                2035                2040

Val Val Phe Ser Ser Ser Asn Ala Thr Ala Gln Ile Thr Thr Val
    2045                2050                2055

Ile Gly Thr Thr Gly Ala Asp Gly Ile Ala Thr Ala Thr Leu Thr
    2060                2065                2070

Asn Thr Val Ala Gly Thr Ser Asn Val Val Ala Thr Ile Asp Thr
    2075                2080                2085

Val Asn Ala Asn Ile Asp Thr Thr Phe Val Pro Gly Ala Val Ala
    2090                2095                2100

Thr Ile Thr Leu Thr Thr Pro Val Asp Gly Ala Val Ala Asp Gly
    2105                2110                2115

Ala Asn Ser Asn Ser Val Gln Ala Val Val Thr Asp Ser Gly Gly
    2120                2125                2130

Asn Pro Val Thr Gly Ala Ala Val Val Phe Ser Ser Ala Asn Ala
    2135                2140                2145

Thr Ala Gln Ile Thr Thr Val Ile Gly Thr Thr Gly Ala Asp Gly
    2150                2155                2160

Ile Ala Thr Ala Thr Leu Thr Asn Thr Val Ala Gly Thr Ser Asn
    2165                2170                2175

Val Val Ala Thr Val Asp Thr Val Asn Ala Asn Ile Asp Thr Thr
    2180                2185                2190

Phe Val Ala Gly Ala Val Ala Thr Ile Thr Leu Thr Thr Pro Val
    2195                2200                2205

Asn Gly Ala Val Ala Asn Gly Ala Asp Ser Asn Ser Val Gln Ala
    2210                2215                2220

Val Val Ser Asp Ser Glu Gly Asn Ala Val Ala Gly Ala Ala Val
    2225                2230                2235

Val Phe Ser Ser Ala Asn Ala Thr Ala Gln Ile Thr Thr Val Ile
    2240                2245                2250

Gly Thr Thr Gly Ala Asp Gly Ile Ala Thr Ala Thr Leu Ile Asn
    2255                2260                2265

-continued

Thr Val Ala Gly Thr Ser Asn Val Val Ala Thr Ile Asp Thr Val
2270                2275                2280

Asn Ala Asn Ile Asp Thr Thr Phe Val Ala Gly Ala Val Ala Thr
2285                2290                2295

Ile Thr Leu Thr Thr Pro Val Asp Gly Ala Val Ala Asn Gly Ala
2300                2305                2310

Asp Ser Asn Ser Val Gln Ala Val Val Ser Asp Ser Glu Gly Asn
2315                2320                2325

Ala Val Ala Gly Ala Ala Val Val Phe Ser Ser Ala Asn Ala Thr
2330                2335                2340

Ala Gln Ile Thr Thr Val Ile Gly Thr Thr Gly Ala Asp Gly Ile
2345                2350                2355

Ala Thr Ala Thr Leu Thr Asn Thr Val Ala Gly Thr Ser Asn Val
2360                2365                2370

Val Ala Thr Ile Gly Ser Ile Thr Asn Asn Ile Asp Thr Ala Phe
2375                2380                2385

Val Ala Gly Ala Val Ala Thr Ile Thr Leu Thr Thr Pro Val Asn
2390                2395                2400

Gly Ala Val Ala Asp Gly Ala Asn Ser Asn Ser Val Gln Ala Val
2405                2410                2415

Val Thr Asp Ser Gly Gly Asn Pro Val Asn Gly Ala Ala Val Val
2420                2425                2430

Phe Ser Ser Ala Asn Ala Thr Ala Gln Ile Thr Thr Val Ile Gly
2435                2440                2445

Thr Thr Gly Ala Asp Gly Ile Ala Thr Ala Thr Leu Thr Asn Thr
2450                2455                2460

Val Ala Gly Thr Ser Asn Val Val Ala Thr Val Asp Thr Val Asn
2465                2470                2475

Ala Asn Ile Asp Thr Thr Phe Val Ala Gly Ala Val Ala Thr Ile
2480                2485                2490

Thr Leu Thr Thr Pro Val Asn Gly Ala Val Ala Asp Gly Ala Asp
2495                2500                2505

Ser Asn Ser Val Gln Ala Val Val Ser Asp Ser Gly Gly Asn Pro
2510                2515                2520

Val Ala Gly Ala Ala Val Val Phe Ser Ser Ala Asn Ala Thr Ala
2525                2530                2535

Gln Val Thr Thr Val Ile Gly Thr Thr Gly Ala Asp Gly Ile Ala
2540                2545                2550

Thr Ala Thr Leu Thr Asn Thr Val Ala Gly Thr Ser Asn Val Val
2555                2560                2565

Ala Thr Ile Gly Ser Ile Thr Asn Asn Ile Asp Thr Ala Phe Val
2570                2575                2580

Ala Gly Ala Val Ala Thr Ile Thr Leu Thr Thr Pro Val Asn Gly
2585                2590                2595

Ala Val Ala Asp Gly Ala Asp Ser Asn Ser Val Gln Ala Val Val
2600                2605                2610

Ser Asp Ser Glu Gly Asn Ala Val Thr Gly Ala Ala Val Val Phe
2615                2620                2625

Ser Ser Ala Asn Ala Thr Ala Gln Ile Thr Thr Val Ile Gly Thr
2630                2635                2640

Thr Gly Ala Asp Gly Ile Ala Thr Ala Thr Leu Thr Asn Thr Val
2645                2650                2655

Ala Gly Thr Ser Asn Val Val Ala Thr Ile Gly Gly Ile Thr Asn

```
                2660                2665                2670

Asn Ile Asp Thr Ala Phe Val Ala Gly Ala Val Ala Thr Ile Thr
        2675                2680                2685

Leu Thr Thr Pro Val Asn Gly Ala Val Ala Asp Gly Thr Asp Ser
        2690                2695                2700

Asn Ser Val Gln Ala Val Val Ser Asp Ser Glu Gly Asn Ala Val
        2705                2710                2715

Ala Gly Ala Ala Val Val Phe Ser Ser Ala Asn Ala Thr Ala Gln
        2720                2725                2730

Ile Thr Thr Val Ile Gly Thr Thr Gly Ala Asp Gly Ile Ala Thr
        2735                2740                2745

Ala Thr Leu Thr Asn Thr Val Ala Gly Thr Ser Asn Val Val Ala
        2750                2755                2760

Thr Ile Gly Ser Ile Thr Asn Asn Ile Asp Thr Ala Phe Val Ala
        2765                2770                2775

Gly Ala Val Ala Thr Ile Thr Leu Thr Thr Leu Val Asn Gly Ala
        2780                2785                2790

Val Ala Asn Gly Ala Asp Ser Asn Ser Val Gln Ala Val Val Ser
        2795                2800                2805

Asp Ser Gly Gly Asn Val Val Ala Gly Ala Thr Val Val Phe Ser
        2810                2815                2820

Ser Thr Asn Ala Thr Ala Gln Val Thr Thr Val Ile Gly Thr Thr
        2825                2830                2835

Gly Ala Asp Gly Ile Ala Thr Ala Thr Leu Thr Asn Thr Val Ala
        2840                2845                2850

Gly Thr Ser Asn Val Val Ala Thr Ile Asp Thr Val Asn Ala Asn
        2855                2860                2865

Ile Asp Thr Thr Phe Val Ala Gly Ala Val Ala Thr Ile Thr Leu
        2870                2875                2880

Ser Val Leu Val Asn Asp Ala Thr Ala Asp Gly Ala Asp Thr Asn
        2885                2890                2895

Gln Val Asp Ala Leu Val Gln Asp Ala Asn Gly Asn Ala Ile Thr
        2900                2905                2910

Gly Ala Ala Val Val Phe Ser Ser Ala Asn Gly Ala Thr Ile Leu
        2915                2920                2925

Ser Ser Thr Met Asn Thr Gly Val Asn Gly Val Ala Ser Thr Leu
        2930                2935                2940

Leu Thr His Thr Val Ala Gly Thr Ser Asn Val Val Ala Thr Ile
        2945                2950                2955

Asp Thr Val Asn Ala Asn Ile Asp Thr Ala Phe Val Ala Gly Ala
        2960                2965                2970

Val Ala Thr Ile Thr Leu Thr Thr Pro Val Asn Gly Ala Val Ala
        2975                2980                2985

Asn Gly Ala Asp Ser Asn Ser Val Gln Ala Val Val Ser Asp Ser
        2990                2995                3000

Glu Gly Asn Ala Val Ala Gly Ala Ala Val Val Phe Ser Ser Ala
        3005                3010                3015

Asn Ala Thr Ala Gln Ile Thr Val Ile Gly Thr Thr Gly Val
        3020                3025                3030

Asp Gly Ile Ala Thr Ala Thr Leu Thr Asn Thr Val Ala Gly Thr
        3035                3040                3045

Ser Asn Val Val Ala Thr Val Asp Thr Val Asn Ala Asn Ile Asp
        3050                3055                3060
```

-continued

Thr Ala Phe Val Ala Gly Ala Val Ala Thr Ile Thr Leu Thr Thr
3065                3070                3075

Pro Val Asn Gly Ala Val Ala Asn Gly Ala Asp Ser Asn Ser Val
3080                3085                3090

Gln Ala Val Val Ser Asp Ser Gly Gly Asn Val Val Ala Gly Ala
3095                3100                3105

Thr Val Val Phe Ser Ser Thr Asn Thr Thr Ala Gln Val Thr Thr
3110                3115                3120

Val Ile Gly Thr Thr Gly Ala Asp Gly Ile Ala Thr Ala Thr Leu
3125                3130                3135

Thr Asn Thr Val Ala Gly Thr Ser Asn Val Val Ala Thr Val Asp
3140                3145                3150

Thr Val Asn Ala Asn Ile Asp Thr Thr Phe Val Ala Gly Ala Val
3155                3160                3165

Ala Thr Ile Thr Leu Ser Val Leu Val Asn Asp Ala Thr Ala Asp
3170                3175                3180

Gly Ala Asp Thr Asn Gln Val Asp Ala Leu Val Gln Asp Ala Asn
3185                3190                3195

Gly Asn Ala Ile Thr Gly Ala Ala Val Val Phe Ser Ser Ala Asn
3200                3205                3210

Gly Ala Asp Ile Ile Ala Pro Thr Met Asn Thr Gly Val Asn Gly
3215                3220                3225

Val Ala Ser Thr Leu Leu Thr His Thr Met Ala Gly Thr Ser Asn
3230                3235                3240

Val Ile Ala Thr Ile Asp Thr Val Asn Ala Asn Ile Asp Thr Thr
3245                3250                3255

Phe Val Ala Gly Ala Val Ala Thr Ile Thr Leu Ser Val Pro Val
3260                3265                3270

Asn Asp Ala Thr Ala Asp Gly Ala Asp Thr Asn Gln Val Asp Ala
3275                3280                3285

Leu Val Gln Asp Ala Asn Gly Asn Ala Ile Thr Gly Ala Ala Val
3290                3295                3300

Val Phe Ser Ser Ala Asn Gly Ala Thr Ile Leu Ser Ser Thr Met
3305                3310                3315

Asn Thr Gly Val Asn Gly Val Ala Ser Thr Leu Leu Thr His Thr
3320                3325                3330

Gln Ser Gly Val Ser Asn Val Ala Thr Ile Asp Thr Val Asn
3335                3340                3345

Ala Asn Ile Asp Thr Ala Phe Val Ala Gly Ala Val Ala Thr Ile
3350                3355                3360

Thr Leu Thr Thr Pro Val Asn Gly Ala Val Ala Asp Gly Ala Asn
3365                3370                3375

Ser Asn Ser Val Gln Ala Val Val Thr Asp Ser Gly Gly Asn Pro
3380                3385                3390

Val Asn Gly Ala Ala Val Val Phe Ser Ser Ala Asn Ala Thr Ala
3395                3400                3405

Gln Ile Thr Thr Val Ile Gly Thr Thr Gly Ala Asp Gly Ile Ala
3410                3415                3420

Thr Ala Thr Leu Thr Asn Thr Val Ala Gly Thr Ser Asn Val Ala
3425                3430                3435

Ala Thr Ile Asp Thr Val Asn Ala Asn Ile Asp Thr Thr Phe Val
3440                3445                3450

| | | | | | | | | | | |
|---|---|---|---|---|---|---|---|---|---|---|
| Ala | Gly | Ala | Val | Ala | Thr | Ile | Thr | Leu | Thr | Thr | Pro | Val | Asn | Gly |
| | 3455 | | | | 3460 | | | | 3465 | | | | | |

Ala Gly Ala Val Ala Thr Ile Thr Leu Thr Thr Pro Val Asn Gly
    3455                3460                3465

Ala Val Ala Asp Gly Ala Asn Ser Asn Ser Val Gln Ala Val Val
    3470                3475                3480

Ser Asp Ser Glu Gly Asn Pro Val Asn Gly Ala Thr Val Val Phe
    3485                3490                3495

Ser Ser Ile Asn Ala Thr Ala Gln Ile Thr Thr Val Ile Gly Thr
    3500                3505                3510

Thr Gly Val Asp Gly Ile Ala Thr Ala Thr Leu Thr Asn Thr Val
    3515                3520                3525

Ala Gly Thr Ser Asn Val Val Ala Thr Ile Asp Thr Val Asn Ala
    3530                3535                3540

Asn Ile Asp Thr Thr Phe Val Ala Gly Ala Val Ala Thr Ile Thr
    3545                3550                3555

Leu Thr Thr Leu Val Asn Gly Ala Val Ala Asp Gly Ala Asn Ser
    3560                3565                3570

Asn Ser Val Gln Ala Val Val Ser Asp Ser Gly Gly Asn Pro Val
    3575                3580                3585

Thr Gly Ala Ala Val Val Phe Ser Ser Ala Asn Ala Thr Ala Gln
    3590                3595                3600

Ile Thr Thr Val Ile Gly Thr Thr Gly Val Asp Gly Ile Ala Thr
    3605                3610                3615

Ala Thr Leu Thr Asn Thr Val Ala Gly Thr Ser Asn Val Val Ala
    3620                3625                3630

Thr Ile Gly Ser Ile Thr Asn Asn Ile Asp Thr Ala Phe Val Ala
    3635                3640                3645

Gly Ala Val Ala Thr Ile Thr Leu Thr Thr Pro Val Asn Gly Ala
    3650                3655                3660

Val Ala Asp Gly Ala Asn Ser Asn Ser Val Gln Ala Val Val Thr
    3665                3670                3675

Asp Ser Gly Gly Asn Pro Val Asn Gly Ala Ala Val Val Phe Ser
    3680                3685                3690

Ser Ala Asn Ala Thr Ala Gln Ile Thr Thr Val Ile Gly Thr Thr
    3695                3700                3705

Gly Ala Asp Gly Ile Ala Thr Ala Thr Leu Thr Asn Thr Val Ala
    3710                3715                3720

Gly Thr Ser Asn Val Ile Ala Thr Ile Asp Thr Val Asn Ala Asn
    3725                3730                3735

Ile Asp Thr Thr Phe Val Ala Gly Ala Val Ala Thr Ile Thr Leu
    3740                3745                3750

Thr Thr Pro Val Asn Gly Ala Val Ala Asp Gly Ala Asp Ser Asn
    3755                3760                3765

Ser Val Gln Ala Val Val Ser Asp Ser Glu Gly Asn Ala Val Thr
    3770                3775                3780

Gly Ala Ala Val Val Phe Ser Ser Ala Asn Ala Thr Ala Gln Ile
    3785                3790                3795

Thr Thr Val Ile Gly Thr Thr Gly Ala Asp Gly Ile Ala Thr Ala
    3800                3805                3810

Thr Leu Thr Asn Thr Val Ala Gly Thr Ser Asn Val Val Ala Thr
    3815                3820                3825

Ile Asp Thr Val Asn Ala Asn Ile Asp Thr Ala Phe Val Ala Gly
    3830                3835                3840

Glu Leu Glu Asn Ile Val Val Ser Ile Ile Asn Asn Asn Ala Leu

```
            3845                3850                3855

Ala Asn Gly Ala Asp Thr Asn Ile Val Glu Ala Phe Val Thr Asp
        3860                3865                3870

Arg Phe Gly Asn Gly Val Ala Asn Gln Ser Leu Met Phe Gly Thr
        3875                3880                3885

Asn Gly Ala Ser Ile Val Gly Ser Ser Thr Val Thr Thr Asn Ile
        3890                3895                3900

Asp Gly Arg Val Arg Val Ser Ala Thr His Thr Val Ala Gly Ser
        3905                3910                3915

Ser Asn Thr Val Phe Ala Ile Ser Gly Ala His Gln Gly Tyr Thr
        3920                3925                3930

Arg Val Thr Phe Val Ala Asp Ala Ser Thr Ala Gln Leu Lys Leu
        3935                3940                3945

Thr Ser Phe Leu Asp Asn Gln Leu Ala Asn Gly Lys Ala Gly Asn
        3950                3955                3960

Ile Ala Gln Ala Leu Val Thr Asp Ala Tyr Asp Asn Pro Leu Ala
        3965                3970                3975

Asn Gln Ser Val Ser Phe Ala Leu Asp Asn Gly Ala Val Ile Glu
        3980                3985                3990

Ser Arg Gly Asp Ala Ser Ser Ala Ser Gly Ile Val Leu Met Arg
        3995                4000                4005

Phe Asn Asn Thr Leu Ala Gly Met Thr Thr Val Thr Ala Thr Leu
        4010                4015                4020

Asp Ser Thr Gly Gln Thr Glu Thr Leu Glu Met His Phe Val Ala
        4025                4030                4035

Gly Lys Ala Ala Ser Ile Glu Leu Thr Met Thr Lys Asp Asn Ala
        4040                4045                4050

Val Ala Asn Asn Ile Asp Thr Asn Glu Val Gln Val Leu Val Thr
        4055                4060                4065

Asp Ala Asp Gly Asn Ala Ile Asn Gly Ala Val Val Asn Leu Thr
        4070                4075                4080

Ser Asn Ser Gly Met Asn Ile Thr Pro Asn Ser Val Thr Thr Gly
        4085                4090                4095

Ser Asp Gly Thr Ala Thr Ala Thr Leu Thr His Thr Leu Ala Gly
        4100                4105                4110

Ser Leu Pro Ile Asn Ala Arg Ile Asp Gln Val Ser Lys Thr Ile
        4115                4120                4125

Asn Ala Thr Phe Ile Ala Asp Val Ser Thr Ala Gln Ile Ile Ala
        4130                4135                4140

Ser Asp Met Phe Ile Ile Val Asn Asp Gln Val Ala Asn Gly Gln
        4145                4150                4155

Ala Val Asn Ala Val Gln Ala Arg Val Thr Asp Ser Tyr Gly Asn
        4160                4165                4170

Pro Ile Gln Gly Gln Leu Val Glu Phe Val Leu Ser Asn Thr Gly
        4175                4180                4185

Thr Ile Gln Tyr Lys Leu Glu Glu Thr Ser Val Glu Gly Gly Val
        4190                4195                4200

Met Val Thr Phe Thr Asn Thr Leu Ala Gly Ile Thr Asn Val Thr
        4205                4210                4215

Ala Thr Val Val Ser Ser Arg Ser Ser Gln Asn Val Asp Thr Thr
        4220                4225                4230

Phe Ile Ala Asp Val Thr Thr Ala His Ile Ala Glu Ser Asp Leu
        4235                4240                4245
```

```
Met Val Ile Val Asp Asn Ala Val Ala Asn Asn Ser Glu Lys Asn
    4250            4255                4260

Glu Val His Ala Arg Val Thr Asp Ala Lys Gly Asn Val Leu Ser
    4265            4270                4275

Gly Gln Thr Val Ile Phe Thr Ser Gly Asn Gly Ala Ala Ile Thr
    4280            4285                4290

Thr Val Asn Gly Ile Ser Asp Gly Asp Gly Leu Thr Lys Ala Thr
    4295            4300                4305

Leu Thr His Thr Leu Ala Gly Thr Ser Val Val Thr Ala Arg Val
    4310            4315                4320

Gly Asn Gln Val Gln Ser Lys Asp Thr Thr Phe Ile Ala Asp Arg
    4325            4330                4335

Thr Thr Ala Thr Ile Arg Ala Ser Asp Leu Thr Ile Thr Arg Ser
    4340            4345                4350

Asn Ala Leu Ala Asp Gly Val Ala Thr Asn Ala Ala Arg Val Ile
    4355            4360                4365

Val Thr Asp Ala Tyr Gly Asn Pro Val Pro Ser Met Leu Val Ser
    4370            4375                4380

Tyr Thr Ser Glu Asn Gly Ala Thr Leu Thr Pro Thr Leu Gly Ser
    4385            4390                4395

Thr Asp Ser Ser Gly Met Leu Ser Thr Thr Phe Thr His Thr Ile
    4400            4405                4410

Ala Gly Ile Ser Lys Val Thr Ala Thr Ile Val Thr Met Gly Ile
    4415            4420                4425

Ser Gln Ala Lys Asp Ala Val Phe Ile Ala Asp Arg Thr Thr Ala
    4430            4435                4440

His Val Ser Ala Leu Thr Val Glu Lys Asn Asp Ser Leu Ala Asn
    4445            4450                4455

Asn Ser Asp Arg Asn Ile Val Gln Ala His Ile Gln Asp Ala His
    4460            4465                4470

Gly Asn Val Ile Thr Gly Met Asn Val Asn Phe Ser Ala Thr Glu
    4475            4480                4485

Asn Val Thr Leu Ala Ala Asn Met Val Thr Thr Asn Ala Gln Gly
    4490            4495                4500

Tyr Ala Glu Asn Thr Leu Arg His Asn Ala Pro Val Thr Ser Ala
    4505            4510                4515

Val Thr Ala Thr Val Ala Thr Asp Leu Val Gly Leu Thr Glu Asp
    4520            4525                4530

Val Arg Phe Val Ala Gly Ala Gly Ala Arg Ile Glu Leu Phe Arg
    4535            4540                4545

Leu Asn Asp Gly Ala Val Ala Asp Gly Ile Gln Thr Asn Arg Val
    4550            4555                4560

Glu Ala Arg Val Tyr Asp Val Ser Asp Asn Leu Val Pro Asn Ser
    4565            4570                4575

Asn Val Val Phe Ser Ala Asp Asn Gly Gly Gln Leu Val Gln Asn
    4580            4585                4590

Asp Val Gln Thr Asp Ala Leu Gly Ser Ala Tyr Val Thr Val Ser
    4595            4600                4605

Asn Ile Asn Thr Gly Val Thr Lys Val Ser Val Thr Ala Asp Gly
    4610            4615                4620

Val Ser Ala Ser Thr Thr Thr Thr Phe Ile Ala Asp Lys Asp Thr
    4625            4630                4635
```

-continued

Val Thr Leu Arg Ala Asp Leu Phe Leu Ile Thr His Asp Asn Ala
4640                4645                4650

Val Ala Asn Gly Val Thr Glu Asn Arg Val Leu Leu Gln Leu Leu
4655                4660                4665

Asp Ala Asn Asp Asn Lys Val Ser Gly Val Glu Val Asn Phe Thr
4670                4675                4680

Ala Thr Asn Gly Ala Ser Ile Asn Ala Ser Ala Ile Thr Asp Thr
4685                4690                4695

Asn Gly Leu Ala Ile Gly Val Leu Thr Asn Thr Leu Ser Gly Pro
4700                4705                4710

Ser Asp Val Thr Val Thr Leu Val Thr Pro Gly Gly Thr Glu Ser
4715                4720                4725

Leu Thr Val Thr Pro Gln Phe Ile Ala Asp Ile Asn Thr Ala Arg
4730                4735                4740

Ile Ala Asn Gly Asp Phe Val Ile Ile Asp Asp Gly Ala Val Ala
4745                4750                4755

Asn Ser Val Asp Ala Asn Glu Val Arg Ala Arg Val Thr Asp Asn
4760                4765                4770

Gln Gly Asn Ala Ile Ala Gly Tyr Ser Val Thr Phe Ala Ser Gln
4775                4780                4785

Asn Gly Ala Thr Ile Thr Thr Ser Gly Ile Thr Gly Val Asp Gly
4790                4795                4800

Trp Ala Ser Ala Lys Leu Thr His Thr Lys Ala Gly Glu Ser Gly
4805                4810                4815

Ile Leu Ala Arg Ile Ser Arg Pro Gly Ser Met Val Gln Val Leu
4820                4825                4830

Thr Pro Tyr Phe Ile Ala Asp Val Ser Thr Ala Thr Leu Gln Leu
4835                4840                4845

Phe Asn Phe Asn Pro Ile Pro Ile Ile Ala Asp Gly Val Met Gln
4850                4855                4860

Phe Phe Val Leu Gly Arg Val Phe Asp Ala Asn Gln Asn Pro Val
4865                4870                4875

Gly Gly Gln Gln Val Ala Phe Ser Ala Thr Asn Glu Val Thr Leu
4880                4885                4890

Thr Glu Ser Asn Gly Ser Ile Ser Thr Pro Glu Gly Ser Val Leu
4895                4900                4905

Leu Ser Val Thr Ser Thr Gln Ala Gly Val His Pro Ile Thr Gly
4910                4915                4920

Thr Leu Val Ser Asn Asn Tyr Thr Asp Thr Phe Gly Ala Thr Phe
4925                4930                4935

Ile Ala Asn Lys Asn Thr Ala Gln Leu Ser Thr Leu Met Val Val
4940                4945                4950

Asp Asn Asn Ala Leu Ala Asp Gly Val Thr Arg Asn Gln Val Arg
4955                4960                4965

Ala His Val Val Asp Ser Thr Gly Asn Ser Val Ala Asp Ile Ala
4970                4975                4980

Val Thr Phe Thr Ala Asn His Gly Ala Gln Leu Ser His Val Thr
4985                4990                4995

Val Leu Thr Asp Asp Asn Gly Asp Ala Val Asn Thr Leu Thr Asn
5000                5005                5010

Ser Leu Val Gly Val Thr Val Val Thr Ala Lys Leu Gly Thr Ala
5015                5020                5025

Gly Thr Pro Leu Thr Val Asp Thr Val Phe Thr Ala Gly Pro Leu

-continued

| | 5030 | | | 5035 | | | 5040 | | |

Ala Thr Leu Thr Leu Val Thr Met Val Asp Asn Ala Phe Ala Asp
                5045                5050                5055

Asn Ser Ala Thr Asn Thr Val Gln Ala Thr Leu Lys Asp Ala Thr
        5060                5065                5070

Gly Asn Pro Ile Val Gly Glu Val Val Ala Phe Ala Ala Ser Asn
    5075                5080                5085

Gly Ala Thr Ile Thr Ala Thr Asp Gly Gly Val Ser Asn Ala Asn
5090                5095                5100

Gly Ile Val Leu Ala Thr Leu Thr Asn Gly Ala Ala Gly Val Ser
5105                5110                5115

Thr Val Thr Ala Thr Ile Glu Thr Leu Thr Ala Thr Thr Glu Thr
    5120                5125                5130

Thr Phe Ile Ala Met Lys Asn Leu Asp Val Thr Val Gly Asp Thr
        5135                5140                5145

Thr Phe Asp Gly Asp Ala Gly Phe Pro Thr Thr Gly Phe Val Gly
            5150                5155                5160

Ala Ala Phe Lys Val Asn Ser Gly Gly Asp Asn Ser Leu Tyr Asp
                5165                5170                5175

Trp Ser Ser Ala Pro Ala Leu Val Ser Val Ser Gly Glu Gly
                    5180                5185                5190

Val Val Thr Phe Asn Ala Val Phe Pro Thr Gly Thr Pro Ala Ile
        5195                5200                5205

Thr Ile Ser Ala Thr Pro Lys Gly Gly Gly Ser Pro Leu Ser Tyr
            5210                5215                5220

Ser Phe Arg Val Asn Gln Trp Phe Ile Asn Asn Asn Gly Val Ala
                5225                5230                5235

Leu Asn Arg Ala Asp Ala Ala Thr Tyr Cys Ala Asn Ala Gly Tyr
                    5240                5245                5250

Thr Thr Val Ser Ser Ser Gln Val Thr Asn Ala Ile Val Trp Gly
        5255                5260                5265

Met Gly Thr Arg Ala Met Gly Asn Leu Trp Ser Glu Trp Gly Asp
            5270                5275                5280

Phe Asn Asn Tyr Asn Val Pro Gly Trp Glu Pro Ala Glu Phe Phe
                5285                5290                5295

Trp Leu Ser Asp Asn Tyr Asn Ala Thr Asp Gly Leu Ala Ala Ser
                    5300                5305                5310

Leu Ser His Gly Val Leu Thr Thr Met Gly Asp Pro Met Ala Met
        5315                5320                5325

Ile His Val Met Cys Thr Arg Pro Ile
            5330                5335

<210> SEQ ID NO 5
<211> LENGTH: 1920
<212> TYPE: PRT
<213> ORGANISM: Yersinia pseudotuberculosis
<220> FEATURE:
<221> NAME/KEY: InvD YPK_1315
<222> LOCATION: (1)..(1920)

<400> SEQUENCE: 5

Met Ile Lys Tyr Phe Ser Phe Phe Lys Lys Pro Glu Pro Ile Val Gly
1               5                   10                  15

Ile Leu Pro Asn Arg Gln Ser His Ile Leu Pro Thr His Ile Arg
            20                  25                  30

```
Arg Val Ala Trp Gly Thr Leu Leu Leu Gln Leu Phe Ile Pro Leu Ser
         35                  40                  45

Val Ser Phe Ser Pro Ala Ile Ala Ala Met Lys Ala Ser Lys Ala Asp
 50                  55                  60

Thr Met Val Ser Tyr Ser Ser Thr Glu Pro Tyr Val Leu Gly Ser Gly
 65                  70                  75                  80

Glu Thr Val Ala Met Val Ala Lys Lys Tyr Gly Ile Thr Val Asp Glu
                 85                  90                  95

Leu Lys Lys Ile Asn Ile Tyr Arg Thr Phe Ser Arg Pro Phe Thr Ala
                100                 105                 110

Leu Thr Thr Gly Asp Glu Ile Asp Ile Pro Arg Lys Ala Ser Pro Phe
        115                 120                 125

Ser Val Asp Asn Asn Lys Asp Asn Arg Leu Ser Val Glu Asn Thr Leu
130                 135                 140

Ala Gly His Ala Val Ala Gly Ala Thr Ala Leu Ser Asn Gly Asp Val
145                 150                 155                 160

Ala Lys Ser Gly Glu Arg Met Val Arg Ser Ala Ala Ser Asn Glu Phe
                165                 170                 175

Asn Asn Ser Ala Gln Gln Trp Leu Ser Gln Phe Gly Thr Ala Arg Val
            180                 185                 190

Gln Leu Asn Ile Asn Asp Asp Phe His Leu Asp Gly Ser Ala Ala Asp
        195                 200                 205

Val Leu Ile Pro Leu Tyr Asp Asn Glu Lys Ser Ile Leu Phe Thr Gln
        210                 215                 220

Leu Gly Ala Arg Asn Lys Asp Ser Arg Asn Thr Val Asn Met Gly Ala
225                 230                 235                 240

Gly Val Arg Thr Phe Gln Gly Asn Trp Met Tyr Gly Ala Asn Thr Phe
                245                 250                 255

Phe Asp Asn Asp Leu Thr Gly Lys Asn Arg Arg Ile Gly Val Gly Ala
            260                 265                 270

Glu Ala Trp Thr Asp Tyr Leu Lys Leu Ser Ala Asn Asn Tyr Phe Gly
        275                 280                 285

Ile Thr Asp Trp His Gln Ser Arg Asp Phe Ile Asp Tyr Asn Glu Arg
        290                 295                 300

Pro Ala Asn Gly Tyr Asp Leu Arg Ala Glu Ala Tyr Leu Pro Ser Tyr
305                 310                 315                 320

Pro Gln Leu Gly Gly Lys Ala Met Tyr Glu Lys Tyr Arg Gly Asp Asp
                325                 330                 335

Val Ala Leu Phe Gly Lys Asp Asn Arg Gln Lys Asn Pro His Ala Ile
            340                 345                 350

Thr Ala Gly Val Asn Tyr Thr Pro Ile Pro Leu Val Thr Ile Gly Ala
        355                 360                 365

Glu His Arg Ala Gly Lys Gly Gly Gln Asn Asp Ser Asn Ile Asn Phe
370                 375                 380

Gln Leu Asn Tyr Arg Leu Gly Glu Thr Trp Gln Ser His Ile Asp Pro
385                 390                 395                 400

Ser Ala Val Ala Ala Ser Arg Thr Leu Ala Gly Ser Arg Tyr Asp Leu
                405                 410                 415

Val Glu Arg Asn Asn His Ile Val Leu Asp Tyr Gln Lys Gln Asn Leu
            420                 425                 430

Val Arg Leu Ser Leu Pro Asp Ser Leu Ala Gly Asp Pro Phe Ser Gln
        435                 440                 445

Leu Ser Val Thr Ala Gln Val Thr Ala Thr His Gly Leu Glu Arg Ile
```

-continued

```
            450                 455                 460
Asp Trp Gln Ser Ala Glu Leu Met Ala Ala Gly Gly Val Leu Lys Gln
465                 470                 475                 480

Thr Ser Lys Asn Gly Leu Glu Ile Thr Leu Pro Glu Tyr Gln Met Asn
                485                 490                 495

Arg Thr Gly Gly Asn Ser Tyr Ile Leu Asn Ala Ile Ala Tyr Asp Thr
                500                 505                 510

Gln Gly Asn Ala Ser Ser Gln Ala Ser Met Leu Ile Thr Val Asn Ala
                515                 520                 525

Gln Lys Ile Asn Ile Ala Asn Ser Thr Leu Val Ala Val Pro Ile Asn
                530                 535                 540

Ile Glu Ala Asn Asn Ser Asp Thr Ser Val Val Thr Leu Thr Leu Lys
545                 550                 555                 560

Asp Asp Asn Asn Ile Pro Val Thr Gly Gln Asp Val Thr Phe Leu Ser
                565                 570                 575

Pro Leu Gly Thr Leu Ser Ala Met Thr Asp Ser Gly Asn Gly Val Tyr
                580                 585                 590

Thr Ala Thr Leu Thr Ala Gly Thr Val Ser Gly Thr Thr Ala Val Ser
                595                 600                 605

Ser Asn Ile Asn Gly Ser Ala Leu Asp Met Thr Pro Ala Thr Val Thr
                610                 615                 620

Leu Asn Gly Asn Ser Gly Glu Leu Ser Ile Thr His Ser Met Leu Val
625                 630                 635                 640

Ala Ala Pro Val Asn Ile Glu Ala Asn Gly Ser Asp Thr Ser Val Val
                645                 650                 655

Thr Leu Thr Leu Arg Asp Ser Asn Asn Asn Pro Val Thr Gly Gln Thr
                660                 665                 670

Val Thr Phe Ala Gly Thr Leu Gly Thr Leu Gly Ala Val Thr Glu Gly
                675                 680                 685

Ser Ser Gly Val Tyr Thr Ala Thr Leu Thr Ala Gly Ile Met Val Gly
                690                 695                 700

Thr Ser Ser Ile Thr Ala Ser Val Asn Ser Thr Ala Leu Gly Val Thr
705                 710                 715                 720

Pro Ala Thr Val Thr Leu Asn Gly Asp Ser Gly Asn Leu Ser Thr Thr
                725                 730                 735

Asn Ser Thr Leu Val Ala Ala Pro Val Asn Ile Glu Ala Asn Ser Ser
                740                 745                 750

Asp Thr Ser Val Val Thr Leu Thr Leu Arg Asp Asn Asn Asn Pro
                755                 760                 765

Val Thr Gly Gln Thr Val Val Phe Thr Ser Thr Leu Gly Thr Leu Gly
                770                 775                 780

Asn Val Thr Glu Gln Ala Ser Gly Val Tyr Thr Ala Thr Leu Thr Ala
785                 790                 795                 800

Gly Thr Val Ser Gly Val Ala Ser Leu Ser Val Ser Val Gly Gly Asn
                805                 810                 815

Ala Leu Gly Val Thr Pro Ala Thr Val Thr Leu Asn Gly Asp Ser Gly
                820                 825                 830

Asn Leu Ser Thr Thr Asn Ser Thr Leu Val Ala Ala Pro Val Asn Ile
                835                 840                 845

Glu Ala Asn Ser Ser Asp Thr Ser Val Val Thr Leu Thr Leu Arg Asp
                850                 855                 860

Asn Asn Asn Asn Pro Val Thr Gly Gln Thr Val Asn Phe Ala Gly Thr
865                 870                 875                 880
```

-continued

Leu Gly Thr Leu Gly Thr Val Ser Glu Gly Ser Ser Val Tyr Thr
            885                 890                 895

Thr Thr Leu Thr Ala Gly Thr Val Ala Gly Val Ala Ser Leu Ser Val
            900                 905                 910

Asn Val Gly Gly Asn Ala Leu Gly Val Thr Pro Ala Thr Val Thr Leu
            915                 920                 925

Asn Gly Asn Ser Gly Asn Leu Ser Ala Thr Asn Ser Thr Leu Val Ala
            930                 935                 940

Ala Pro Val Asn Ile Glu Ala Asn Ser Ser Asp Thr Ser Val Val Thr
945                 950                 955                 960

Leu Thr Leu Arg Asp Asn Asn Asn Pro Val Thr Gly Gln Thr Val
            965                 970                 975

Ala Phe Thr Ser Thr Leu Gly Thr Leu Gly Asn Val Thr Glu Gln Ala
            980                 985                 990

Ser Gly Val Tyr Thr Ala Thr Leu Thr Ala Gly Thr Val Ser Gly Val
            995                 1000                1005

Ala Ser Leu Ser Val Ser Val Asn Ser Asn Ala Leu Gly Val Thr
            1010                1015                1020

Pro Ala Thr Val Thr Leu Asn Gly Asp Ser Gly Asn Leu Ser Thr
            1025                1030                1035

Thr Asn Ser Thr Leu Val Ala Ala Pro Val Asn Ile Glu Ala Asn
            1040                1045                1050

Ser Ser Asp Thr Ser Val Val Thr Leu Thr Leu Arg Asp Asn Asn
            1055                1060                1065

Asn Asn Pro Val Thr Gly Gln Thr Val Ala Phe Thr Ser Thr Leu
            1070                1075                1080

Gly Thr Leu Gly Asn Val Thr Glu Gln Ala Ser Gly Leu Tyr Thr
            1085                1090                1095

Ala Thr Leu Thr Ala Gly Thr Val Ser Gly Val Ala Ser Leu Ser
            1100                1105                1110

Val Asn Val Gly Gly Asn Ala Leu Gly Val Thr Pro Ala Thr Val
            1115                1120                1125

Thr Leu Asn Gly Asp Ser Gly Asn Leu Ser Ala Thr Asn Ser Thr
            1130                1135                1140

Leu Val Ala Ala Pro Val Asn Ile Glu Ala Asn Ser Ser Asp Thr
            1145                1150                1155

Ser Val Val Thr Leu Thr Leu Arg Asp Asn Asn Asn Asn Pro Val
            1160                1165                1170

Thr Gly Gln Thr Val Ala Phe Thr Ser Thr Leu Gly Thr Leu Gly
            1175                1180                1185

Asn Val Thr Glu Gln Ala Ser Gly Leu Tyr Thr Ala Thr Leu Thr
            1190                1195                1200

Ala Gly Thr Val Ser Gly Val Ala Ser Leu Ser Val Asn Val Gly
            1205                1210                1215

Gly Thr Ala Leu Gly Val Thr Pro Ala Thr Val Thr Leu Asn Gly
            1220                1225                1230

Asp Ser Gly Asn Leu Ser Thr Thr Asn Ser Thr Leu Val Ala Ala
            1235                1240                1245

Pro Val Asn Ile Glu Ala Asn Ser Ser Asp Thr Ser Val Val Thr
            1250                1255                1260

Leu Thr Leu Arg Asp Asn Asn Asn Asn Pro Val Thr Gly Gln Thr
            1265                1270                1275

```
Val Ala Phe Thr Ser Thr Leu Gly Thr Leu Gly Asn Val Thr Glu
    1280                1285                1290

Gln Ala Ser Gly Leu Tyr Thr Ala Thr Leu Thr Ala Gly Thr Val
    1295                1300                1305

Ser Gly Val Ala Ser Leu Ser Val Ser Val Asn Ser Thr Ala Leu
    1310                1315                1320

Gly Val Thr Pro Ala Thr Val Thr Leu Asn Gly Asp Ser Gly Asn
    1325                1330                1335

Leu Ser Thr Thr Asn Ser Thr Leu Val Ala Ala Pro Val Asn Ile
    1340                1345                1350

Glu Ala Asn Ser Ser Asp Thr Ser Val Val Thr Leu Thr Leu Arg
    1355                1360                1365

Asp Asn Asn Asn Pro Val Thr Gly Gln Thr Val Ala Phe Thr
    1370                1375                1380

Ser Thr Leu Gly Thr Leu Gly Asn Val Thr Glu Gln Ala Ser Gly
    1385                1390                1395

Val Tyr Thr Ala Thr Leu Thr Ala Gly Thr Val Ala Gly Val Ala
    1400                1405                1410

Ser Leu Ser Val Asn Val Gly Gly Asn Ala Leu Gly Val Thr Pro
    1415                1420                1425

Ala Thr Val Thr Leu Asn Gly Asp Ser Gly Asn Leu Ser Thr Thr
    1430                1435                1440

Asn Ser Thr Leu Val Ala Ala Pro Val Asn Ile Glu Ala Asn Ser
    1445                1450                1455

Ser Asp Thr Ser Val Val Thr Leu Thr Leu Arg Asp Asn Asn Asn
    1460                1465                1470

Asn Pro Val Thr Gly Gln Thr Val Ala Phe Thr Ser Thr Leu Gly
    1475                1480                1485

Thr Leu Gly Asn Val Thr Glu Gln Ala Ser Gly Val Tyr Thr Ala
    1490                1495                1500

Thr Leu Thr Ala Gly Thr Val Ser Gly Val Ala Ser Leu Ser Val
    1505                1510                1515

Ser Val Gly Ser Ser Ala Leu Gly Val Thr Pro Ala Thr Val Thr
    1520                1525                1530

Leu Asn Gly Asp Ser Gly Asn Leu Ser Thr Thr Asn Ser Thr Leu
    1535                1540                1545

Val Ala Ala Pro Val Asn Ile Glu Ala Asn Asn Ser Asp Thr Ser
    1550                1555                1560

Val Val Thr Leu Thr Leu Arg Asp Asn Asn Asn Pro Val Thr
    1565                1570                1575

Gly Gln Thr Val Ala Phe Thr Ser Thr Leu Gly Thr Leu Gly Asn
    1580                1585                1590

Val Thr Glu Gln Ala Ser Gly Val Tyr Thr Ala Thr Leu Thr Ala
    1595                1600                1605

Gly Thr Val Ser Gly Val Ala Ser Leu Ser Val Ser Val Asn Ser
    1610                1615                1620

Asn Ala Leu Gly Val Thr Pro Ala Thr Val Thr Leu Asn Gly Asp
    1625                1630                1635

Ser Gly Asn Leu Ser Thr Thr Asn Ser Thr Leu Val Ala Ala Pro
    1640                1645                1650

Val Asn Ile Glu Ala Asn Ser Ser Asp Thr Ser Val Val Thr Leu
    1655                1660                1665

Thr Leu Arg Asp Asn Asn Asn Asn Pro Val Thr Gly Gln Thr Val
```

```
                1670                1675                1680

Val Phe Thr Ser Thr Leu Gly Thr Leu Gly Asn Val Thr Glu Gln
            1685                1690                1695

Ala Ser Gly Leu Tyr Thr Ala Thr Leu Thr Ala Gly Thr Val Ser
        1700                1705                1710

Gly Val Ala Ser Leu Ser Val Ser Val Gly Gly Asn Ala Leu Gly
    1715                1720                1725

Val Thr Gly Asn Ile Thr Leu Ala Pro Gly Ala Leu Asp Ala Ala
1730                1735                1740

Arg Ser Ile Leu Ala Val Asn Lys Pro Ser Ile Asn Ala Asp Asp
    1745                1750                1755

Arg Ile Gly Ser Thr Ile Thr Phe Thr Ala Gln Asp Ala Gln Gly
        1760                1765                1770

Asn Ala Ile Thr Gly Leu Asp Ile Ala Phe Met Thr Asp Leu Glu
            1775                1780                1785

Asn Ser Gln Ile Met Thr Leu Val Asp His Asn Asp Gly Thr Tyr
                1790                1795                1800

Thr Ala Asn Ile Asn Gly Thr Gln Thr Gly Ile Ala Asn Ile Ala
                    1805                1810                1815

Val Gln Ser Ser Gly Ala Thr Ile Ala Gly Leu Ala Ala Thr Met
                        1820                1825                1830

Val Thr Ile Thr Pro Gly Ala Trp Asn Thr Thr Gln Ala Thr Pro
                            1835                1840                1845

Val Met Thr Val Ala Leu Pro Ile Thr Thr Cys Gln Ser Ser Ser
                                1850                1855                1860

Gly Val Tyr Lys Arg Tyr Tyr Ile Gly Ile Val Thr His Glu Leu
                                    1865                1870                1875

Tyr Asp Asn Tyr Gly Asn Glu Ile Ser Gly Ile Leu Thr Tyr Asn
                                        1880                1885                1890

Leu Gly Ala Gly Arg Tyr Thr Thr Val Thr Ser Gln Asn Ser Ser
                                            1895                1900                1905

Val Ser Gly Ser Asn Gly Leu Thr Arg Arg Ser Asn
                                                1910                1915                1920

<210> SEQ ID NO 6
<211> LENGTH: 835
<212> TYPE: PRT
<213> ORGANISM: Yersinia enterocolitica
<220> FEATURE:
<221> NAME/KEY: InvA YE2564
<222> LOCATION: (1)..(835)

<400> SEQUENCE: 6

Met Tyr Ser Phe Phe Asn Thr Leu Thr Val Thr Lys Ile Ile Ser Arg
1               5                   10                  15

Leu Ile Leu Ser Ile Gly Leu Ile Phe Gly Ile Phe Thr Tyr Gly Phe
                    20                  25                  30

Ser Gln Gln His Tyr Phe Asn Ser Glu Ala Leu Glu Asn Pro Ala Glu
                35                  40                  45

His Asn Glu Ala Phe Asn Lys Ile Ile Ser Thr Gly Thr Ser Leu Ala
            50                  55                  60

Val Ser Gly Asn Ala Ser Asn Ile Thr Arg Ser Met Val Asn Asp Ala
65                  70                  75                  80

Ala Asn Gln Glu Val Lys His Trp Leu Asn Arg Phe Gly Thr Thr Gln
                    85                  90                  95
```

-continued

```
Val Asn Val Asn Phe Asp Lys Lys Phe Ser Leu Lys Glu Ser Ser Leu
            100                 105                 110

Asp Trp Leu Leu Pro Trp Tyr Asp Ser Ala Ser Tyr Val Phe Phe Ser
        115                 120                 125

Gln Leu Gly Ile Arg Asn Lys Asp Ser Arg Asn Thr Leu Asn Ile Gly
    130                 135                 140

Ala Gly Val Arg Thr Phe Gln Gln Ser Trp Met Tyr Gly Phe Asn Thr
145                 150                 155                 160

Phe Tyr Asp Asn Asp Met Thr Gly His Asn His Arg Ile Gly Val Gly
                165                 170                 175

Ala Glu Ala Trp Thr Asp Tyr Leu Gln Leu Ser Ala Asn Gly Tyr Phe
            180                 185                 190

Arg Leu Asn Gly Trp His Gln Ser Arg Asp Phe Ala Asp Tyr Asn Glu
        195                 200                 205

Arg Pro Ala Ser Gly Gly Asp Ile His Val Lys Ala Tyr Leu Pro Ala
    210                 215                 220

Leu Pro Gln Leu Gly Gly Lys Leu Lys Tyr Glu Gln Tyr Arg Gly Glu
225                 230                 235                 240

Arg Val Ala Leu Phe Gly Lys Asp Asn Leu Gln Ser Asn Pro Tyr Ala
                245                 250                 255

Val Thr Thr Gly Leu Ile Tyr Thr Pro Ile Pro Phe Ile Thr Leu Gly
            260                 265                 270

Val Asp Gln Arg Met Gly Lys Ser Arg Gln His Glu Ile Gln Trp Asn
        275                 280                 285

Leu Gln Met Asp Tyr Arg Leu Gly Glu Ser Phe Arg Ser Gln Phe Ser
    290                 295                 300

Pro Ala Val Val Ala Gly Thr Arg Leu Leu Ala Glu Ser Arg Tyr Asn
305                 310                 315                 320

Leu Val Glu Arg Asn Pro Asn Ile Val Leu Glu Tyr Gln Lys Gln Asn
                325                 330                 335

Thr Ile Lys Leu Ala Phe Ser Pro Ala Val Leu Ser Gly Leu Pro Gly
            340                 345                 350

Gln Val Tyr Ser Val Ser Ala Gln Ile Gln Ser Gln Ser Ala Leu Gln
        355                 360                 365

Arg Ile Leu Trp Asn Asp Ala Gln Trp Val Ala Ala Gly Gly Lys Leu
    370                 375                 380

Ile Pro Val Ser Ala Thr Asp Tyr Asn Val Val Leu Pro Pro Tyr Lys
385                 390                 395                 400

Pro Met Ala Pro Ala Ser Arg Thr Val Gly Lys Thr Gly Glu Ser Glu
                405                 410                 415

Ala Ala Val Asn Thr Tyr Thr Leu Ser Ala Thr Ala Ile Asp Asn His
            420                 425                 430

Gly Asn Ser Ser Asn Pro Ala Thr Leu Thr Val Ile Val Gln Gln Pro
        435                 440                 445

Gln Phe Val Ile Thr Ser Glu Val Thr Asp Gly Ala Leu Ala Asp
    450                 455                 460

Gly Arg Thr Pro Ile Thr Val Lys Phe Thr Val Thr Asn Ile Asp Ser
465                 470                 475                 480

Thr Pro Val Ala Glu Gln Glu Gly Val Ile Thr Thr Ser Asn Gly Ala
                485                 490                 495

Leu Pro Ser Lys Val Thr Lys Lys Thr Asp Ala Gln Gly Val Ile Ser
            500                 505                 510

Ile Ala Leu Thr Ser Phe Thr Val Gly Val Ser Val Val Thr Leu Asp
```

```
        515                 520                 525

Ile Gln Gly Gln Gln Ala Thr Val Asp Val Arg Phe Ala Val Leu Pro
    530                 535                 540

Pro Asp Val Thr Asn Ser Ser Phe Asn Val Ser Pro Ser Asp Ile Val
545                 550                 555                 560

Ala Asp Gly Ser Met Gln Ser Ile Leu Thr Phe Val Pro Arg Asn Lys
                565                 570                 575

Asn Asn Glu Phe Val Ser Gly Ile Thr Asp Leu Glu Phe Ile Gln Ser
            580                 585                 590

Gly Val Pro Val Thr Ile Ser Ser Val Thr Glu Asn Ala Asp Asn Tyr
        595                 600                 605

Thr Ala Ser Val Val Gly Asn Ser Val Gly Asp Val Asp Ile Thr Pro
    610                 615                 620

Gln Val Gly Gly Glu Ser Leu Asp Leu Leu Gln Lys Arg Ile Thr Leu
625                 630                 635                 640

Tyr Pro Val Pro Lys Ile Thr Gly Ile Lys Val Asn Gly Glu Gln Phe
                645                 650                 655

Ala Thr Asp Lys Gly Phe Pro Lys Thr Thr Phe Asn Lys Ala Thr Phe
            660                 665                 670

Gln Leu Val Met Asn Asp Asp Val Ala Asn Asn Thr Gln Tyr Asp Trp
        675                 680                 685

Thr Ser Ser Tyr Ala Ala Ser Ala Pro Val Asp Asn Gln Gly Lys Val
    690                 695                 700

Asn Ile Ala Tyr Lys Thr Tyr Gly Ser Thr Val Thr Val Thr Ala Lys
705                 710                 715                 720

Ser Lys Lys Phe Pro Ser Tyr Thr Ala Thr Tyr Gln Phe Lys Pro Asn
                725                 730                 735

Leu Trp Val Phe Ser Gly Thr Met Ser Leu Gln Ser Ser Val Glu Ala
            740                 745                 750

Ser Arg Asn Cys Gln Arg Thr Asp Phe Thr Ala Leu Ile Glu Ser Ala
        755                 760                 765

Arg Ala Ser Asn Gly Ser Arg Ser Pro Asp Gly Thr Leu Trp Gly Glu
    770                 775                 780

Trp Gly Ser Leu Ala Thr Tyr Asp Ser Ala Glu Trp Pro Ser Gly Asn
785                 790                 795                 800

Tyr Trp Thr Lys Lys Thr Ser Thr Asp Phe Val Thr Met Asp Met Thr
                805                 810                 815

Thr Gly Asp Ile Pro Thr Ser Ala Ala Thr Ala Tyr Pro Leu Cys Ala
            820                 825                 830

Glu Pro Gln
        835

<210> SEQ ID NO 7
<211> LENGTH: 2484
<212> TYPE: PRT
<213> ORGANISM: Yersinia enterocolitica
<220> FEATURE:
<221> NAME/KEY: InvE YE0694
<222> LOCATION: (01)..(2484)

<400> SEQUENCE: 7

Met Gly Ser Ile Phe Lys Gly Ile Glu Arg Tyr Leu Cys Ala Gly Phe
1               5                   10                  15

Met Lys Lys Ala Ile Ala Tyr Thr Gln Ile Ile Leu Gln Ile Leu Leu
            20                  25                  30
```

Gly Thr Leu Pro Leu Tyr Ser Met Ser Phe Ser Thr Gln Ala Asn Ser
         35                  40                  45

Asp Ile Thr Lys Lys Thr Val Leu Phe Lys Gln Leu His Thr Leu Thr
 50                  55                  60

Pro Thr Asp Thr Leu Glu Ser Val Ala Ala Ser Tyr Gly Leu Ser Val
 65                  70                  75                  80

Asp Glu Leu Trp Ala Leu Asn Ile Asn Leu Tyr Asn Asn Arg Ser Ala
                 85                  90                  95

Phe Asp Ala Ile Lys Tyr Gly Ala Val Tyr Val Pro Asn Gln Glu
                100                 105                 110

Glu Glu Gln Gln Ala Ala Gln Ala Ser Leu Val Ala Ser His Leu
                115                 120                 125

Ser Gln Val Gly Asn Ser Leu Ser Ser Glu Asn Arg Val Asp Ala Phe
 130                 135                 140

Ser Arg Leu Ala Lys Gly Ile Leu Leu Ser Ser Thr Ala Lys Thr Val
 145                 150                 155                 160

Glu Glu Trp Leu Gly His Ile Gly Gln Ala Gln Val Lys Leu Gln Thr
                 165                 170                 175

Asp Asp Lys Asn Asp Phe Ser Gly Ser Glu Ile Asp Leu Phe Ile Pro
                180                 185                 190

Leu Tyr Asp Gln Pro Glu Lys Leu Ala Phe Ser Gln Phe Gly Phe Arg
                195                 200                 205

Arg Ile Asp Gln Arg Asn Ile Met Asn Ile Gly Leu Gly Gln Arg His
                210                 215                 220

Tyr Val Ser Asp Trp Met Phe Gly Tyr Asn Ile Phe Phe Asp Gln Gln
225                 230                 235                 240

Val Ser Gly Asn Ala His Arg Arg Val Gly Phe Gly Gly Glu Leu Ala
                245                 250                 255

Arg Asp Tyr Ile Lys Leu Ser Ala Asn Ser Tyr His Arg Leu Gly Gly
                260                 265                 270

Trp Lys Asn Ser Thr Arg Leu Glu Asp Tyr Asp Glu Arg Ala Ala Asn
                275                 280                 285

Gly Tyr Asp Ile Arg Thr Glu Ala Tyr Leu Pro His Tyr Pro Gln Leu
290                 295                 300

Gly Gly Lys Leu Met Tyr Glu Gln Tyr Phe Gly Asp Glu Val Ala Leu
305                 310                 315                 320

Phe Gly Ile Asn Glu Arg Gln Lys Asn Pro Ser Ala Leu Thr Ala Gly
                325                 330                 335

Val Ser Tyr Thr Pro Ile Pro Leu Val Ser Leu Gly Leu Asp His Thr
                340                 345                 350

Ile Gly Asn Gly Gly Lys Lys Thr Gly Val Asn Val Ala Val Asn
                355                 360                 365

Tyr Glu Ile Asn Thr Pro Trp Gln Gln Gln Ile Asp Pro Ala Ala Val
370                 375                 380

Gln Thr Thr Arg Thr Leu Ala Gly Arg Met Asp Leu Val Asp Arg
385                 390                 395                 400

Asn Asn Asn Ile Val Leu Glu Tyr Arg Lys Gln Val Val Thr Leu
                405                 410                 415

Asn Leu Pro Glu Lys Val Ser Gly Lys Glu Lys Gln Val Val Pro Ile
                420                 425                 430

Asn Tyr Thr Phe Asn Ala Arg His Gly Leu Asp Arg Ile Glu Trp Asp
                435                 440                 445

Ala Ala Asp Val Ile Lys Ala Gly Gly Gln Val Ile Asn Gln Gly Asn

```
                450              455              460
Leu Ala Tyr Tyr Ile Ala Met Pro Pro Tyr Ile Asp Gly Ala Val Asn
465                      470                  475                  480

Ala Tyr Val Leu Ser Gly Arg Ala Ile Asp Lys Lys Gly Asn Tyr Ser
                    485                  490                  495

Val Ser Gly Ser Thr Asn Val Tyr Val Thr Gly Val Asn Ile Asn Arg
                500                  505                  510

Ile Asn Ser Thr Ile Ser Leu Asn Pro Ala Thr Leu Pro Ala Asn Gly
            515                  520                  525

Thr Ser Arg Ser Thr Ile Gln Leu Lys Leu Asn Thr Asp Ala Gly Gln
        530                  535                  540

Ala Val Ser Gly Ala Ser Gly Gln Met Thr Phe Ala Ile Arg Asp Ser
545                  550                  555                  560

Ser Gly Arg Val Phe Lys Ala Arg Thr Ser Leu Gln Pro Val Val Ile
                565                  570                  575

Ser Asp Val Gln Glu Val Gln Thr Gly Val Tyr Glu Ala Ser Ile Thr
                580                  585                  590

Ser Gly Phe Leu Thr Gly Arg Phe Glu Ile Thr Pro Thr Val Arg Gly
            595                  600                  605

Val Gln Leu Asn Pro Ile Ile Leu Thr Gln Ser Ala Asp Lys Thr Thr
        610                  615                  620

Ala Thr Ile Thr Asp Ser Ser Ala Val Thr Ile Ser Thr Pro Ser Ile
625                  630                  635                  640

Thr Thr Asn Ala Thr Asp Lys Thr Lys Leu Glu Val Gln Val Thr Asp
                645                  650                  655

Ala Leu Gly His Pro Val Pro Gly Val Glu Val Thr Trp Val Ser Asp
                660                  665                  670

Leu Asn Ser Pro Gly Leu Glu Tyr Val Thr Ser Ile Thr Asn Glu His
            675                  680                  685

Gly Ile Ala Glu Asn Asn Phe Ser Ser Thr Val Thr Gly Thr Ala Asn
        690                  695                  700

Ile Thr Val Gln Val Gly Thr Ser Ala Pro Val Gln Ala Gly Lys Ile
705                  710                  715                  720

Glu Ile Lys Ala Asp Asn Ser Thr Met Thr Val Asn Ala Ser Asp Phe
                725                  730                  735

Thr Val Thr Thr Thr Pro Val Val Ala Asn Gly Thr Ser Lys Ala Val
                740                  745                  750

Tyr Lys Leu Lys Val Met Asp Lys Gln Gly Asn Val Val Pro Gly Ala
            755                  760                  765

Ala Val Asp Trp Leu Ser Asn Ile Gly Thr Phe Val Gln Gly Ser Thr
        770                  775                  780

Thr Thr Thr Asp Thr Asn Gly Glu Thr Phe Ile Glu Leu Val Ser Thr
785                  790                  795                  800

Lys Ala Glu Thr Ala Lys Val Thr Ala Thr Val Gly Gly Lys Pro Tyr
                805                  810                  815

Asn Ala Gly Lys Val Val Phe Val Ala Asp Arg Gln Ser Gly Lys Ile
                820                  825                  830

Thr Leu Leu Pro Val Ser Lys Asn Thr Ala Ala Asn Gly Thr Asp
            835                  840                  845

Ser Ile Thr Leu Asn Ala Lys Ile Leu Asp Ala Asn Gly Asn Pro Ile
        850                  855                  860

Lys Asn Glu Glu Ile Glu Trp Asp Ala Ala Ser His Lys Val Thr Phe
865                  870                  875                  880
```

```
Ser Pro Ala Thr Gly Lys Thr Gln Thr Asn Asp Leu Gly Glu Thr Gln
            885                 890                 895

Ile Thr Leu Thr Ser Thr Asp Val Gly Asp Ile Thr Leu Asn Ala Gln
            900                 905                 910

Val Val Lys Asn Asn Leu Leu Val Asn Gln Ala Gly Glu Lys Leu Ser
            915                 920                 925

Phe Thr Ala Asp Thr Val Thr Ala Asn Ile Ser Ala Trp Ser Ala Pro
            930                 935                 940

Ser Val Lys Thr Leu Ile Ala Asp Gly Gln Ala Gln Val Ile Tyr Lys
945                 950                 955                 960

Val Val Val Lys Asp Lys Asn Gly His Val Val Pro Asn Ser Pro Val
            965                 970                 975

Leu Trp Glu Thr Asn Leu Gly Glu Phe Val Pro Ala Gln Ala Thr Thr
            980                 985                 990

Thr Met Thr Ser Thr Asp Ser Gln Gly Glu Ala Thr Val Val Leu Ala
            995                 1000                1005

Ser Ile Lys Ala Gly Ser Ala Thr Val Lys Ala Ser Val Asn Ala
            1010                1015                1020

Asn Lys Asp Thr Ser Pro Thr Gln Val Glu Phe Thr Ala Asp Ser
            1025                1030                1035

Ser Thr Ala Thr Ile Ala Ile Thr Pro Val Thr Lys Gln Val Tyr
            1040                1045                1050

Val Ala Asn Gly Ser Glu Lys Val Thr Tyr Ala Val Thr Val Leu
            1055                1060                1065

Asp Ala Asn Asn Asn Pro Val Lys Ala Glu Ala Ile Asn Trp Lys
            1070                1075                1080

Ser Glu Asn Gly His Pro Val Lys Val Glu Pro Ala Pro Ser Gln
            1085                1090                1095

Thr Asp Gly Gln Gly Lys Ala Thr Val Ser Ile Gly Ser Val Lys
            1100                1105                1110

Ala Gly Asp Thr Gln Ile Arg Ala Thr Leu Gly Asn Asn Ala Thr
            1115                1120                1125

Ala Ile Ala Asp Ala Ile Thr Phe Glu Ala Asp Arg Gln Thr Ala
            1130                1135                1140

Val Val Lys Thr Val Glu Val Thr Gly Ser Lys Val Thr Ala Pro
            1145                1150                1155

Asp Gly Thr Gly Ser Ile Ser Tyr Val Thr Thr Val Val Asp Ala
            1160                1165                1170

Asn Gly Asn Pro Val Ser Gly Met Ile Leu Ser Trp Gly Ser Asn
            1175                1180                1185

Ile Asn Asn Val Ala Asn Pro Ser Thr Thr Thr Asp Ile Asn Gly
            1190                1195                1200

Gln Ser Ser Gln Thr Ile Thr Gly Thr Gln Ala Gly Lys Val Glu
            1205                1210                1215

Ile Ser Val Ala Leu Thr Ser Gly Asn Asn Ala Thr Asn Pro Val
            1220                1225                1230

Lys Asn Ser Asn Asn Ala Glu Phe Val Ala Val Thr Pro Val Met
            1235                1240                1245

Ala Asn Ala Asp Leu Leu Leu Gln Pro Asn Leu Ile Ile Ala Asn
            1250                1255                1260

Gly Lys Gln Thr Ala Thr Leu Lys Phe Thr Leu Arg Asp Ala Asn
            1265                1270                1275
```

```
His Asn Pro Val Ser Gly Leu Lys Gln Arg Ile Asp Val Thr Gln
    1280            1285            1290

Ser Val Ala Ser His Val Thr Ile Gly Ala Val Thr Glu Thr Thr
    1295            1300            1305

Val Lys Gly Val Tyr Gln Ala Ala Ile Thr Gly Met Lys Glu Asn
    1310            1315            1320

Ser Val Asp Leu Thr Ala Ser Val Lys Gly Thr Asn Val Arg Gln
    1325            1330            1335

Thr Arg Thr Leu Thr Leu Gln Ala Asp Asn Lys Thr Ala Thr Leu
    1340            1345            1350

Lys Thr Val Thr Ser Asn Ile Lys Thr Ala Lys Ala Asp Gly Lys
    1355            1360            1365

Glu Ser Ile Thr Tyr Arg Ala Lys Val Ile Asp Ala Gln Gly Asn
    1370            1375            1380

Ala Ser Leu Asp Asn Val Ser Val Gly Trp Arg Thr Thr Leu Gly
    1385            1390            1395

Glu Leu Ala Ala Ile Thr Lys Thr Asp Thr Ser Gly Ile Ala Thr
    1400            1405            1410

Val Thr Leu Thr Ser Lys Gln Ala Gly Ser Ala Thr Val Thr Ala
    1415            1420            1425

Ile Val Ser Ser Thr Ser Glu Met Lys Ala Ala Pro Val Asn Phe
    1430            1435            1440

Thr Ala Gly Gly Ile Ser Ile Thr Gln Ser Thr Ala Ser Leu Ser
    1445            1450            1455

Val Lys Asp Leu Val Ala Asp Asp Val Ile Thr Thr Lys Leu Thr
    1460            1465            1470

Val Asn Ile Lys Asp Asp Asn Gly Asn Pro Leu Thr Gly Lys Gly
    1475            1480            1485

Ser Glu Ile Ser Val Thr Ala Thr Gly Leu Ala Gly Leu Lys Leu
    1490            1495            1500

Pro Thr Thr Phe Val Glu Gly Pro Asn Gly Val Tyr Thr Ala Thr
    1505            1510            1515

Ile Thr Gly Thr Lys Ala Gly Val Gly Asp Ile Val Thr Ala Leu
    1520            1525            1530

Ala Gly Lys Glu Leu Ala Lys Gln Gln Leu Lys Val Ile Ala Asp
    1535            1540            1545

Val Gln Thr Ala Lys Ile Ala Asp Ile Lys Pro Leu Lys Ser Gly
    1550            1555            1560

Ser Val Ser Val Gly Asp Lys Val Thr Tyr Gln Ala Thr Leu Lys
    1565            1570            1575

Asp Ala Asn Asp Asn Leu Leu Gly Ala Gly Ile Pro Val His Trp
    1580            1585            1590

Ser Val Asn Arg Asp Thr Leu Met Ser Gly Lys Leu Ile Ser Leu
    1595            1600            1605

Thr Asn Ser Ala Gly Val Ala Glu Val Glu Ile Ser Arg Asp Leu
    1610            1615            1620

Ala Gly Asp Ala Leu Val Thr Ala Ala Val Gly Asn Asn Ser Leu
    1625            1630            1635

Gln Ala Thr Ala Val Lys Phe Ile Ser Gly Gly Val Asp Ile Ser
    1640            1645            1650

Lys Ser Ser Met Gln Leu Leu Gln Gly Asn Ile Thr Ala Asp Asn
    1655            1660            1665

Leu Asp Ile Ala Thr Ile Gln Val Asp Ile Arg Asp Ser Lys Gly
```

```
                1670                1675                1680
Asn Pro Leu Pro Asn Leu Ala Ser Gln Ile Thr Thr Ser Pro Lys
        1685                1690                1695
Lys Gly Glu His Gly Leu Lys Ile Glu Thr Ile Ala Asn Pro Ser
        1700                1705                1710
Gly Asp Gly Tyr Leu Val Lys Met Lys Gly Thr Gln Ala Gly Asn
        1715                1720                1725
His Thr Val Thr Val Ser Val Ala Gly Lys Pro Leu Ser Ala Lys
        1730                1735                1740
Val Asp Met Val Leu Lys Gly Asp Ala Thr Thr Ala Lys Ile Glu
        1745                1750                1755
Ser Val Lys Ser Ser Ser Pro Thr Phe Lys Ala Asp Asn Val Asp
        1760                1765                1770
Thr Val Thr Tyr Thr Ala Lys Val Val Asp Ala Asn Asn Asn Leu
        1775                1780                1785
Leu Glu Asn Ile Ala Val Ser Trp Arg Leu Ala Gln Gly Glu Gly
        1790                1795                1800
Gln Tyr Gln Gly Gln Ser Tyr Thr Gly Lys Thr Gly Val Ala Thr
        1805                1810                1815
Thr Lys Leu Ser Ala Ser Arg Leu Gly Thr Tyr Lys Met Glu Ala
        1820                1825                1830
Gln Val Arg Gln Val Lys Ala Ala Ala Gly Val Asn Ser Thr
        1835                1840                1845
Ala Gly Asp Ala Asp Pro Ser Gln Ser Asp Phe Val Val Asp Val
        1850                1855                1860
Ala Ser Ile Asp Ser Ser Gly Asn Thr Lys Ala Lys Leu Thr Ala
        1865                1870                1875
Thr Leu Lys Asp Lys Phe Gly Asn Leu Leu Ser Gly Gln Lys Val
        1880                1885                1890
Lys Leu Thr Asp Ser Asn Ser Leu Lys Lys Ile Thr Leu Ser Ala
        1895                1900                1905
Asn Pro Met Lys Asp Asn Gly Asp Gly Thr Tyr Ser Thr Glu Val
        1910                1915                1920
Thr Ala Thr Ala Lys Gly Asn Thr Arg Phe Ile Ala Arg Val Asn
        1925                1930                1935
Gly Val Asp Leu Thr Gln Gln Pro Gln Ile Val Ile Gly Asn Ile
        1940                1945                1950
Ile Pro Gln Leu Ser Phe Ala Lys Ser Lys Glu Ala Thr Thr Tyr
        1955                1960                1965
Ser Arg Lys Val His Lys Pro Leu Ser Leu Thr Gly Leu Pro Ser
        1970                1975                1980
Ser Ala Thr Leu Thr Ala His Trp Ser Ser Asp Asn Ser Asp Val
        1985                1990                1995
Ala Thr Val Asn Pro Leu Asn Gly Glu Leu Thr Leu Leu Lys Ala
        2000                2005                2010
Gly Val Val Asn Ile Ser Val Leu Thr Leu Pro Thr Asp Thr Tyr
        2015                2020                2025
Thr Ser Gly Thr Ala Asn Tyr Gln Leu Thr Val Glu Lys Ala Asp
        2030                2035                2040
Pro Gly Ile Asn Phe Ala Val Ala Lys Arg Asp Val Lys Trp Met
        2045                2050                2055
Asp Ser Met Ser Pro Gln Asn Phe Val Leu Ser Asn Ser Asp Ala
        2060                2065                2070
```

```
Asn Gln Ser Asp Ile Lys Thr Ile Trp Gln Thr Asp Ser Gly Lys
    2075            2080                2085

Ile Ala Thr Val Asp Lys Gly Leu Val Thr Leu Val Lys Pro
    2090            2095                2100

Gly Thr Thr Asn Val Thr Val Ser Phe Val Gly Asp Glu Arg Phe
    2105            2110                2115

Lys Tyr Gly Glu Ala Ser Tyr Glu Leu Asn Val Ala Lys Tyr Lys
    2120            2125                2130

Pro Thr Val Ser Phe Ala Asn Ser Leu Leu Thr Asn Lys Val Ser
    2135            2140                2145

Glu Lys Ile Tyr Val Gln Lys Pro Asp Glu Lys Leu Ser Thr Tyr
    2150            2155                2160

Ala His Leu Glu Thr Lys Trp Ser Ser Ser Asp Asn Ala Ile Val
    2165            2170                2175

Glu Val Ala Asn Asp Ala Ser Tyr Met Ser Pro Lys Gly Pro Gly
    2180            2185                2190

Lys Ala Arg Ile Thr Leu Gln Val Val Gly Asn Asp Trp Tyr Glu
    2195            2200                2205

Glu Gln Ser Ser Ser Tyr Glu Gln Glu Val Tyr Ala Thr Pro Lys
    2210            2215                2220

Val Ser Ile Arg Glu Thr Thr Ala Ile Ser Asn Ser Val Lys Lys
    2225            2230                2235

Val Asn Glu Arg Val Trp Ser Pro Val Phe Thr Asn Asp Asn Phe
    2240            2245                2250

Gly Val Thr Val Asp Asn Ser Gln Ser Lys Tyr Glu Arg Ala Asp
    2255            2260                2265

Ser Val Lys Val Ile Leu Leu Asp Gly Thr Gln Glu Leu Ala Ser
    2270            2275                2280

Lys Glu Leu Gly Ile Thr Ser Ser Ser Phe Glu Phe Lys Pro
    2285            2290                2295

Lys Pro Asp Trp Val Gly Lys Ser Leu Lys Val Lys Val Val Ala
    2300            2305                2310

Lys Asn Asp Val Arg Gln Glu Asn Glu Val Thr Leu Asp His Glu
    2315            2320                2325

Val Arg Val Gly Thr Leu Glu Pro Ile Asp Ile Trp Gln Asn Ala
    2330            2335                2340

Ile Phe Thr Arg Asn Tyr Ser Leu His Asn Asn Asp Gly Ser Lys
    2345            2350                2355

Arg Asp Ser Cys Pro Ile Val Asn Asn Leu Phe Tyr Pro Asn Tyr
    2360            2365                2370

Ala Arg Leu Asn Trp Arg Met Gln Leu Val Leu Asn Lys Asp Met
    2375            2380                2385

Leu His Pro Met Gln Ile Thr Lys Leu Glu Ser Lys Thr Ser Lys
    2390            2395                2400

His Gly Ile Asn Met Thr His Ile Asp Ser Ser Thr Ser Glu Ile
    2405            2410                2415

Phe Asp Ser Tyr Asp Asn Lys Asp Asp Asn Arg Leu Ile Asn Lys
    2420            2425                2430

Cys Ile Lys Glu Lys Tyr Gly Thr Tyr Lys Thr Tyr Met Asp Ile
    2435            2440                2445

Lys Tyr Ala Gly Arg Glu Tyr Lys Tyr Glu Ala Ile Asn Asp Leu
    2450            2455                2460
```

```
Tyr Trp Glu Gly Glu Gly Asp  Asp Arg Glu Ser Asp  Lys Ser Ser
    2465            2470                 2475

Gly Phe Lys Lys Val Pro
    2480

<210> SEQ ID NO 8
<211> LENGTH: 432
<212> TYPE: PRT
<213> ORGANISM: Yersinia pseudotuberculosis
<220> FEATURE:
<221> NAME/KEY: YadA pYV0013
<222> LOCATION: (01)..(432)

<400> SEQUENCE: 8

Met Thr Lys Asp Phe Lys Ile Ser Val Ser Ala Ala Leu Ile Ser Ala
1               5                   10                  15

Leu Phe Ser Ser Pro Tyr Ala Phe Ala Glu Pro Glu Asp Gly Asn
                20                  25                  30

Asp Gly Ile Pro Arg Leu Ser Ala Val Gln Ile Ser Pro Asn Val Asp
            35                  40                  45

Pro Lys Leu Gly Val Gly Leu Tyr Pro Ala Lys Pro Ile Leu Arg Gln
    50                  55                  60

Glu Asn Pro Lys Leu Pro Pro Arg Gly Pro Gln Gly Pro Glu Lys Lys
65                  70                  75                  80

Arg Ala Arg Leu Ala Glu Ala Ile Gln Pro Gln Val Leu Gly Gly Leu
                85                  90                  95

Asp Ala Arg Ala Lys Gly Ile His Ser Ile Ala Ile Gly Ala Thr Ala
            100                 105                 110

Glu Ala Ala Lys Pro Ala Ala Val Ala Val Gly Ala Gly Ser Ile Ala
        115                 120                 125

Thr Gly Val Asn Ser Val Ala Ile Gly Pro Leu Ser Lys Ala Leu Gly
    130                 135                 140

Asp Ser Ala Val Thr Tyr Gly Ala Ser Ser Thr Ala Gln Lys Asp Gly
145                 150                 155                 160

Val Ala Ile Gly Ala Arg Ala Ser Ala Ser Asp Thr Gly Val Ala Val
                165                 170                 175

Gly Phe Asn Ser Lys Val Asp Ala Gln Asn Ser Val Ala Ile Gly His
            180                 185                 190

Ser Ser His Val Ala Ala Asp His Gly Tyr Ser Ile Ala Ile Gly Asp
        195                 200                 205

Leu Ser Lys Thr Asp Arg Glu Asn Ser Val Ser Ile Gly His Glu Ser
    210                 215                 220

Leu Asn Arg Gln Leu Thr His Leu Ala Ala Gly Thr Lys Asp Asn Asp
225                 230                 235                 240

Ala Val Asn Val Ala Gln Leu Lys Lys Glu Met Ala Glu Thr Leu Glu
                245                 250                 255

Asn Ala Arg Lys Glu Thr Leu Ala Gln Ser Asn Asp Val Leu Asp Ala
            260                 265                 270

Ala Lys Lys His Ser Asn Ser Val Ala Arg Thr Thr Leu Glu Thr Ala
        275                 280                 285

Glu Glu His Ala Asn Lys Ser Ala Glu Ala Leu Val Ser Ala Lys
    290                 295                 300

Val Tyr Ala Asp Ser Asn Ser Ser His Thr Leu Lys Thr Ala Asn Ser
305                 310                 315                 320

Tyr Thr Asp Val Thr Val Ser Ser Ser Thr Lys Lys Ala Ile Ser Glu
                325                 330                 335
```

Ser Asn Gln Tyr Thr Asp His Lys Phe Ser Gln Leu Asp Asn Arg Leu
            340                 345                 350

Asp Lys Leu Asp Lys Arg Val Asp Lys Gly Leu Ala Ser Ala Ala
            355                 360                 365

Leu Asn Ser Leu Phe Gln Pro Tyr Gly Val Gly Lys Val Asn Phe Thr
            370                 375                 380

Ala Gly Val Gly Gly Tyr Arg Ser Ser Gln Ala Leu Ala Ile Gly Ser
385                 390                 395                 400

Gly Tyr Arg Val Asn Glu Ser Val Ala Leu Lys Ala Gly Val Ala Tyr
                405                 410                 415

Ala Gly Ser Ser Asn Val Met Tyr Asn Ala Ser Phe Asn Ile Glu Trp
            420                 425                 430

<210> SEQ ID NO 9
<211> LENGTH: 422
<212> TYPE: PRT
<213> ORGANISM: Yersinia enterocolitica
<220> FEATURE:
<221> NAME/KEY: YadA Yep0066
<222> LOCATION: (1)..(422)

<400> SEQUENCE: 9

Met Thr Lys Asp Phe Lys Ile Ser Val Ser Ala Ala Leu Ile Ser Ala
1               5                   10                  15

Leu Phe Ser Ser Pro Tyr Ala Phe Ala Asn Asn Asp Glu Val His Phe
            20                  25                  30

Thr Ala Val Gln Ile Ser Pro Asn Ala Asp Pro Asp Ser His Val Val
            35                  40                  45

Ile Phe Gln Pro Ala Ala Glu Ala Leu Gly Gly Thr Asn Ala Leu Ala
    50                  55                  60

Lys Ser Ile His Ser Ile Ala Val Gly Ala Ser Ala Glu Ala Ala Lys
65                  70                  75                  80

Gln Ala Ala Val Ala Val Gly Ala Gly Ser Ile Ala Thr Gly Val Asn
                85                  90                  95

Ser Val Ala Ile Gly Pro Leu Ser Lys Ala Leu Gly Asp Ser Ala Val
            100                 105                 110

Thr Tyr Gly Ala Ala Ser Thr Ala Gln Lys Asp Gly Val Ala Ile Gly
            115                 120                 125

Ala Arg Ala Phe Thr Ser Asp Thr Gly Val Ala Val Gly Phe Asn Ser
            130                 135                 140

Lys Val Asp Ala Lys Asn Ser Val Ala Ile Gly His Ser Ser His Val
145                 150                 155                 160

Ala Val Asp His Asp Tyr Ser Ile Ala Ile Gly Asp Arg Ser Lys Thr
                165                 170                 175

Asp Arg Lys Asn Ser Val Ser Ile Gly His Glu Ser Leu Asn Arg Gln
            180                 185                 190

Leu Thr His Leu Ala Ala Gly Thr Lys Asp Thr Asp Ala Val Asn Val
            195                 200                 205

Ala Gln Leu Lys Lys Glu Ile Glu Lys Thr Gln Val Asn Ala Asn Lys
            210                 215                 220

Lys Ser Ala Glu Val Leu Gly Ile Ala Asn Asn Tyr Thr Asp Ser Lys
225                 230                 235                 240

Ser Ala Glu Thr Leu Glu Asn Ala Arg Lys Glu Ala Phe Asp Leu Ser
                245                 250                 255

Asn Asp Ala Leu Asp Met Ala Lys Lys His Ser Asn Ser Val Ala Arg

-continued

```
            260                 265                 270
Thr Thr Leu Glu Thr Ala Glu Glu His Thr Asn Lys Lys Ser Ala Glu
            275                 280                 285

Thr Leu Ala Arg Ala Asn Val Tyr Ala Asp Ser Lys Ser Ser His Thr
            290                 295                 300

Leu Gln Thr Ala Asn Ser Tyr Thr Asp Val Thr Val Ser Asn Ser Thr
305                 310                 315                 320

Lys Lys Ala Ile Arg Glu Ser Asn Gln Tyr Thr Asp His Lys Phe Arg
                325                 330                 335

Gln Leu Asp Asn Arg Leu Asp Lys Leu Asp Thr Arg Val Asp Lys Gly
                340                 345                 350

Leu Ala Ser Ser Ala Ala Leu Asn Ser Leu Phe Gln Pro Tyr Gly Val
            355                 360                 365

Gly Lys Val Asn Phe Thr Ala Gly Val Gly Gly Tyr Arg Ser Ser Gln
            370                 375                 380

Ala Leu Ala Ile Gly Ser Gly Tyr Arg Val Asn Glu Ser Val Ala Leu
385                 390                 395                 400

Lys Ala Gly Val Ala Tyr Ala Gly Ser Ser Asp Val Met Tyr Asn Ala
                405                 410                 415

Ser Phe Asn Ile Glu Trp
                420
```

METHODS AND COMPOSITIONS OF CARRIER SYSTEMS FOR THE PURPOSE OF INTRACELLULAR DRUG TARGETING

CROSS-REFERENCE TO RELATED APPLICATIONS

This application is a US National Phase filing of PCT/EP2015/068722, filed on Aug. 14, 2015, which claims priority of PCT/EP2014/067459, filed on Aug. 14, 2014 and EP 14185838.1, filed Sep. 22, 2014. The disclosures therein are expressly incorporated entirely by reference.

The present invention relates to a carrier system, a carrier and a pharmaceutical composition comprising a pathogen entry protein or fragment thereof, which specifically binds to a molecule on the surface of a mammalian target cell of said pathogen and which is covalently linked to the surface of said carrier and at least one hydrophilic antipathogenic agent. It further relates to a method of manufacturing a carrier system and the carrier system or the pharmaceutical composition for the use as a medicament.

BACKGROUND OF THE INVENTION

Infectious diseases caused by pathogenic microorganisms, such as bacteria, viruses, parasites or fungi can be spread directly or indirectly from one person to another. Zoonotic diseases are infectious diseases of animals that can cause disease when transmitted to humans (WHO). For decades, infectious diseases have represented a global health problem responsible for the deaths of millions of people. Today, hundreds of antibiotics are available for the treatment of different infectious diseases. However, one of the major problems facing infection treatment is the increasing resistance particularly of bacteria against many antibiotics, forcing physicians to combine two or even more antibiotics to fight bacterial infections. In addition to bacterial resistance, the poor permeability of some antibiotics through biological membranes is a limiting factor for their effective use, i.e. aminoglycosides, a broad spectrum class of antibiotics comprising molecules such as e.g. streptomycin, amikacin, neomycin, netilimicin, tobramycin and gentamicin. All these molecules exhibit poor permeability profiles through biological membranes and a narrow therapeutic index, associated with notable toxicity, meaning that their use is largely limited to the treatment of extracellular infections. Even if clinical medicine has an extremely long list of different pharmaceutical products at its disposal, the main challenge for scientists and physicians lies in the specificity of these pharmaceutical compounds, and their ability to selectively reach their targets. Normally, drugs are systemically distributed, but to reach the target zone they have to cross many other organs, cells, and intracellular compartments, where they can be partially inactivated. Moreover, side effects, related to drug accumulation and toxicity of therapeutic drugs are still major concerns in medical practice. Therefore, scientists have developed new strategies to make it possible to target drugs towards specific cells, tissues or organs. Most of these strategies are based on using suitable carriers, such as serum proteins, synthetic polymers-based particles, microspheres and liposomes, which can be targeted to specific areas in a variety of different ways, such as immunolabeling. Among these carriers, liposomes are considered as a promising drug delivery system for carrying drugs to the site of action and controlling the release of these drugs at a predetermined rate. Liposomes in themselves are biocompatible and biodegradable (weakly immunogenic inducing no antigenic or pyrogenic reactions) and possess a limited intrinsic toxicity. They provide the possibility to entrap water-soluble pharmacological agents in their internal aqueous compartment or inter bilayer spaces if they are multilamellar vesicles and water-insoluble agents within their lipid membrane(s). They also provide the protection for the encapsulated pharmacological agents from the external environment. Liposomes can be formulated as a solution, aerosol, in a semisolid form or dry vesicular powder (proliposomes for reconstitution). This gives liposomes the opportunity to be administered via a number of different routes, including the oral, topical, pulmonary, nasal, ocular, subcutaneous, intramuscular and intravenous routes. Liposomes can encapsulate both micro and macromolecules. From a pharmacological point of view, liposomes have the ability to modify the pharmacokinetic and pharmacodynamic properties of drugs by increasing their efficacy and therapeutic index, and by reducing drug toxicity and related side effects. Liposomes offer the opportunity to deliver pharmacological agents into cells or even into individual cellular compartments. They provide the possibility to be used in passive targeting and they also offer the flexibility to be coupled with site-specific ligands to achieve active targeting.

In recent years, the idea of using bacterial surface protein invasin in targeted oral drug delivery was considered by some researchers. Invasin was used to mediate gene delivery, where a fragment of invasin was attached to non-specific DNA-binding domains (SPKR). This complex was able to bind $\beta_1$-interin receptors. Approaches attaching peptide tags on nanoparticles to initiate or enhance nanoparticles uptake by mammalian cells have significantly increased over the past years. Yet, impact on clinical praxis remains disappointing. The present inventors have surprisingly found that invasin decorated carriers can be used as a "bacteriomimetic" delivery system. Invasin was used as model bacterial protein to coat liposomes to resemble the Gram-negative bacterium *Yersinia pseudotuberculosis*. Using this model system the successful design of bacteriomimetic/bioinvasive delivery system mimicking invasive bacteria expressing internalization factors integrated in the outer membrane of their cell envelope has been successfully shown. The present invention therefore, provides a new formulation which can be used to enhance the cellular permeability of hydrophilic drugs and reduce its toxicity by encapsulation into nanoparticles. Thus, the resulting formulation can be used for the treatment of intracellular infections reaching bacteria sequestering in intracellular compartments.

SUMMARY OF THE INVENTION

In a first aspect, the present invention provides a carrier system, comprising (i) a carrier, (ii) a pathogen entry protein or fragment thereof, which specifically binds to a molecule on the surface of a mammalian target cell of said pathogen and which is covalently linked to the surface of said carrier, and (iii) at least one hydrophilic antipathogenic agent.

In a second aspect, the present invention provides pharmaceutical composition comprising a carrier system according to first aspect of the present invention and a pharmaceutical acceptable excipient.

In a third aspect of the present invention a method of manufacturing a carrier system according to the first aspect of the present invention is provided, comprising the step of covalently linking the pathogen entry protein or part thereof to the carrier either prior or after contacting the carrier with the at least one hydrophilic antipathogenic agent.

In a fourth aspect of the present invention a carrier system according to the first aspect of the present invention or the pharmaceutical composition according to the second aspect of the present invention for use as medicament is provided.

In a fifth aspect, the present invention provides a carrier system according the first aspect of the present invention or the pharmaceutical composition according to the second aspect of the present invention for the treatment or prophylaxis of infectious diseases, preferably systemic infection.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions:

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step.

A "carrier" as referred to within this specification comprises a composition capable of delivering a reagent to a desired compartment, e.g. a certain cell type, of the human body and is useful for providing and controlling release of drugs after being administered by the chosen administration route and scheme. Carriers that are preferred in the context of the present invention are those that enclose a cavity. It is preferred that the hydrophilic antipathogenic agent of the invention is comprised in this cavity. Carriers may have spherical or almost spherical or non-spherical shape, preferably spherical or almost spherical. To allow the desired uptake of the carrier system of the invention into the desired target area, e.g. a certain cell type, carriers typically have a diameter of less than 1000 μm, more preferably less 500 μm, less than 200 μm, less than 100 μm, less than 50 μm, less than 20 μm, less than 10 μm, less than 5 μm, less than 1 μm, less than 500, less than 200 nm and most preferably less than 100 nm and enclose a cavity, which can comprise the hydrophilic antipathogenic agent of the present invention. Said carrier can be used for systemic or local application. Preferred examples of such carriers are micro- or nanoparticles, e.g. liposomes, nanofibers, nanotubes, nanocubes, virosomes, or erythrocytes etc. The most preferred carrier is a liposome.

The term "invasin" as used in this specification refers to an intracellular membrane protein involved in bacterial adhesion of Enterobacteriaceae, preferably of the *Yersinia, Edwardsiella*, or *Escherichia* species, preferably *Yersinia pseudotuberculosis, Yersinia pestis, Yersinia ruckeri, Yersinia enterocolitica. Yersinia rhodei, Yersinia similis, Escherichia coli* (*E. coli*). Such bacterial adhesion proteins are characterized as "Invasins", if the comprise an invasin consensus spanning amino acids 191 to 289 of SEQ ID NO: 2 or a sequence that shares at least 70%, more preferably at least 80%, and even more preferably at least 90% amino acid sequence identity to the consensus sequence over the entire length of the consensus sequence. A particularly preferred invasin is invasin A encoded by the inv gene of *Yersinia pseudotuberculosis* (see e.g. Gene Bank Accession No. M17448). This protein consists of 986 amino acid residues, and can be divided into two parts; the first region, consisting of the N-terminal region (or N-terminus) is located within the outer membrane of the bacterium, while the second part of the protein towards the C-terminal region (or C-terminus) is located extracellularly. The extracellular region of the protein has been shown to be the interaction site with $\beta_1$-interin receptors of the host. As mentioned above, invasin is known to promote the attachment and uptake of *Yersinia* by microfold cells of the epithelial lining of the GI tract. Upon binding of invasin to β1 integrin receptors on epithelial cells, a chain of signaling cascades provokes rearrangement of the cytoskeletal system that leads to protrusions of the host membrane which surround the bacterium, eventually internalizing it.

The term "internalin" as referred to within this specification comprises a surface protein of *Listeria monocytogenes*. There exist two different Internalins, In1A and In1B, encoded by two genes and have common structural features, i.e. two repeat regions, the leucine-rich repeat regions and the B-repeat region, separated by a highly conserved interrepeat region. The carboxy-terminal region of In1A contains an LPXTG motif, a signature sequence necessary for anchoring internalin on the bacterial surface and that internalin exposed on the surface is capable of promoting entry. In1B contains repeated sequences beginning with the amino acids GW, necessary to anchor In1B to the bacterial surface. Internalins are used by the bacteria to invade mammalian cells via cadherins or other transmembrane proteins of the host. InlA is necessary to promote *Listeria* entry into human epithelial cells, .i.e. Caco-2 cells, wherein InlB is necessary to promote *Listeria* internalization in several other cell types, including hepatocytes, fibroblasts and epithelioid cells, such as Vero, HeLa, CHO, or HEp-2 cells.

The term "mammalian target cell" as referred to within this specification comprises any cell which originates from a mammal. Further, the mammalian target cell can be in an infected condition wherein this infected condition is triggered by a pathogen invaded in said mammalian cell. Pathogens or infective agents are microorganisms, such as a virus, bacterium, prion, fungus or protozoan that causes disease in its host. A mammalian target cell is any cell from mammalian tissue which can be targeted by the carrier system of the present invention.

The term "hydrophilic antipathogenic agent" as used in the context of the present invention is a molecule or compound capable of either killing an infectious pathogen which invaded a host cell or decreasing the amount of infectious pathogen in a host cell invaded by said pathogen by interacting with the pathogens molecular machinery. The molecular machinery comprises the nucleic acid and protein biosynthesis. The hydrophilic antipathogenic agent comprises at least one hydrophilic moiety. A hydrophilic moiety, hydrophilic molecule or portion of a hydrophilic molecule is one that has a tendency to interact with or be dissolved by water and other polar substances. Preferably, hydrophilic antipathogenic agents have a solubility in water at 20° C. of at least 1 μg per ml water, more preferably of at least 10 μg per ml water, more preferably of at least 100 μg, more preferably of at least 1 mg per ml water, more preferably of at least 10 mg per ml water, and most preferably of at least 100 mg per ml water. Hydrophilic substances can seem to attract water out of the air. This is thermodynamically favourable than interaction with hydrophobic solvents, and makes these molecules soluble not only in water but also in other hydrophilic or polar solvents. There are hydrophilic and hydrophobic parts of the cell membrane. A hydrophilic molecule or portion of a molecule is one that is typically charge-polarized and capable of hydrogen bonding, enabling it to dissolve more readily in water than in oil or other hydrophobic solvents. Some hydrophilic molecules are known as polar molecules. Polarity refers to a separation of electric charge leading to a molecule or its chemical groups having an electric dipole or multipole moment. Polar molecules interact through dipole-dipole intermolecular forces and hydrogen bonds. Molecular polarity is dependent on the difference in electronegativity between atoms in a compound and the asymmetry of the compound's structure. Polarity underlies a number of physical properties, inter alia solubility. Preferably the hydrophilic antipathogenic agent dissolves in water, pyridine, dimethylformamide, and acidic media with salt formation, dissolves moderately in methanol, ethanol, and acetone and is practically insoluble in benzene or halogenated hydrocarbons. The hydrophilic antipathogenic agent can be selected from the group consisting of small molecules, proteins; nucleic acids, preferably siRNA; nucleotides, preferably polynucleotides antibiotics or cytostatics.

The term "liposomes" as used herein refers to spherical soft-matter vesicles consisting of one or more bilayers of amphiphilic molecules encapsulating a volume of aqueous medium. Preferred amphiphilic molecules are natural or synthetic lipids, phospholipids or mixtures thereof. The phospholipids may further contain cholesterol as mentioned in more detail below. Lipids used for the formation of liposomes of the invention consist of a hydrophilic headgroup and hydrophobic tail; in excess in aqueous solutions, such lipids orient themselves so that hydrophilic headgroups are exposed to the aqueous phase while the hydrophobic hydrocarbon moieties (fatty acid chains having 10-24 carbon atoms and 0-6 double bonds in each chain) are forced to face each other within the bilayer. Therefore, the liposomes are able to entrap both hydrophilic and lipophilic/hydrophobic drugs—water-soluble drugs may be located in their internal or inter-bilayer aqueous spaces, while lipophilic/hydrophobic drugs may incorporate within the membrane itself. Cholesterol and/or its derivatives are quite often incorporated into the phospholipid membrane. These compounds arrange themselves within liposomes with hydroxyl groups oriented towards the aqueous surfaces and aliphatic chains aligned parallel to the acyl chains in the center of the bilayer. The presence of cholesterol or derivatives makes the membrane less ordered and slightly more permeable below the transition temperature of phospholipids, while above the transition temperature membranes containing cholesterol exhibit a more rigid/less fluid structure. On the basis of their structural properties, liposomes can vary widely in size which is an important parameter for circulation half-life. They may also vary in the number and position of lamellae present. Both liposome size and number of bilayers affect the degree of drug encapsulation in liposomes. According to the number of bilayers, liposomes can be divided into different categories. Unilamellar vesicles are structures in which the vesicle has a single phospholipid bilayer enclosing the aqueous core, and can be further divided into three important groups; small unilamellar vesicles (SUV) which have a size range between 0.02 μm and 0.1 μm; large unilamellar vesicles (LUV) with a size range between 0.1 μm and 1 μm; and giant unilamellar vesicles, which have a size of more than 1 μm. Multilamellar vesicles (MLU) which usually consist of a population of vesicles covering a wide range of sizes more than 0.5 μm, each vesicle generally consisting of three or more concentric lamellae. Vesicles composed of just a few concentric lamellae are called oligolamellar vesicles (OLV). These vesicles are considered to be two bilayers, and range in size from 0.1 μm-1 μm. Multivesicular vesicles (MVV) can also occur, wherein two or more vesicles are enclosed together in a nonconcentric manner within another larger one with a size range more than 0.1 μm. Liposomes can be classified according to their chemical characteristics. As mentioned, liposomes are composed of natural and or synthetic lipids, and may also contain other constituents such as cholesterol and hydrophilic polymer-conjugated lipids. The physicochemical characteristics of lipids composing the liposomal membrane, such as their fluidity, permeability and charge density, determine the behavior of liposomes following their application or administration. The importance of liposome composition in their action as drug delivery systems has led to a composition-based classification system for liposomes. Conventional liposomes consist of neutral or negatively charged phospholipids and cholesterol, containing a hydrophilic drug encapsulated inside the liposome or hydrophobic drug incorporated into the liposome bilayer. Long-circulating liposomes (LCL) are liposomes functionalized with a protective polymer such as polyethyleneglycol (PEG) to avoid opsonization. Long-circulating immuno-liposomes are liposomes functionalized with both a protective polymer and antibody, which can be grafted to the liposome bilayer or attached to the distal end of the coupled polymer. Smart liposomes comprise liposomes with single or multiple modifications, such as attachment of a diagnostic label, incorporation of stimuli-sensitive lipids, incorporation of positively charged lipids which allow the functionalization with DNA, attachment of cell-uptake peptides, attachment of stimuli-sensitive polymer, or incorporation of viral components. In addition, all these types of liposomes can be loaded with magnetic-targeting particles, or with diagnostic markers, e.g. fluorescence markers; or gold or silver particles for imaging using electron microscopy.

The term "molecule on the surface of a mammalian target cell" as referred to in this specification comprises a protein capable of specifically interacting with the pathogen-entry-protein. It further comprises a receptor, a protein molecule which is usually found inside or on the surface of a cell that receives chemical signals from outside the cell. When such chemical signals bind to a receptor, they cause some form of cellular/tissue response, e.g. change in the electrical activity of the cell. In this sense, a receptor is a molecule that recognizes and responds to endogenous chemical signals, e.g. the acetylcholine receptor recognizes and responds to its endogenous ligand, acetylcholine. However sometimes in pharmacology, the term is also used to include other proteins that are drug targets, such as enzymes, transporters and ion channels. Receptor proteins are embedded in either the cell's plasma membrane (cell surface receptors), the cytoplasm (cytoplasmic receptors), or in the nucleus (nuclear receptors). A molecule that binds to a receptor is called a ligand, and can be a peptide (short protein) or another small molecule such as a neurotransmitter, hormone, pharmaceutical drug, or toxin. The endogenously designated molecule for a particular receptor is referred to as its endogenous ligand. Each receptor is linked to a specific cellular biochemical pathway. While numerous receptors are found in most cells, each receptor will only bind to ligands of a particular structure, much like how locks will only accept specifically shaped keys. When a ligand binds to its corresponding receptor, it activates or inhibits the receptor's associated biochemical pathway. The structures of receptors are very diverse and can broadly be classified into the ionotropic receptors, G-protein-coupled receptors, kinase-linked and related receptors and nuclear receptors.

The term "bacterium sequestering in a non-phagocytic cell" in the context of the present specification refers to a bacterium which invaded into the intracellular space of a host cell and exists therein in an abandoned part, i.e. a vacuole or capsule, typically to evade immune response, wherein the host cell is a non-phagocytic cell. Non-phagocytic cells comprise all type of cells which does not ingest and destroy foreign particles, bacteria, and cell debris.

The term "pathogen" as used within this specification comprises typically an infectious agent (colloquially known as a germ)—a microorganism such as a virus, bacterium, prion, fungus or protozoan, that causes disease in its host. The host may be an animal, a plant or a fungus.

"Gram-negative bacteria" as used within this specification comprises a class of bacteria that do not retain the crystal violet stain used (contrarily to Gram-positive bacteria) in the Gram staining method of bacterial differentiation making positive identification possible. The thin peptidoglycan layer of their cell wall is sandwiched between an inner cell membrane and a bacterial outer membrane. In Gram staining, the outer lipid-based membrane of Gram-negative bacteria is removed by an alcohol solution which also decolorizes the then exposed peptidoglycan layer by dissolving away the previously applied crystal violet. A counterstain (safranin or fuchsine) is then added which recolorizes the bacteria red or pink. Gram-positive bacteria comprise *Streptococcus, Staphylococcus, Bacillus, Clostridium, Corynebacterium* and *Listeria*. Common Gram-negative bacteria comprise the proteobacteria, a major group of Gram-negative bacteria, including *E. coli, Salmonella, Shigella*, and other Enterobacteriaceae (*Yersinia*), *Pseudomonas, Moraxella, Helicobacter, Stenotrophomonas, Bdellovibrio*, acetic acid bacteria, *Legionella*. A well-known Gram-negative bacterium is *Yersinia pseudotuberculosis* which is facultative anaerobic, coccoid bacillus of the genus *Yersinia* from the Enterobacteriaceae family. It is motile at room temperature but non-motile at 37° C. The genome of *Yersinia pseudotuberculosis* contains one circular chromosome and two plasmids; one of the plasmids is responsible for the virulence of the bacteria and the other one encodes mobilization information. Once it has achieved entry into Microfold cells (M-cells), epithelial cells or phagocytes, *Yersinia pseudotuberculosis* is enclosed in an acidic compartment called a Bacteria-containing vacuole (BCV). *Y. pseudotuberculosis* alters the endocytic pathway of this vacuole in order to avoid being destroyed, and replicates. *Yersinia* species, including *Yersinia pseudotuberculosis* and *Yersinia enterocolitica* cause several GI disorders such as enteritis, colitis, diarrhea, lymphadenitis, and other associated disorders such as erythema nodosum, uveitis and septicemia. These bacteria promote their own uptake through the epithelial lining of the GI tract by interaction with M-cells, via a small bacterial membrane-bound protein called invasin. In this way they gain access to the host lymphatic system; by macrophages and cause inflammation of these tissues. Typical symptoms of systemic *Yersinia pseudotuberculosis* infection include joint or back pain, abdominal cramps and diarrhea. Infection, in both local and systemic cases, can be treated by tetracyclines, aminoglycosides, chloramphenicol and third generation cephalosporins. Another Gram-negative species is *Salmonella*, a rod-shaped, predominantly motile enteric bacterium. The genome of *Salmonella enterica* contains one chromosome and plasmid. Salmonella. enterica has an outer membrane consisting largely of lipopolysaccharides which protect the bacteria from the environment. *Samonella* species are facultative intracellular pathogens, that enter cells by manipulating the host's cytoskeletal elements and membrane trafficking pathways, which initiates an actin-mediated endocytic process called macropinocytosis via *Salmonella*-Invasion-Proteins (Sips). Intracellular bacteria replicate within a membrane-bound vacuole known as the *Salmonella*-containing vacuole. However, this bacterium can also replicate efficiently in the cytosol of epithelial cells; intracellular growth is therefore a product of both vacuolar and cytosolic replication. *Salmonella enterica* causes gastroenteritis in humans and other mammals. The disease is characterized by diarrhea, abdominal cramps, vomiting and nausea, and generally lasts up to 7 days. Infections caused by *Samonella* species are usually treated with aminoglycosides and chloramphenicol. Other gram negative bacteria comprise the proteobacteria, a major group of Gram-negative bacteria, including *E. coli, Salmonella, Shigella*, and other Enterobacteriaceae, *Pseudomonas, Moraxella, Helicobacter, Stenotrophomonas, Bdellovibrio*, acetic acid bacteria, *Legionella*. Other notable groups of Gram-negative bacteria include the cyanobacteria, spirochaetes, green sulfur, and green non-sulfur bacteria. Medically relevant Gram-negative cocci include the three organisms that cause a sexually transmitted disease (*Neisseria gonorrhoeae*), a meningitis (*Neisseria meningitidis*), and respiratory symptoms (*Moraxella catarrhalis*). Medically releva nt gram-negative bacteria include a multitude of species. Some of them cause primarily respiratory problems (*Hemophilus influenzae, Klebsiella pneumoniae, Legionella pneumo-*

*phila, Pseudomonas aeruginosa*), primarily urinary problems (*E. coli, Proteus mirabilis, Enterobacter cloacae, Serratia marcescens*), and primarily gastrointestinal problems (*Helicobacter pylori, Salmonella enteritidis, Salmonella typhi, Campylobacter jejuni*). Gram-negative bacteria associated with hospital-acquired infections include *Acinetobacter baumannii*, which cause bacteremia, secondary meningitis, and ventilator-associated pneumonia in hospital intensive-care units.

The term "covalently linked" as used within this specification describes two molecules connected by a covalent bond which is a chemical bond that involves the sharing of electron pairs and atoms. Commonly known in protein/peptide chemistry, the N-terminus of a protein/peptide is used to being covalently linked to a carboxyl group of the linkage partner. The carboxylic groups of the cross-linking partner usually needs to be first activated using suitable reagents. To enhance the electrophilicity of carboxylate group, the negatively charged oxygen must first be transformed into a better leaving group. Dicyclohexylcarbodiimid (DCC) is used for this purpose. The negatively charged oxygen will act as a nucleophile, attacking the central carbon in DCC. DCC is temporarily attached to the former carboxylate group forming a highly electrophilic intermediate, making nucleophilic attack by the terminal amino group on the growing peptide more efficient.

The reaction results in the formation of an amide. Other suitable supporting reagents for activation are N,N'-diisopropylcarbodiimide (DIC), N,N'-dicyclohexylcarbodiimide (DCC), N-(3-dimethylaminopropyl)-N-ethylcarbodiimide hydrochloride (EDC) or N-hydroxysuccinimide (NHS).

The term "protein" as referred to within this specification comprises large biological molecules, or macromolecules, consisting of one or more long chains of amino acid residues. Proteins perform a vast array of functions within living organisms, including catalyzing metabolic reactions, replicating DNA, responding to stimuli, and transporting molecules from one location to another. Proteins differ from one another primarily in their sequence of amino acids, which is dictated by the nucleotide sequence of their genes, and which usually results in folding of the protein into a specific three-dimensional structure that determines its activity.

The term "nucleic acid" as used in this specification comprises polymeric or oligomeric macromolecules, or large biological molecules, essential for all known forms of life. Nucleic acids, which include DNA (deoxyribonucleic acid) and RNA (ribonucleic acid), are made from monomers known as nucleotides. Most naturally occurring DNA molecules consist of two complementary biopolymer strands coiled around each other to form a double helix. The DNA strand is also known as polynucleotides consisting of nucleotides. Each nucleotide is composed of a nitrogen-containing nucleobase as well as a monosaccharide sugar called deoxyribose or ribose and a phosphate group. Naturally occurring nucleobases comprise guanine (G), adenine (A), thymine (T), uracil (U) or cytosine (C). The nucleotides are joined to one another in a chain by covalent bonds between the sugar of one nucleotide and the phosphate of the next, resulting in an alternating sugar-phosphate backbone. If the sugar is desoxyribose, the polymer is DNA. If the sugar is ribose, the polymer is RNA. Typically, a polynucleotide is formed through phosphodiester bonds between the individual nucleotide monomers. In the context of the present invention the term "nucleic acid" includes but is not limited to ribonucleic acid (RNA), deoxyribonucleic acid (DNA), and mixtures thereof such as e.g. RNA-DNA hybrids (within one strand), as well as cDNA, genomic DNA, recombinant DNA, cRNA and mRNA. A nucleic acid may consist of an entire gene, or a portion thereof, the nucleic acid may also be a miRNA, siRNA, or a piRNA. MiRNAs are short ribonucleic acid (RNA) molecules, which are on average 22 nucleotides long but may be longer and which are found in all eukaryotic cells, i.e. in plants, animals, and some viruses, which functions in transcriptional and post-transcriptional regulation of gene expression. MiRNAs are post-transcriptional regulators that bind to complementary sequences on target messenger RNA transcripts (mRNAs), usually resulting in translational repression and gene silencing. Small interfering RNAs (siRNAs), sometimes known as short interfering RNA or silencing RNA, are short ribonucleic acid (RNA molecules), between 20-25 nucleotides in length. They are involved in the RNA interference (RNAi) pathway, where they interfere with the expression of specific genes. PiRNAs are also short RNAs which usually comprise 26-31 nucleotides and derive their name from so-called piwi proteins they are binding to. The nucleic acid can also be an artificial nucleic acid. Artificial nucleic acids include polyamide or peptide nucleic acid (PNA), morpholino and locked nucleic acid (LNA), as well as glycol nucleic acid (GNA) and threose nucleic acid (TNA). Each of these is distinguished from naturally-occurring DNA or RNA by changes to the backbone of the molecule.

The term "antibiotic" as referred to in the present specification comprises agents that are capable of killing or at least inhibiting growth of microorganisms, preferably of bacteria. Antibiotics can be selected from the group comprising β-lactam antibiotics, e.g. penicillins comprising benzylpenicillin, phenoxymethylpenicillin, piperacillin, mezlocillin, ampicillin, amoxicillin, flucloxacillin, methicillin, oxacillin; β-lactamase inhibitors e.g. clavulanic acid, sulbactam, tazobactam, sultamicillin; monobactams e.g. aztreonam; cephalosporins comprising cefazolin, cefalexin, loracarbef, cefuroxime, cefotiam, cefaclor, cefotaxime, ceftriaxone, cefepime, ceftazidime, cefixime, cefpodoxime, ceftibuten; carbapenems comprising imipenem, meropenem, ertapenem; lipopeptides e.g. daptomycin, glycopeptides e.g. bleomycin, vancomycin, teicoplanin, aminoglycosides e.g. gentamicin, dibekacin, sisomicin, tobramycin, amikacin, kanamycin, neomycin, streptomycin, netilmicin, apramycin, paromomycin, spectinomycin, geneticin; oxazolidinediones e.g. linezolid; glycylcyclines e.g. tigecycline; polypeptides e.g. polymyxin, polyketides, e.g. tetracyclines comprising tetracycline, oxytetracycline, minocycline, doxycycline, chlortetracycline, rolitetracycline or macrolides comprising erythromycin, azithromycin, clarithromycin, roxythromycin; ketolides e.g. telithromycin; quinolones e.g. ciprofloxacin, norfloxacin, ofloxacin; moxifloxacin, enoxacin, gatifloxacin, sparfloxacin, pefloxacin, fleroxacin, levofloxacin, trovafloxacin; sulfonamides e.g. sulfamethoxazole, sulfacarbamide, sulfacetamide, sulfamethylthiazole, sulfadiazine, sulfamethoxozole, sulfasalazine. Also comprised are organic or anorganic salts of above listed molecules.

The term "cytostatic" as referred to in the specification comprises chemical substances, especially one or more anti-cancer drugs or so-called chemotherapeutic agents. It is noted that some antibiotics, e.g. sulfadicramide, or sulfadimethoxine, also have cytostatic activity and are, thus also included in the list of preferred cytostatics. The decisive criterion for using a cytostatic in the context of the present invention is the hydrophilicity. Cytostatics can be categorized in alkylating agents, anti-metabolites, anti-microtubule agents, topoisomerase inhibitors and cytotoxic antibiotics.

Comprised are anti-metabolites, epothilones, nuclear receptor agonists and antagonists, anti-androgens, anti-estrogens, platinum compounds, hormones and antihormones, interferons and inhibitors of cell cycle-dependent protein kinases (CDKs), inhibitors of cyclooxygenases and/or lipoxygenases, biogeneic fatty acids and fatty acid derivatives, including prostanoids and leukotrienes, inhibitors of protein kinases, inhibitors of protein phosphatases, inhibitors of lipid kinases, platinum coordination complexes, ethyleneamines, methylmelamines, trazines, vinca alkaloids, pyrimidine analogs, purine analogs, alkylsulfonates, folic acid analogs, anthracenediones, substituted urea, methylhydrazine derivatives, in particular acediasulfone, aclarubicin, ambazone, aminoglutethimide, L-asparaginase, azathioprine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin, dapsone, daunorubicin, dibrompropamidine, diethylstilbestrol, docetaxel, doxorubicin, enediynes, epirubicin, epothilone B, epothilone D, estramustin phosphate, estrogen, ethinylestradiol, etoposide, flavopiridol, floxuridine, fludarabine, fluorouracil, fluoxymesterone, flutamide, fosfestrol, furazolidone, gemcitabine, gonadotropin releasing hormone analog, hexamethylmelamine, hydroxycarbamide, hydroxymethylnitrofurantoin, hydroxyprogesteronecaproate, hydroxyurea, idarubicin, idoxuridine, ifosfamide, interferon α, irinotecan, leuprolide, lomustine, lurtotecan, mafenide sulfate, olamide, mechlorethamine, medroxyprogesterone acetate, megastrol acetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, bleomycin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, acriflavinium chloride, semustine, streptozotocin, sulfacarbamide, sulfacetamide, sulfachloropyridazine, sulfadiazine, sulfadicramide, sulfadimethoxine, sulfaethidole, sulfafurazole, sulfaguanidine, sulfaguanole, sulfamethizole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, testolactone, testosterone propionate, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin. Also comprised are organic or anorganic salts of above listed molecules.

The term "pharmaceutical composition" as used herein refers to the combination of an active agent with a carrier, inert or active, making the composition suitable for therapeutic use. Further, pharmaceutical compositions comprising the carrier system of the present invention can be formulated for oral, parenteral, topical, inhalative, rectal, sublingual, transdermal, subcutaneous or vaginal application routes according to their chemical and physical properties. Pharmaceutical compositions comprise solid, semisolid, liquid, or transdermal therapeutic systems (TTS). Solid compositions are selected from the group consisting of tablets, coated tablets, powder, granulate, pellets, capsules, effervescent tablets or transdermal therapeutic systems. Also comprised are liquid compositions, selected from the group consisting of solutions, syrups, infusions, extracts, solutions for intravenous application, solutions for infusion or solutions of the carrier systems of the present invention. Semisolid compositions that can be used in the context of the invention comprise emulsion, suspension, creams, lotions, gels, globules, buccal tablets and suppositories.

The term "release kinetic" as used within this specification refers to the release of the hydrophilic antipathogenic agent from the carrier system or the carrier from the pharmaceutical composition of the present invention to its molecular target. Pharmacokinetics comprises the determination of the fate of a substance administered to a living organism and may comprise different kinetics, i.e. rapid release, prolonged or delayed release or sustained release.

Embodiments

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. In the work leading to the present invention, it was surprisingly shown that pathogen entry proteins linked to a carrier are able to transfer an antipathogenic agent into a mammalian cell.

Based on these results the present invention provides in a first aspect a carrier system, comprising
(i) a carrier,
(ii) a pathogen entry protein or fragment thereof, which specifically binds to a molecule on the surface of a mammalian target cell of said pathogen and which is covalently linked to the surface of said carrier, and
(iii) at least one hydrophilic antipathogenic agent.

The pathogenic entry-protein is covalently linked, either directly or via a linker to all or part of the surface of said carrier. The surface is preferably the outer surface of the carrier. A linker is a chemical molecule that increase the distance between the two entities linked. Typically a linker also improves the flexibility of motion between the two entities linked. It can be straight or branched. Preferred linkers are peptide linkers, which can be incorporated, e.g. at the N- or C-terminus of the pathogen entry protein. To provide improved flexibility small amino acids are used, which are selected from G, A, S, L, I, and V, preferably from G, A, and S.

The carrier system itself can provide different forms of release kinetics according to the physical and chemical properties of the carrier and the chemical interaction between the carrier and the hydrophilic antipathogenic agent. Depending on the carrier and type of chemical interaction the mode of release can be selected from rapid release, sustained release, or delayed release. The hydrophilic antipathogenic agent can be comprised in the carrier system of the invention in different ways. It is preferred that it is attached in a way that leads to release once the carrier system reaches its target area, e.g. enters the target cell. To that end it can be covalently or non-covalent linked to the carrier. If the link is covalent, it is preferred that the linkage is cleaved in the intracellular environment. It is particularly preferred that the hydrophilic antipathogenic agent is comprised in a cavity of the carrier system.

A "pathogen entry protein" as used in the context of the present invention is a protein which facilitates entry of pathogenic organisms, preferably a bacterium, into a particular host cell and facilitates infection of said cell. Also comprised are fragments of such proteins, i.e. proteins carrying N-terminal, C-terminal, and/or internal deletions, and still capable of mediating entry into a particular host cell. Successful establishment of intracellular infection by bacterial pathogens requires first an adhesion to the host cells and then cellular invasion, frequently followed by intracellular multiplication, dissemination to the other tissues, or persistence. Bacteria used monomeric adhesins/invasins or highly sophisticated macromolecular machines such as type III secretion system to establish a complex host/pathogen interaction which leads to subversion of cellular functions and establishment of disease. Many pathogenic organisms, for example many bacteria must first bind to host cell surfaces and several bacterial and host molecules that are involved in the adhesion of bacteria to host cells have been identified. Often, the host cell receptors for bacteria are essential proteins for other functions. Due to presence of mucous lining and of anti-microbial substances around some host cells, it is difficult for certain pathogens to establish direct contact-adhesion. Some virulent bacteria produce proteins that either disrupt host cell membranes or stimulate their own endocytosis or macro-pinocytosis into host cells. These virulence factors allow the bacteria to enter host cells and facilitate entry into the body across epithelial tissue layers at the body surface.

One purpose of the carrier system of the present invention is to deliver hydrophilic antipathogenic agents like antibiotics or cytostatics loaded onto or into the carrier and using a pathogen entry protein and its invasion mechanism accessing a mammalian target cell which is in an infected state.

In a preferred embodiment of the first aspect of the present invention the carrier is selected from micro- or nanospheres, i.e. nanoparticles or liposomes, nanofibers, nanotubes, nanocubes, virosomes, or erythrocytes. In the most preferred embodiment the carrier is a liposome. The liposome may be a unilamellar or multilamellar liposome and/or neutral, positively or negatively charged liposomes.

Preferably, the carrier is covalently linked to the C-terminus, N-terminus or an amino acid side chain of the pathogen-entry-protein, more preferably via the N-terminus of the pathogen-entry-protein. As set out above, the carrier is a liposome in a preferred embodiment. In this embodiment the pathogen entry protein is covalently linked to one of the amphiphilic molecules comprised in the lipid layer(s) of the liposome. Preferably the covalent link is between to the hydrophilic part of the amphiphilic molecule and the C-terminus, N-terminus or an amino acid side chain, more preferably via the N-terminus of the pathogen-entry-protein, thereby ascertaining that the pathogen entry protein is accessible on the surface of the carrier, e.g. the liposome. This is preferred to mediate the entry function of the pathogenic-entry-protein. Preferred examples of lipids for covalently connecting pathogenic entry-proteins comprise lipids selected from the group consisting of 1,2-diaplmitoyl-sn-glycero-3-phosphocholine (DPPC), cholesterol, 1,2-dihexadecanoyl-sn-glycero-3-phosphoethanolamine-N-(glutaryl) sodium salt.

The amphiphilic molecule, preferably the lipid that is covalently attached to the pathogen entry protein (the "anchor molecule") may be used solely to form the liposome or may be used in admixture with other amphiphilic molecules forming the liposome. Preferably the anchor molecule constitutes less than 50 weight %, less than 30 weight %, less than 20 weight %, less than 10 weight %, preferably less than 9 weight %, less than 8 weight %, less than 7 weight % of the total weight of the amphiphilic molecules, preferably lipids forming the liposome.

In a particular preferred combination the molar ratio of 1,2-diaplmitoyl-sn-glycero-3-phosphocholine (DPPC), cholesterol, 1,2-dihexadecanoyl-sn-glycero-3-phosphoetha-nolamine-N-(glutaryl) sodium salt is 6:3:0.6. It is preferred that the pathogen entry protein or at least fragments thereof, are linked to the liposome either via its N-terminus, C-terminus or a side chain, more preferably the pathogen entry protein or at least fragments thereof is linked via its N-terminus to an activated carboxyl group of 1,2-dihexadecanoyl-sn-glycero-3-phosphoethanolamine, preferably a glutaryl group of 1,2-dihexadecanoyl-sn-glycero-3-phosphoethanolamine-N-(glutaryl) sodium salt.

It is well known in the art how to covalently couple a protein to a carrier. It is preferred that that the carrier, in particular amphiphilic molecules forming the liposome, are covalently attached to the pathogen entry protein using carbodiimide.

In a further preferred embodiment, the carrier delivers or improves delivery of an antipathogenic agent to a target cell. Preferably, the target cell is a mammalian cell, more preferably a mammalian cell infected by a pathogen.

In another preferred embodiment the pathogen entry protein is an intracellular membrane protein from a bacterium, preferably from a Gram-negative bacteria. It is preferred that the pathogen entry protein is a bacterial adhesion protein selected from the group consisting of invasin A, invasin B (Ifp), invasin C, invasin D, invasin E, YadA, other YadA-related (or YadA-type) proteins, internalin and fragments thereof. More preferably, the pathogen entry pathogen is invasin A or a fragment thereof.

In another preferred embodiment the carrier system comprises multiple carriers as described. In another preferred embodiment, the carrier system itself can provide different forms of release kinetics according to the physical and chemical properties of the carrier. It is preferred that the release kinetic is selected from the group of controlled release, preferably rapid release, delayed release, sustained release. More preferably the kinetic of the carrier systems is a sustained release kinetic. In another preferred embodiment, the hydrophilic antipathogenic agent can be attached in different ways, for example covalently coupled or in a non-covalent way, i.e. by van-der-Waals-forces. In another preferred embodiment the carrier system comprises the carrier and the pathogen entry protein covalently linked, either direct or via a linker which is preferably straight or branched. In another preferred embodiment the pathogen entry protein is linked either via its C-terminus, its N-terminus or a side chain of the pathogen entry protein, preferably the pathogen entry protein is linked via its N-terminus. It is noted that the C-terminus and N-terminus referred to in the context of the pathogen entry protein may be the natural C-terminus or N-terminus but may be the C-terminus or N-terminus that results when C-terminal or N-terminal amino acid sequences are removed from a naturally occurring pathogen entry protein, e.g. in a C-terminal fragment of invasin A the N-terminus In a preferred embodiment of the first aspect of the present invention the pathogen entry protein is a protein or at least a fragment of the protein, which is used by pathogenic organisms to enter a particular host cell of said pathogen and to infect said cell. Preferably, a chain of signaling cascades is provoked by specifically binding of said pathogen entry protein to a molecule on the surface of a target cell, leading to the rearrangement of the cytoskeletal system that leads to protrusions of the host membrane which surround the bacterium and internalizing it. It is preferred that said pathogen entry protein enters the cell via specifically binding to a molecule on the target cells' surface.

In another preferred embodiment the fragment of the pathogen entry protein is a contiguous part of the pathogen entry protein, shorter in length but having at least 70%, 75%, 80%, 85%, 90%, or at least 95% sequence identity. It is preferred that the fragment also has the ability to specifically bind to a "molecule on the surface of a mammalian target cell" which comprises a protein capable of specifically interacting with the pathogen entry protein. Preferably, the fragment consists or essentially consists of the extracellular domain of the pathogen entry protein, more preferably the fragment consists or essentially consists of the extracellular domain and transmembrane domain of invasin, even more preferably only the extracellular domain and most preferably the fragment is encoded by SEQ ID NO: 2. The skilled person is well aware how to determine the extracellular domain of a given pathogen entry protein.

In another preferred embodiment the pathogen entry protein is an intracellular membrane protein from a bacterium, preferably, from a Gram-negative bacterium. Even more preferably, it is from a bacterium that sequesters in a non-phagocytic cell. In another preferred embodiment the pathogen entry protein is a bacterial adhesion protein selected from the group consisting of invasin A, invasin B (Ifp), invasin C, invasin D, invasin E, YadA, internalin and variants thereof. More preferably, the pathogen entry protein is invasin A. In a preferred embodiment the pathogen entry protein has the amino acid sequence as indicated in SEQ ID NO: 1, or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 2 or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 3 or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 4, or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 5, or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 6, or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 7, or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 8, or variants thereof with at least 70%, 75%, 80%, 85%, 90%, or 95% amino acid sequence identity and which specifically binds to the extracellular domain of the $\beta_1$-interin receptor. In a preferred embodiment the pathogen entry protein has the amino acid sequence as indicated in SEQ ID NO: 9, or variants thereof with at least 70%, 75%, 80%, 85%, 90%, or 95% amino acid sequence identity and which specifically binds to the extracellular domain of the $\beta_1$-interin receptor.

Sequence identities between two proteins or nucleic acids are preferably determined over the entire length of the variant using the best sequence alignment with the reference sequence, e.g. SEQ ID NO: 1, and/or over the region of the best sequence alignment, wherein the best sequence alignment is obtainable with art known tools, e.g., Align, using standard settings, preferably EMBOSS:needle, Matrix: Blosum62, Gap Open 10.0, Gap Extend 0.5, with amino acid residues 1 to 210 of the amino acid sequence set forth in SEQ ID NO: 4. In another preferred embodiment the fragment of the pathogen entry protein consists or essentially consists of the extracellular domain of the pathogen entry domain.

In another embodiment of the first aspect of the present invention the molecule on the surface of the mammalian target cell provides specific binding of the pathogen entry protein. Preferably said molecule is selected from the group of carbohydrates, lipids or proteins, more preferably the molecule on the surface of the mammalian target cell is a protein. In a preferred embodiment the protein is capable of specifically interacting with the pathogen entry protein. It is preferred that the protein is a receptor protein which is usually found inside or on the surface of a cell that receives chemical signals from outside the cell. More preferably, the protein is selected from the group consisting of ionotropic receptors, kinase-linked and related receptors, nuclear receptors or G-protein coupled receptors. It is preferred that the protein is a member of the family of β-integrin receptors, more preferably the protein is the $\beta_1$-integrin receptor. In another preferred embodiment, specific binding of the pathogen entry protein to the receptor protein causes some form of cellular/tissue response leading to the invasion of the pathogen entry protein into the mammalian target cell.

In a preferred embodiment of the first aspect of the present invention the pathogen is a microorganism selected from the group consisting of virus, bacterium, prion, fungus or protozoan. Preferably, the pathogen is a bacteria selected from the group of Gram-positive or Gram-negative bacteria. More preferably, the pathogen is a Gram-negative bacteria selected from the group consisting of *Chlamydia, Coxiella burnetti, Ehrlichia, Rickettsia, Legionella, Salmonella, Shigella* or *Yersinia*. Even more preferably the pathogen is *Yersinia pseudotuberculosis* or *Yersinia enterocolitica*.

In another preferred embodiment of the first aspect of the present invention the mammalian target cell is any cell which originates from a mammal. It is preferred that the mammalian target cell is in an infected condition wherein this infected condition is triggered by a pathogen invaded in said mammalian cell. Preferably, said mammalian target cell is selected from the group consisting of endothelial and epithelial cells. More preferably, said mammalian target cells are epithelial cells.

In another preferred embodiment of the first aspect of the present invention the hydrophilic antipathogenic agent is a molecule or compound capable of either killing an infectious pathogen which invaded a host cell or decreasing the amount of infectious pathogen in a host cell invaded by said pathogen by interacting with the pathogens molecular machinery. The hydrophilic antipathogenic agent is selected from the group consisting of small molecules, proteins; nucleic acids, preferably siRNA; nucleotides, preferably polynucleotides, antibiotics or cytostatics. Preferably, cytostatics are selected from the group consisting of alkylating agents, anti-metabolites, anti-microtubule agents, topoisomerase inhibitors and cytotoxic antibiotics. Comprised are anti-metabolites, epothilones, nuclear receptor agonists and antagonists, anti-androgens, anti-estrogens, platinum compounds, hormones and antihormones, interferons and inhibitors of cell cycle-dependent protein kinases (CDKs), inhibitors of cyclooxygenases and/or lipoxygenases, biogeneic fatty acids and fatty acid derivatives, including prostanoids and leukotrienes, inhibitors of protein kinases, inhibitors of protein phosphatases, inhibitors of lipid kinases, platinum coordination complexes, ethyleneamines, methylmelamines, trazines, vinca alkaloids, pyrimidine analogs, purine analogs, alkylsulfonates, folic acid analogs, anthracendiones, substituted urea, methylhydrazine derivatives, in particular acediasulfone, aclarubicine, ambazone, aminoglutethimide, L-asparaginase, azathioprine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin dapsone, daunorubicin, dibrompropamidine, diethylstilbestrole, docetaxel, doxorubicin, enediynes, epirubicin, epothilone B, epothilone D, estramustine phosphate, estrogen, ethinylestradiol, etoposide, flavopiridol, floxuridine, fludarabine, fluorouracil, fluoxymesterone, flutamide fosfestrol, furazolidone, gemcitabine, gonadotropin releasing hormone analog, hexamethylmelamine, hydroxycarbamide, hydroxymethyl-nitrofurantoin, hydroxyprogesteronecaproate, hydroxyurea, idarubicin, idoxuridine, ifosfamide, interferon α, irinotecan, leuprolide, lomustine, lurtotecan, mafenide sulfate olamide, mechlorethamine, medroxyprogesterone acetate, megastrol acetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, bleomycin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, acriflavinium chloride, semustine, streptozocin, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, testolactone, testosterone propionate, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin. Preferably, antibiotics are selected from the group consisting of β-lactam antibiotics, β-lactamase inhibitors, monobactams, cephalosporins, carbapenems, lipopeptides, aminoglycosides, oxazolidinediones, glycylcyclines, polypeptide antibiotics, polyketides comprising tetracyclines or macrolides, ketolides, quinolones or sulfonamides. More preferably, the hydrophilic antipathogenic is a β-lactam antibiotic, an aminoglycoside or a lipopeptide. Even more preferably, the hydrophilic antipathogenic antibiotic is gentamicin. Preferably, the hydrophilic antipathogenic agent has a solubility of at least 10 ml per ml.

The second aspect of the invention provides a pharmaceutical composition comprising a carrier system of the first aspect of the present invention and a pharmaceutical acceptable excipient. In a preferred embodiment the pharmaceutical composition is provided in particles, meaning nano- or microparticles that can consist in whole or in part of the carrier system of the present invention or the other therapeutic agent(s). The pharmaceutical composition may contain the carrier system in a core surrounded by a coating, including but not limited to an enteric coating. In a further preferred embodiment the carrier system comprised in the pharmaceutical composition releases the carrier system with any order kinetics, zero order release, first order release or second order release. Preferably, the release is selected from the group consisting of rapid release, sustained release or delayed release. More preferably the carrier system is released from the pharmaceutical composition with a sustained release. Preferably, the pharmaceutical composition is a solid pharmaceutical composition selected from the group consisting of tablets, coated tablets, powder, granulate, pellets, capsules or effervescent tablets. More preferably, the pharmaceutical composition is a transdermal therapeutic system (TTS) selected from the group consisting of a matrix TTS with a rate controlling membrane, monolithic matrix TTS, modified TTS for volatile drug substances, reservoir matrix TTS, multilayer matrix TTS, matrix TTS with overlapping backing layer, micro reservoir matrix TTS. In another preferred embodiment, the pharmaceutical composition is a liquid composition selected from the group consisting of solutions, syrups, infusions, extracts, solutions for intravenous application or solutions for infusion.

The third aspect of the present invention provides a method for manufacturing a carrier system of the first aspect of the present invention comprising the steps of covalently linking the pathogen entry protein or a fragment thereof to the carrier of the present invention, either prior or after contacting said carrier with at least one hydrophilic antipathogenic agent.

The contacting of the carrier of the present invention with the hydrophilic antipathogenic agent serves the purpose of loading the hydrophilic antipathogenic agent, which can be a drug into or onto the carrier. Such hydrophilic drugs can be passively loaded into liposomes during the preparation process by using an aqueous solution containing the hydrophilic drug as hydrating medium. Passive loading of drugs can be achieved by a number of different techniques, including mechanical dispersion methods, solvent dispersion methods and detergent removal methods, as mentioned below. The mechanical dispersion method (MDM) involves two main steps, drying of lipids dissolved in an organic solvent, followed by mechanical dispersion of these dry lipids in an aqueous medium. In most cases, this is achieved by shaking. The hydrophilic drug can be incorporated into the aqueous medium, while the hydrophobic/lipophilic drug is dissolved together with lipids in the organic solvent. At this stage, various techniques can be used to modify the formed liposomes depending on the desired vesicle type and size. Sonication can be used to prepare SUVs, while extrusion can be used to prepare LUVs large unilamellar vesicles. The MLVs multilamellar vesicles can be prepared using techniques such as the freeze-thaw method or the sonicate-dehydrate-rehydrate method. In solvent dispersion method (SDM) lipids are first dissolved in an organic solvent, and then mixed with an aqueous medium, hydrophobic drug is dissolved with the lipids into the organic solvent and hydrophilic drug is dissolved in the aqueous medium, using two techniques to form liposomes. The ethanol injection technique, which requires a direct and rapid injection of lipids dissolved in ethanol to an aqueous medium through a fine needle. The ether injection technique involves a careful and slower injection of this immiscible organic solvent containing the lipid into an aqueous medium containing the drug at high temperature. The Detergent Removal Method involves the use of intermediary detergents in the lipid dispersion phase, such as cholate, alkyl-glycoside or Triton X-100. This detergent then associates with lipids to solubilize them and form micelles. In order to transform micelles into liposomes, the detergent must be removed. The removal of the detergent can be achieved by different techniques such as dialysis or gel chromatography. Active Loading of some chemical molecules such as lipophilic ions and weak acids and bases into liposomes can be achieved by various transmembrane gradients, including electrical gradients, ionic gradients or chemical potential gradients. All these concepts follow one principle that the free drug diffuses through the liposome. The diffusion requires two modification steps; one allows the drug to enter and the second inhibits membrane repermeation resulting in drug accumulation inside liposomes. Weak bases like doxorubicin and vincristine which coexist in aqueous solutions in neutral and charged forms have been successfully loaded into performed liposomes via the pH gradient method. Other approaches have also been employed in which an ammonium sulfate gradient or calcium acetate gradient were used as the driving force for loading of amphipathic drugs.

In a preferred embodiment the pathogen entry protein and/or at least one constituent of the carrier comprises an activatable group for covalent linking. Preferably, the activatable group is activated with an activating agent selected from the group consisting of carbodiimides, preferably N,N'-diisopropylcarbodiimide (DIC), N,N'-dicyclohexylcarbodiimide (DCC), more preferably N-(3-Dimethylaminopropyl)-N'-ethylcarbodiimide hydrochloride (EDC), succinimidylesters, preferably sulfosuccinimide, N-hydroxybenzotriazole, more preferably N-hydroxysuccinimide (NHS); maleidesters; and glutaraldehyde; triazine-based coupling reagents, preferably 4-(4,6-Dimethoxy-1,3, 5-triazin-2-yl)-4-methylmorpholiniumchloride (DMTMM).

It is preferred that the activating reagent is a mixture of N-(3-dimethylaminopropyl)-N'-ethylcarbodiimide hydrochloride (EDC) and N-hydroxysuccinimide (NHS), preferably EDC in a concentration of 5, 10, 15, 20, 25, 30, 35, 40, 45, 50, 55, 60, 65, 70, 75, 80, 85, 90, 95, 100 mM, more preferably 48 mM and NHS in a molar concentration range of 1, 2, 3, 4, 5, 6, 7, 8, 9, 10, 11, 12, 13, 14, 15, 16, 17, 19, 20, 25, 30, 35, 40, 45, 50 mM, more preferably 19 mM.

In a fourth aspect of the present invention the carrier system according to the first aspect or the pharmaceutical composition according to the second aspect are provided for the use as a medicament. In a preferred embodiment, the pharmaceutical composition or the carrier system are used for the treatment or prophylaxis of infectious diseases. It is preferred that the infectious diseases are systemic infections, preferably nosocomial infections, more preferably elicited by *Staphylococcus* and/or vancomycin-resistant *Enterococcus* (VRE). In another preferred embodiment the infectious disease is an infection with a bacterium, which persists/ replicates (sequesters) in non-phagocytic cells, preferably a Gram-negative bacterium, more preferably *Chlamydia, Coxiella burnetti, Ehrlichia, Rickettsia, Legionalla, Salmonella, Shigella* or *Yersinia*, or a Gram-positive bacterium, more preferably *Mycobacterium leprae* or *Mycobacterium tuberculosis*.

Other infections that can be treated with the carriers systems or pharmaceutical compositions of the present invention comprise Leprosy, Leishmaniasis, Malaria, Tuberculosis, Dengue and severe dengue, Buruli ulcer, Hepatitis B, Hepatitis E, Hepatitis C, Hepatitis A, Trypanosomiasis, Human African (sleeping sickness), Poliomyelitis, Measles, Crimean-Congo haemorrhagic fever, Meningococcal meningitis, Ebola haemorrhagic fever, Cholera, Monkeypox, Influenza, Rift Valley fever, Smallpox.

BRIEF DESCRIPTION OF THE FIGURES

The following figures are merely illustrative of the present invention and should not be construed to limit the scope of the invention as indicated by the appended claims in any way.

FIG. 1 shows the viability of HEp-2 (a) and non-polarized (b) and polarized (c) Caco-2 cells after incubation with uncoated as well as invasin-coated liposomes. No significant difference in cell viability was observed for uncoated liposomes or liposomes coated with the bacterial surface protein, invasin compared to non-treated control cells.

FIG. 2.2: Invasin-coated liposomes promote tight adhesion to human epithelial cells II Invasin coating resulted in a significant increase in cellular adhesion of about 2-5 (physically adsorbed InvA) and 32-38 fold (covalently-linked InvA) relative to control liposomes (FIG. 2-2). In presence of bacteria, a decrease of InvA-promoted adhesion of liposomes was observed. For instance, 2- and 6-fold decrease of cell-associated liposomes was detected when InvA-expressing bacteria were added simultaneously or prior to liposomes. This indicates that bacteria and liposomes use the same adhesion mechanism and compete for $\beta_1$-interin receptors.

Figure 1:
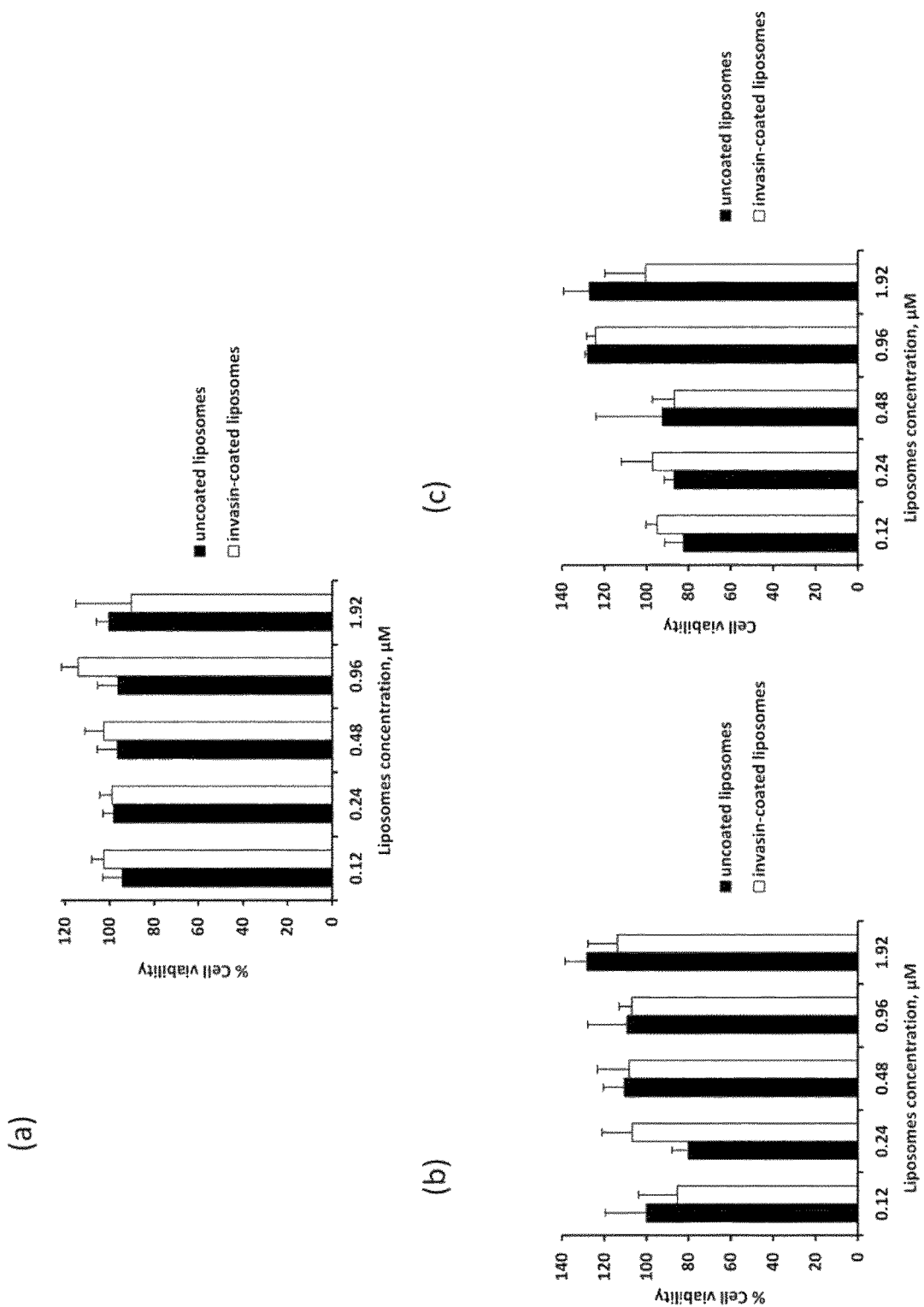
FIG. 1: Liposome preparation, characterization and protein covalent coupling andcell viability study Monodisperse phospholipid fluorescent liposomes containing carboxylic groups were successfully prepared. Cholesterol in the bilayer was incorporated as a membrane stabilizer increasing the glass transition temperature. Liposomes were covalently coated with invasin or bovine serum albumin (BSA) without any observed aggregation. Size diameter of uncoated liposomes was around 142.5 nm, with a polydispersity index (PDI) of approx. 0.03. The zeta potential was in the range of −20 to −43 mV. Increase in zeta potential was observed upon protein coating indicating higher stability due to steric hindrance by the protein corona. The protein coating efficiencies as judged by surface protein quantification using bicinchoninic acid (BCA) assay and western blot assay were comparable. Potential nanoparticle-dye interferences must be first considered to avoid false-positive and false-negative results. No interference was observed on measuring luminescence of ATP standards in presence of liposomes.

To analyze the capacity of InvA-coated liposomes to promote uptake into human cells, we investigated the number of intracellular uncoated (b, d) and invasin-coated (a, c) liposomes after 1 h (upper panel) and 4 h (lower panel) incubation of the liposomes with HEp-2 cells at 37° C. using confocal-multiphoton microscopy. Representative confocal images are shown in FIG. 3-1.

Figures 1, 2:
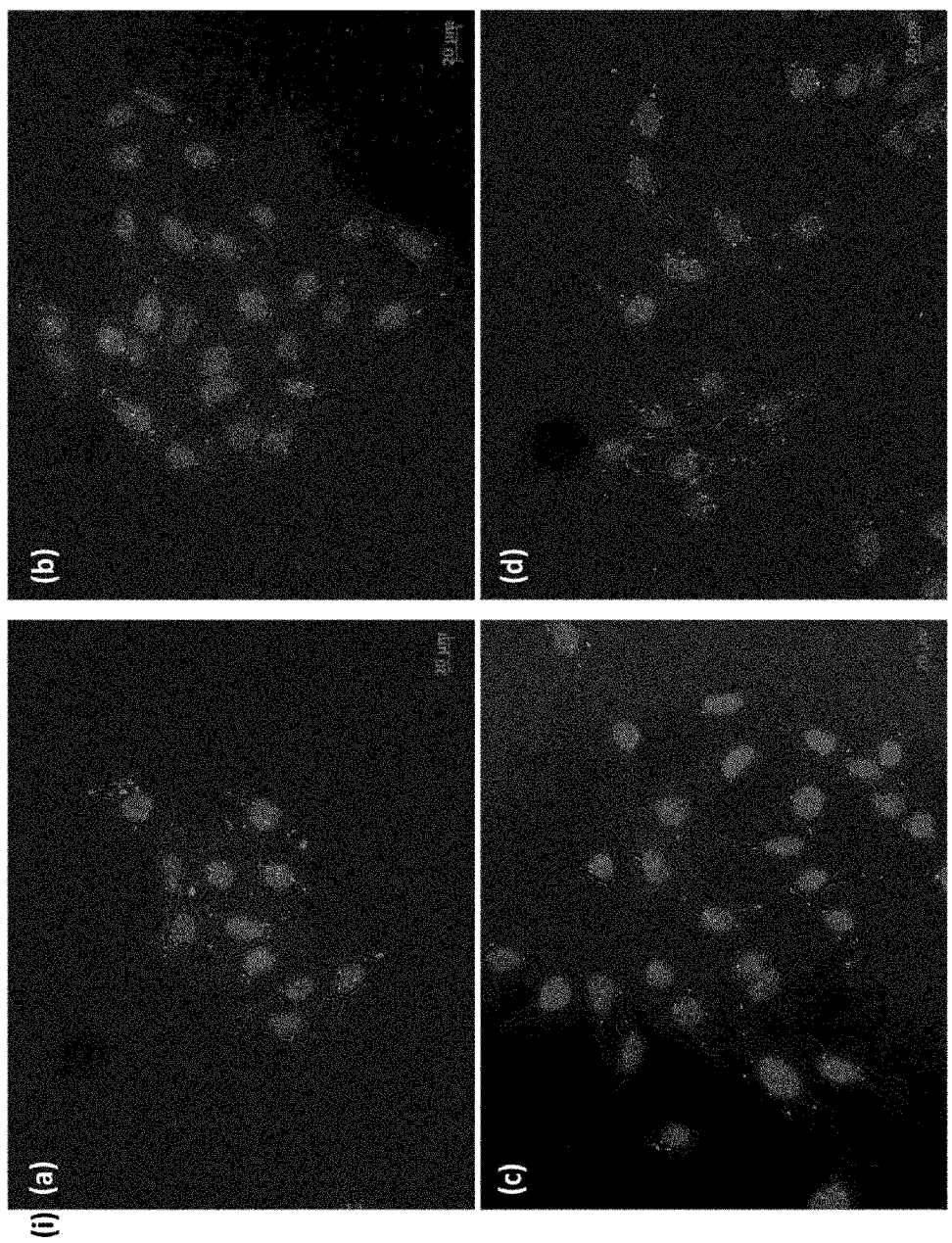
FIG. 2.1: Invasin-coated liposomes promote tight adhesion to human epithelial cells I Challenge experiments were designed to study the ability of invasin-coated (via physical adsorption (a) or covalent attachment (b)) liposomes to mediate adhesion to HEp-2 cells in presence of InvA-expressing *Yersinia pseudotuberculosis* acting on $\beta_1$-interin receptors. To do so, liposomes were added to the cells at 25° C., conditions where only cell adhesion but no bacterial invasion into host cells is observed. Two experimental sets were included in which the bacteria were added simultaneously or prior to the liposomes. This is in comparison to healthy state where cells were not exposed to bacteria. Control liposomes with adsorbed (c) or covalently-linked (d) BSA did not show significant adhesion to HEp-2 cells indicated via fluorescence imaging (FIG. 2-1-2.2).
Figure 2:
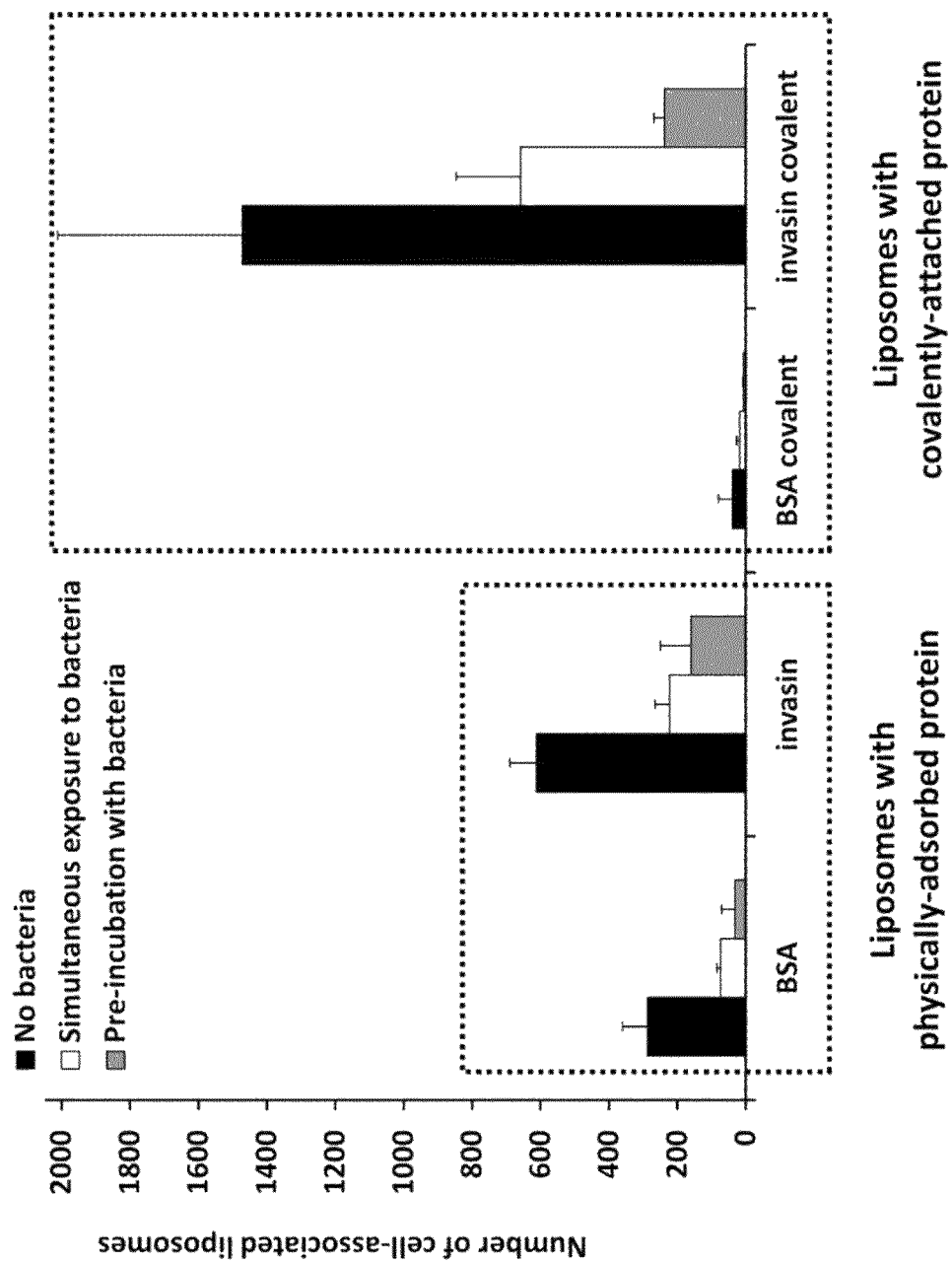
Figures 1, 3:
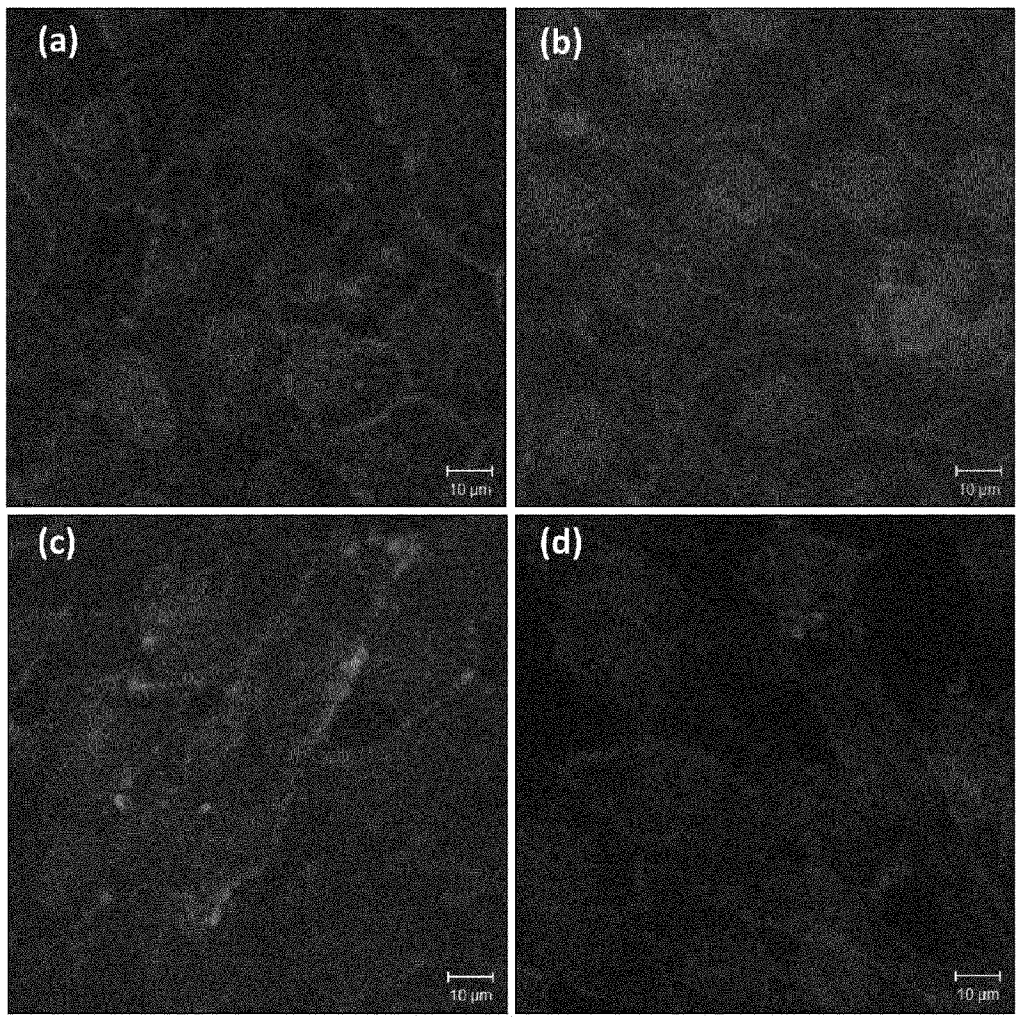
FIG. 3.1: Cell uptake kinetics and internalization mechanism into HEp-2 cells I
Figures 2, 3:
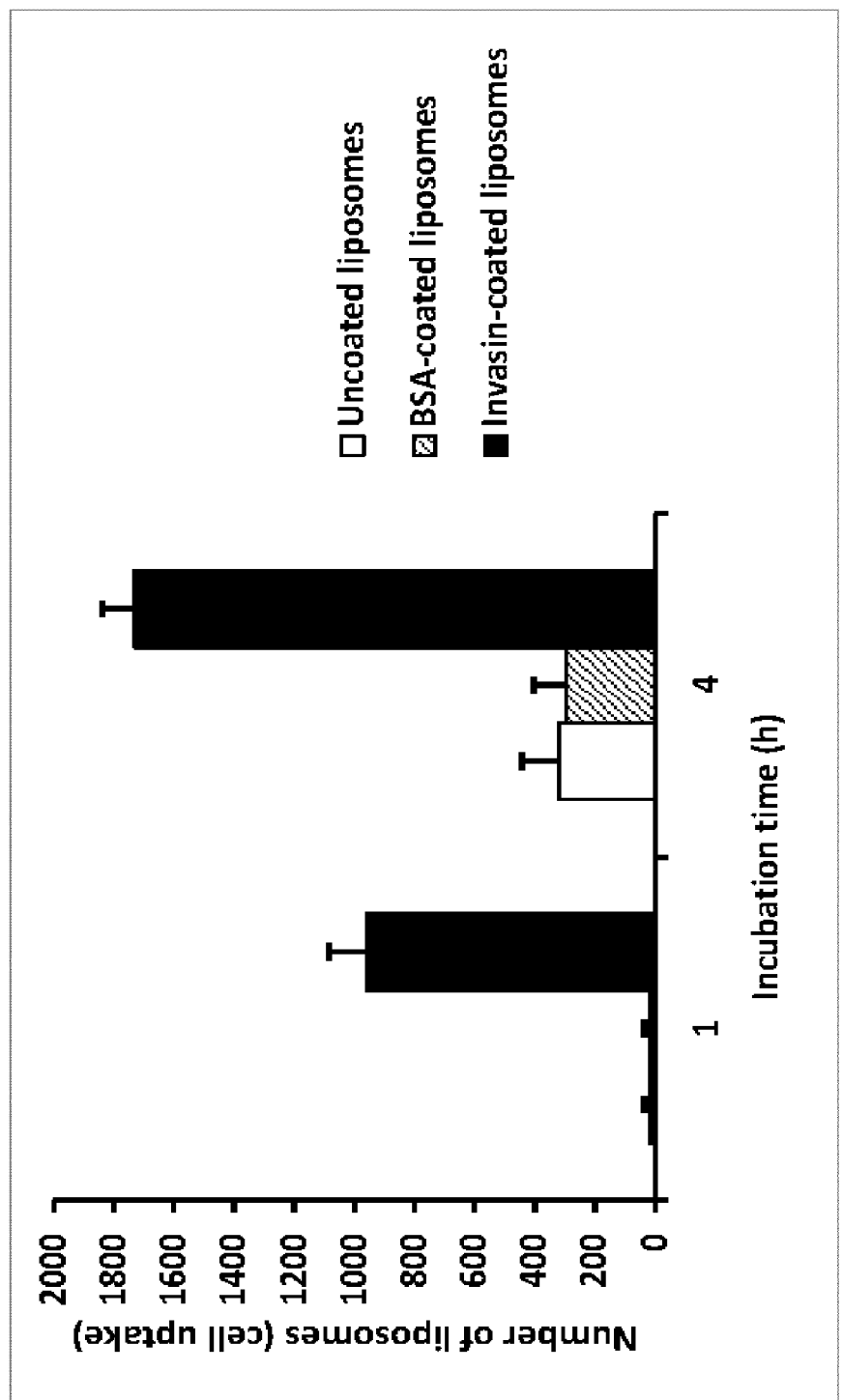

FIG. 3.2: Cell uptake kinetics and internalization mechanism into HEp-2 cells II Results of image analysis of the sequestered z-stacks are demonstrated in FIG. 3-2. No significant cell uptake was observed for uncoated liposomes. Cell uptake was induced upon invasin coupling and the number of intracellular liposomes increased significantly over time. Notably, the uptake efficiency of uncoated liposomes and BSA-coated liposomes were similar and usually very low (FIG. 3-2). Therefore, only uncoated liposomes were used as control in all following uptake experiments.

FIG. 4: Uptake kinetics into HEp-2 cells

To determine uptake kinetics into HEp-2 cells, cell uptake into living cells was tracked over 4 h (FIG. 4$i$). The number of intracellular uncoated and InvA-coated liposomes increased over time. However, the overall number of internalized InvA-coated liposomes was significantly higher at each time point. Moreover, the average uptake rate was about 7-fold higher for invasin-coated (507 liposomes/h) relative to uncoated liposomes (70 liposomes/h) (FIG. 4$ii$). More time points in the first hour were not possible to realize in live cell imaging. This is to avoid continuous laser exposure of the treated cells on z-sectioning which may result in photobleaching and inaccuracy of the results. Therefore, to get more information on the first hour, 1 h fixed-cells experiments were performed similarly. Combining all time points, one could divide the uptake of invasin-coated liposomes into three phases: initial liposome uptake characterized by a fast exponential uptake rate leading to a plateau (saturation) which is typical for receptor-mediated uptake, followed by a process characterized by linear uptake rate.

Figure 5:
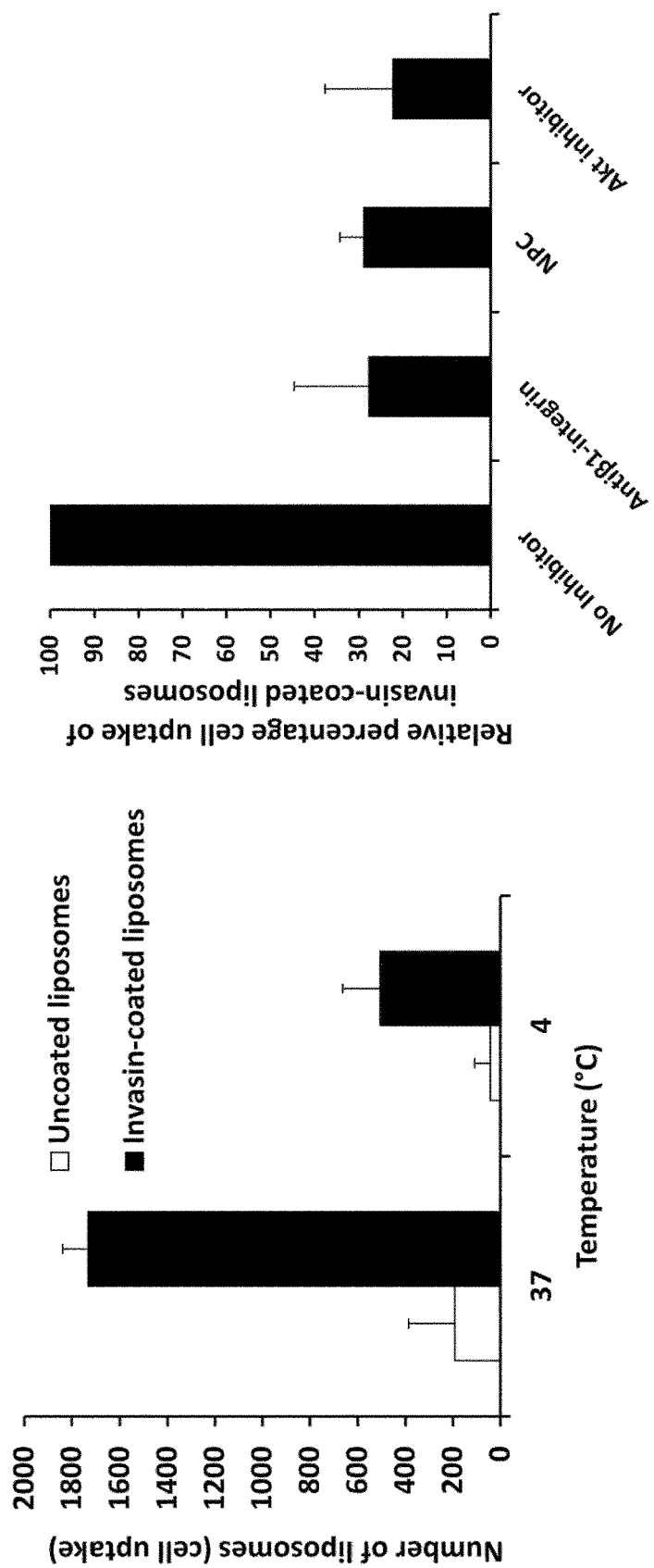
Figure 6:
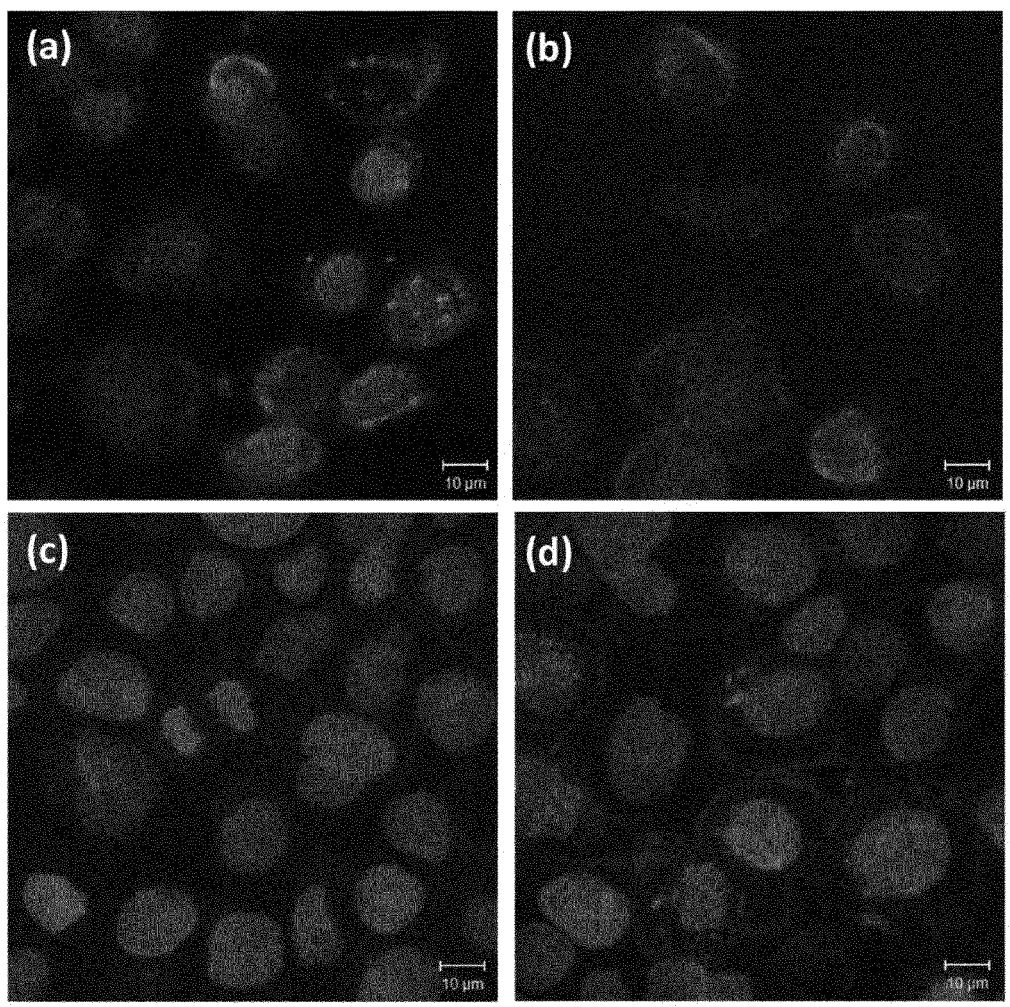
Figure 7:
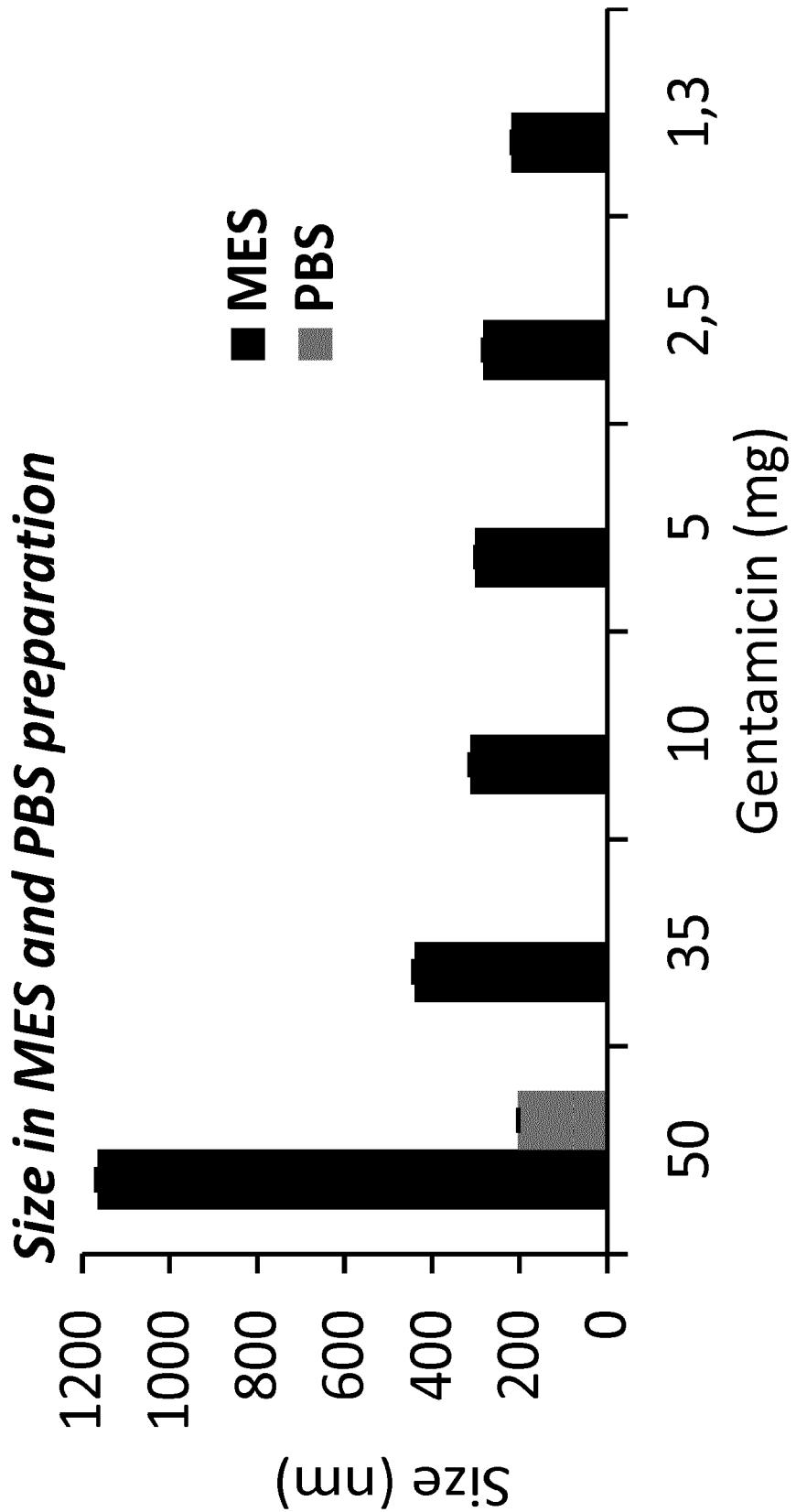

FIG. 5: Further characterization of the uptake mechanism in HEp-2 cells

Figure 8:
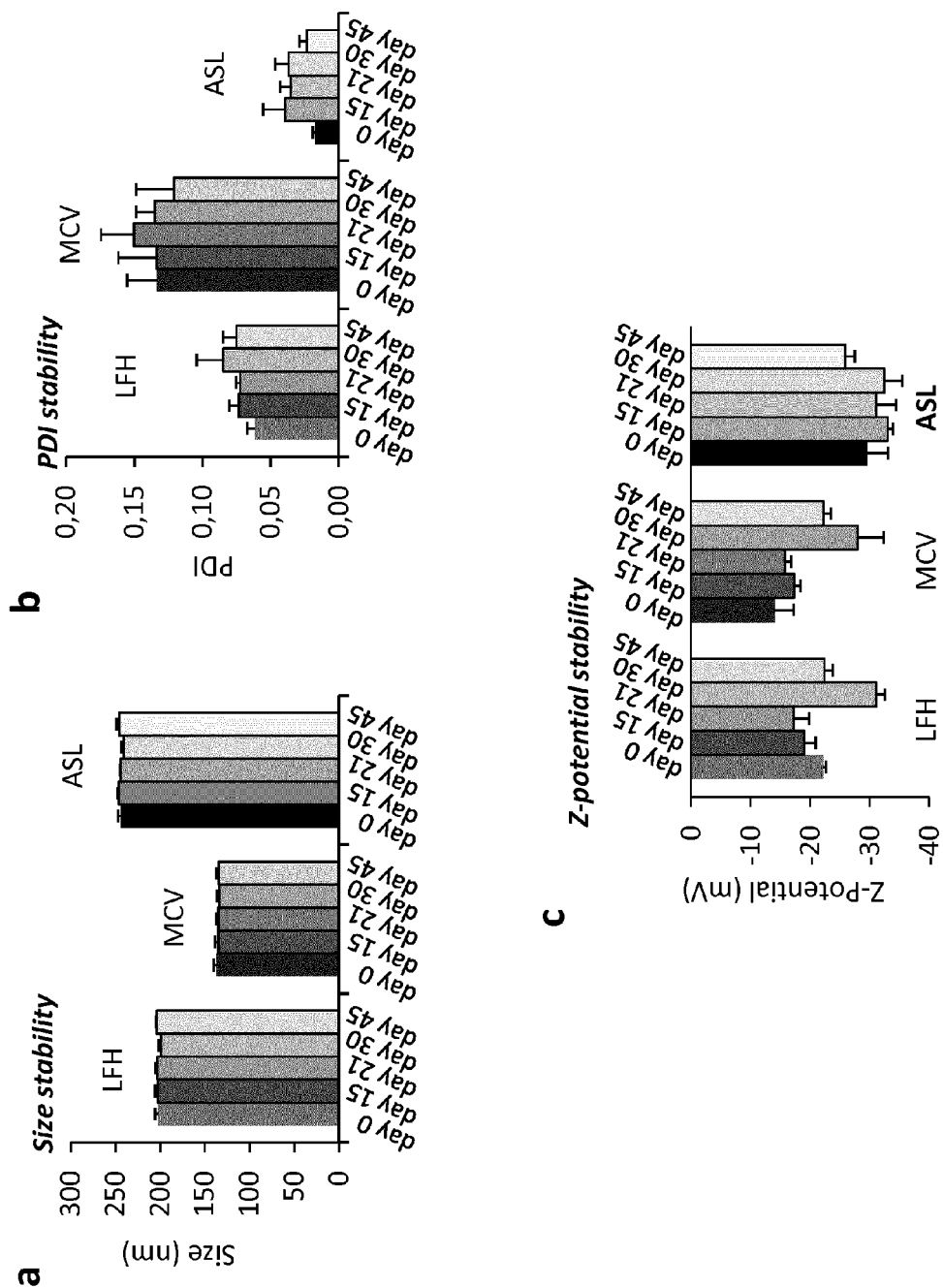

To further characterize the uptake mechanism, HEp-2 cells were incubated with uncoated or invasin-coated liposomes at 4° C. and 37° C. to determine relative liposomal uptake. At 4° C., energy-dependent uptake mechanisms (endocytosis) are greatly reduced. No significant difference in cell uptake of uncoated liposomes was observed at 37° C. when compared to 4° C. Reduction in temperature was however accompanied by significant decrease in cell uptake of invasin-coated liposomes (FIG. 5-1). Yet, still some invasin-coated liposomes were taken up at such low temperature, 4° C. Finally, to verify whether cell uptake mechanism of invasin-coated liposomes is a receptor-specific ($62_1$-integrin) mechanism, cell uptake inhibition experiments were conducted. First, anti-integrin $\beta_1$-antibody was added to HEp-2 cells before the addition of InvA-coated liposomes. As shown in FIG. 5-2, a significant reduction of liposome uptake was observed in the presence of the antibody, indicating that the InvA-triggered uptake of the liposome occurs via β-integrin receptors. Several inhibitors proven to reduce the InvA-triggered cell uptake of *Yersinia pseudotuberculosis*, Akt inhibitor VIII and NPC-15437, were examined. The serine threonine kinase Akt becomes activated in response to many $\beta_1$-interin-initiated signaling processes. Activation of Akt is required for the invasin-mediated uptake of *Y. pseudotuberculosis*. Also protein kinase C (PKC) was shown to be implicated in the InvA-triggered uptake pathway. The selective PKC inhibitor NPC-15437, interacting at the regulatory domain of the enzyme, was effective in blocking the invasin-mediated bacterial invasion Inhibition experiments clearly indicate $\beta_1$-interin receptor specific uptake whereas cell entry of invasin-coated liposomes was reduced to 22-29% compared to the untreated control (FIG. 5-II).

FIG. 6: Targeting of inflamed epithelium: Non-polarized versus polarized Caco-2 cells InvA-mediated liposomes targeting to $\beta_1$-integrin receptors could be exploited to develop drug delivery tools directed against an inflamed intestinal epithelium. Previous studies have demonstrated that $\beta_1$-integrin receptors are not expressed on the apical side of enterocytes of the intestinal epithelial layer. Only the small number of M cells exposes this class of cell surface receptors on the apical side and are preferentially targeted by *Yersinia pseudotuberculosis*. However, under specific conditions, for instance during intestinal inflammation (e.g. inflammatory bowel disease), $\beta_1$-integrins become more accessible on the apical side of the enterocytes. In order to mimic this situation liposome uptake into non-polarized and polarized Caco-2 cells was studied. Cells at 50% confluency express $\beta_1$-integrins on their apical surface, whereas cells grown to over 90% confluency reduce the expression of the invasin receptor. To investigate whether invasin-coated liposomes are preferentially targeted to non-polarized $13_1$ integrin surface-exposing cells, InvA-coated and non-coated liposomes were used to challenge the non-polarized and polarized Caco-2 cells for 8 h. Only uptake of invasin-coated liposomes into sub-confluent Caco-2 cells was observed (FIG. 6*a*). Interestingly, some adhesion of InvA-coated liposomes on polarized cells was observed (FIG. 6*c*). However, this weak attachment was not sufficient to promote cell uptake. No uptake was observed for control uncoated liposomes into Caco-2 cells regardless of the confluency level (50% confluency FIG. 6*b*, 90% confluency FIG. 6*d*), demonstrating that the uptake process is specific for InvA.

FIG. 7: Size of gentamicin-containing liposomes

Liposomes containing gentamicin were firstly prepared by the lipid film hydration (LFH) method, by hydration of the lipid film with morpholine-4-ethanesulfonic acid hydrate (MES) buffer of pH 6 containing 10 mg/ml of gentamicin. Under these conditions, liposomes with a size of approximately 1000 nm were obtained. This size range does not fit with the desired size of ~200 nm, as the cellular uptake is considered to be higher when particles are smaller. However, liposomes which were prepared in MES buffer without the addition of gentamicin showed an average size of ~200 nm. Interestingly, when the amount of gentamicin added to the MES buffer was reduced, size of liposomes also decreased in a proportional manner with the amount of gentamicin. Therefore, pH of the hydration buffer was increased, to reduce the electrostatic interaction between liposomes and gentamicin, by instead using phosphate buffered saline (PBS) buffer of pH 7.4 which is close to the pKa of gentamicin (pKa=8.2). Using PBS buffer and 10 mg/ml of gentamicin, it was possible to obtain liposomes of 202.46+/−5.72 nm, an acceptable size.

FIG. 8: Colloidal characteristics of liposomes

In order to investigate the colloidal stability of liposome preparations, the size, PDI and zeta potential of liposomes prepared using three different methods were monitored over time. The size of liposomes prepared using the LFH method, the microencapsulation vesicle (MCV) method and the ammonium sulfate liposome (ASL) preparation method was found to be stable for a period of 45 days (FIG. 8*a*). For the PDI, all the three preparations showed an increase in PDI values, but never above a value of 0.2 (FIG. 8*b*). Concerning the zeta potential, the values of this parameter became more negative over the measured 45 day period (−20 mV to −35 mV) for LFH, MCV and ASL liposomes (FIG. 8c).

Figure 9:
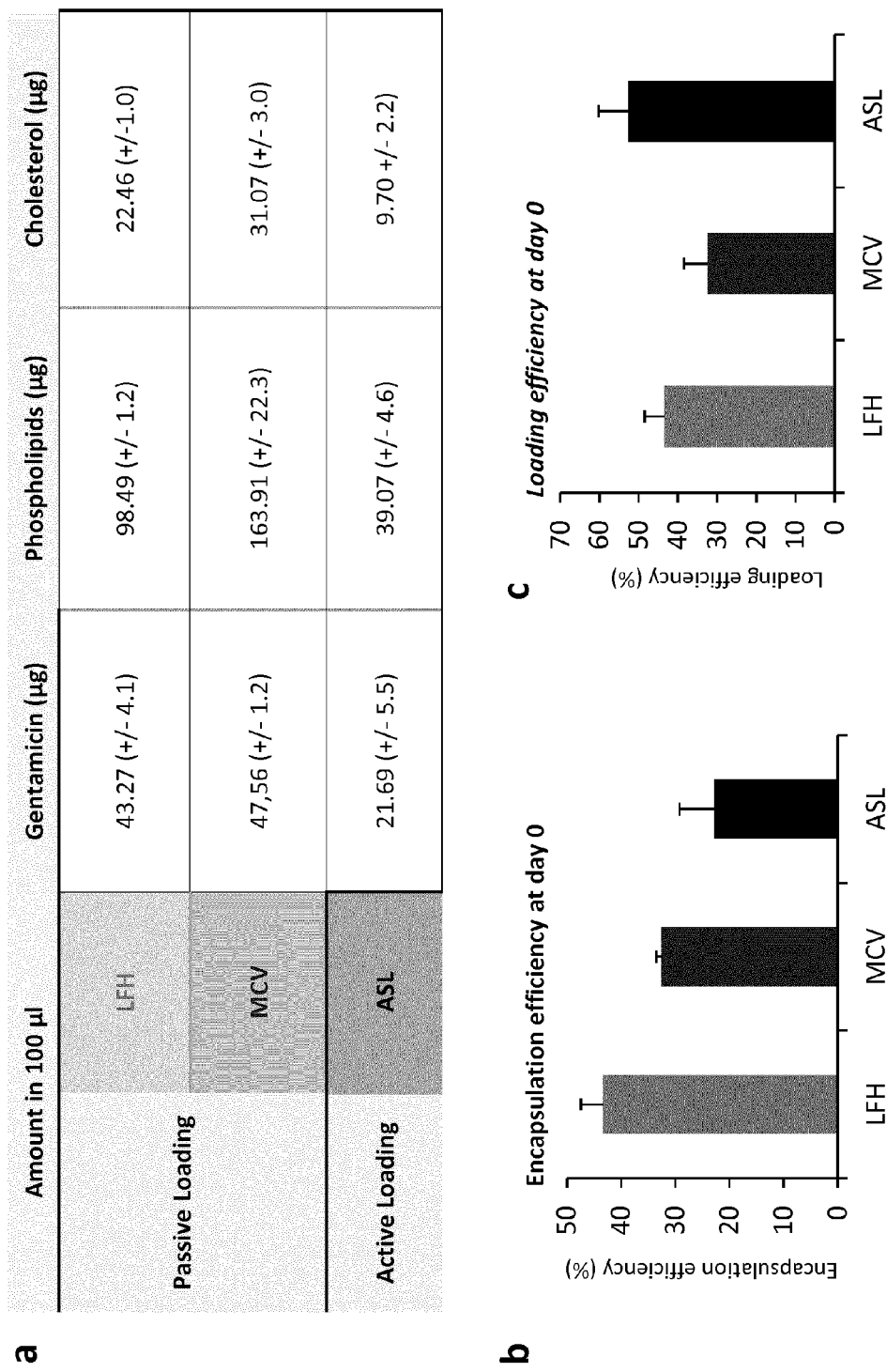

FIG. 9: Encapsulation and loading efficiency

The encapsulation efficiency is the amount of gentamicin which was encapsulated into liposomes versus the initial amount of gentamicin used for the preparation. LFH liposomes showed the highest encapsulation efficiency of 43.27%, whereas the encapsulation efficiency of MCV liposomes was 33.29%. 22.75% of the initially added gentamicin was found in ASL liposomes (FIG. 9b). Loading efficiency is also a parameter used to assess the efficiency of a drug loading into liposomes which depends on the actual (FIG. 9a) and the initial amount of gentamicin, phospholipids and cholesterol. In contrast to the encapsulation efficiency, the loading efficiency of ASL liposomes was found to be the highest among the three preparations 52.52%, while LFH liposomes showed 43.67% loading efficiency. 31.57% loading efficiency was measured in MCV liposomes (FIG. 9c).

Figure 10:
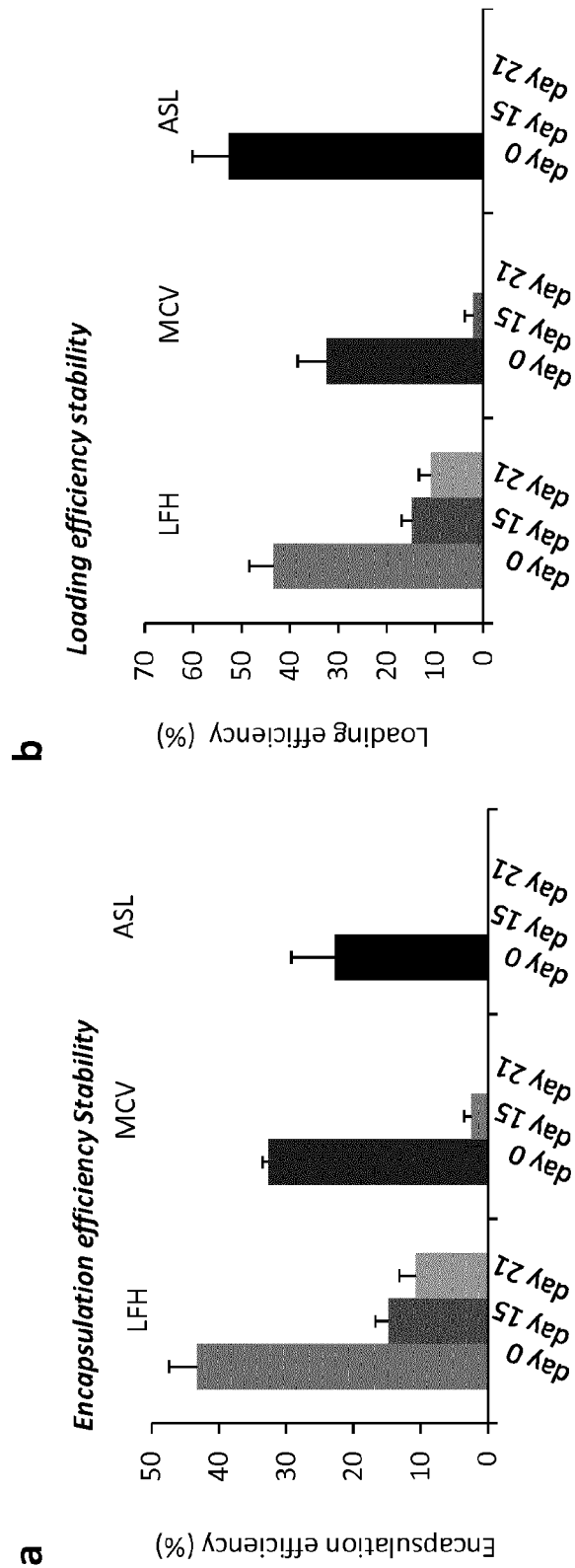

FIG. 10: Chemical stability of liposomes

Stability was assessed in terms of size, PDI and zeta potential, as mentioned above, but also in terms of incorporated gentamicin. Encapsulation efficiency was evaluated (FIG. 10a) and the loading efficiency (FIG. 10b) of LFH, MCV and ASL liposomes on the day of preparation (day 0), as well as day 15 and day 21 after preparation. At day 0 the encapsulation efficiency ranged from 20 to 45% for the three preparations and the loading efficiency was found to be between 30 and 60%. After 15 days, both the encapsulation and loading efficiency of LFH liposomes had decreased to approximately 15%, and only 5% encapsulation efficiency and 2% loading efficiency were found for MCV liposomes. Surprisingly, the ASL preparation did not contain any gentamicin after 15 days. At day 21, only the LFH liposomes were seen to retain gentamicin (11% for both encapsulation and loading efficiencies). MCV and ASL liposomes did not contain any detectable gentamicin after 21 days.

Figure 11:
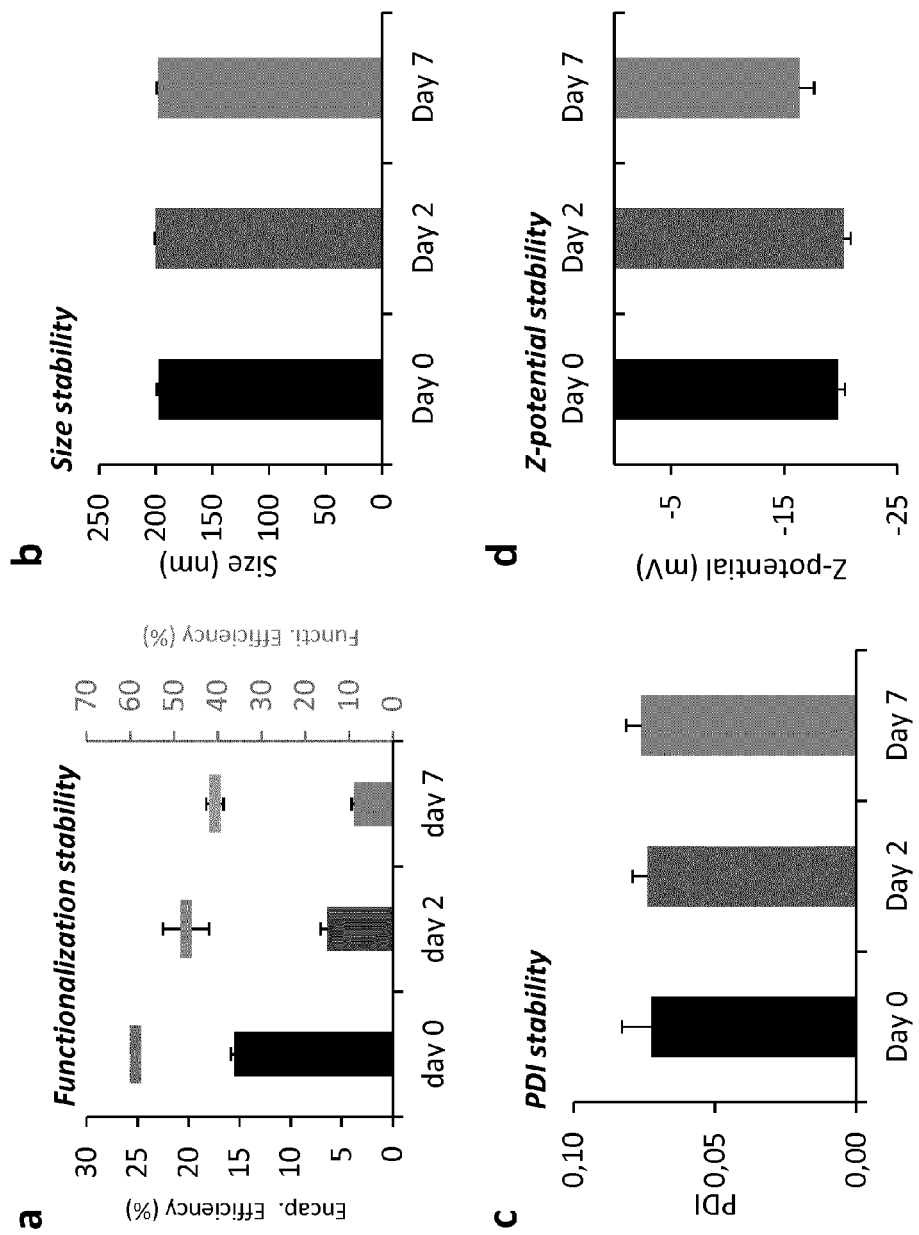

FIG. 11: Stability of gentamicin-loaded, invasin-functionalized liposomes

For the invasin functionalization, the same conditions as used for preliminary BSA functionalization (two washing steps) were applied. The functionalization efficiency using LFH liposomes and invasin and measured via the BCA assay was approximately 60%, and as expected, the encapsulation efficiency was approximately 15%. These functionalized liposomes were subjected to a short-term stability study (designed to reflect the estimated duration of later cell experiments), where at day 0, day 2 and day 7 of storage the size, PDI, zeta potential, encapsulation efficiency and functionalization efficiency of liposomes was tested. After 2 and 7 days of storage, the size, PDI and zeta potential showed no appreciable change and stayed within the desired ranges (FIG. 11b, c, d). Whereas, the encapsulation efficiency at day 2 decreased to 7% and decreased even more to 5% after 7 days. The functionalization efficiency was also reduced after 2 days to 50%, and further to 40% after 7 days (FIG. 11a).

FIG. 12: Invasin functionalization efficiency measurement

The functionalization efficiency of invasin was measured by quantifying the amount of invasin in the liposomal preparation using the BCA assay. The results obtained with the BCA assay were then confirmed with SDS-PAGE using standard solutions of pure invasin and suspensions of invasin-functionalized gentamicin-containing liposomes (FIG. 12a). Results showed that the difference in measured functionalization efficiency between both methods was approximately 7%, which is to be expected given that the SDS method is more a qualitative technique than quantitative (FIG. 12b).

Figure 13:
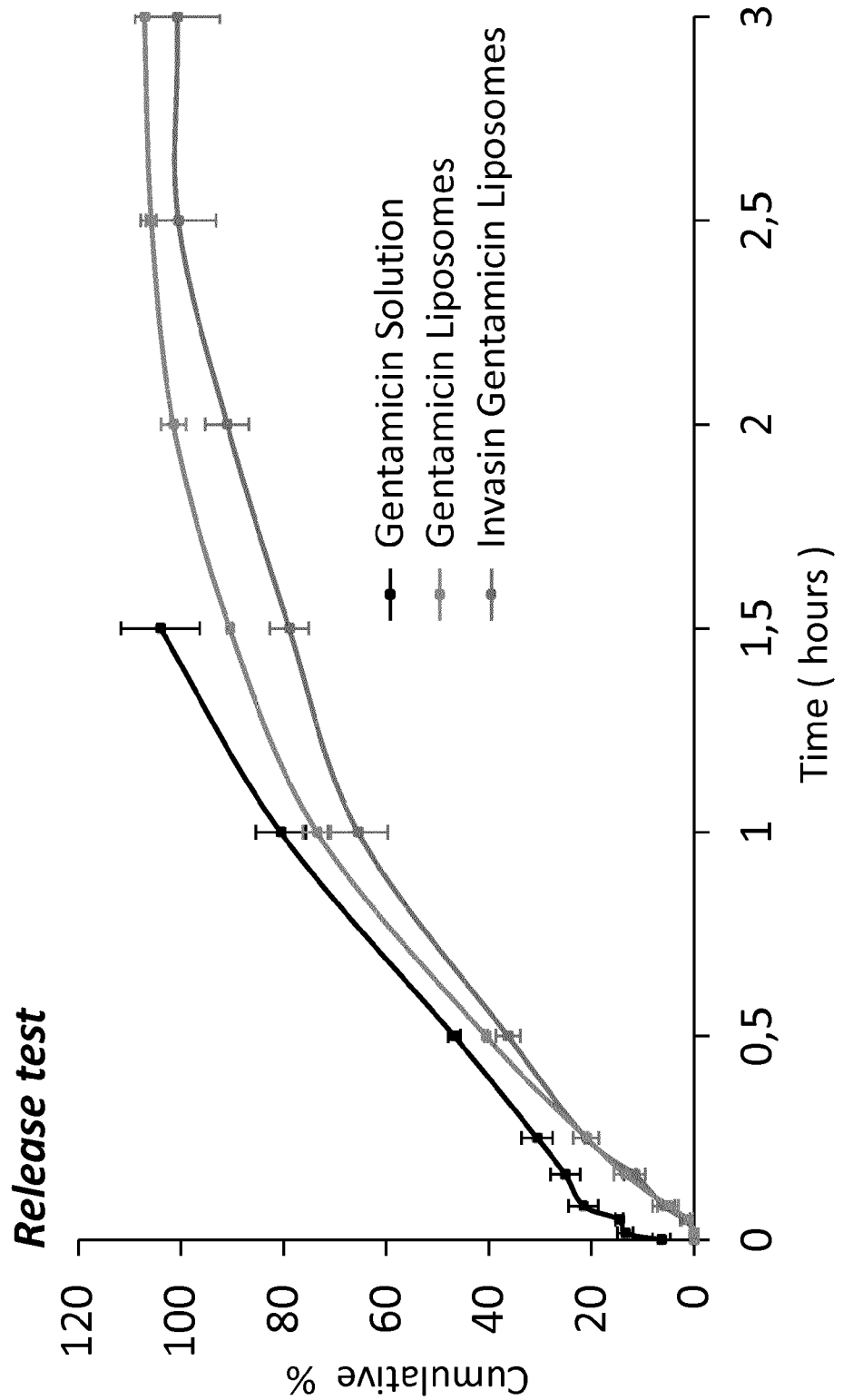

FIG. 13: Release test

Liposomes, invasin-functionalized or non-functionalized, were subjected to release testing to evaluate their ability to release the encapsulated gentamicin under a mechanical stress at 37° C. over a period of 3 h, using a dialysis membrane setup. A solution of gentamicin with same concentration to that contained within liposomes was used as a control. Cumulative percentages of gentamicin release values over 3 h, determined for three independent samples of each formulation, are shown in (FIG. 13). The gentamicin solution was detectable within the bulk release medium within 1 min, whereas gentamicin released from liposomes was not detectable until 3 min following initiation of the release test. After 1.5 h the gentamicin solution was shown to have completely permeated through the 10.000 MWCO cellulose membranes. In the case of liposomal gentamicin, complete release was achieved after 2.5 h, and both invasin-functionalized and non-functionalized liposomes showed similar kinetics of gentamicin release.

Figure 14:
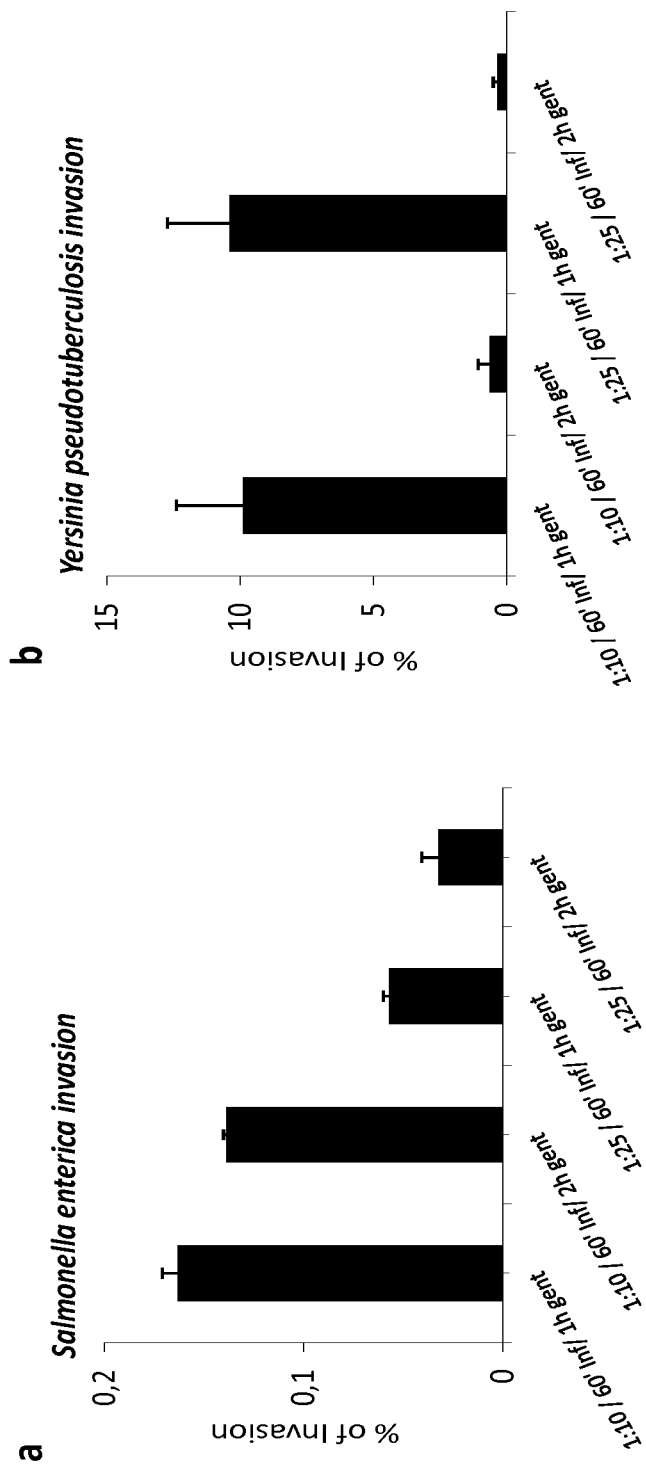

FIG. 14: Optimization of conditions for invasion assays

Epithelial cells of the HEp-2 cell line were infected with *Salmonella enterica* and *Yersinia pseudotuberculosis* using various different conditions, in order to determine the optimal parameters for testing the efficiency of invasin-functionalized liposomes loaded with gentamicin. The infection load of *Salmonella enterica* and *Yersinia pseudotuberculosis*, was assessed by using different multiplicities of infection (MOI) 1:10, 1:25, each with 1 h of infection time, and followed by either 1 h or 2 h of treatment with pure gentamicin in order to kill any remaining extracellular bacteria. Results showed that the 1:10 MOI and 1 h extracellular gentamicin treatment had the highest invasion rate for *Salmonella enterica* (FIG. 14a). For *Yersinia pseudotuberculosis*, the MOI of 1:25 and 1 h gentamicin treatment showed a similar invasion rate to that of the 1:10 MOI (FIG. 14b). Thus, for the conditions for liposomal invasion tests prior to the addition of liposomes, a 1:10 MOI and 1 h of pure gentamicin treatment was chosen for *Salmonella enterica*, and a 1:25 MOI with 1 h of pure gentamicin treatment was chosen for *Yersinia pseudotuberculosis*.

Figure 15:
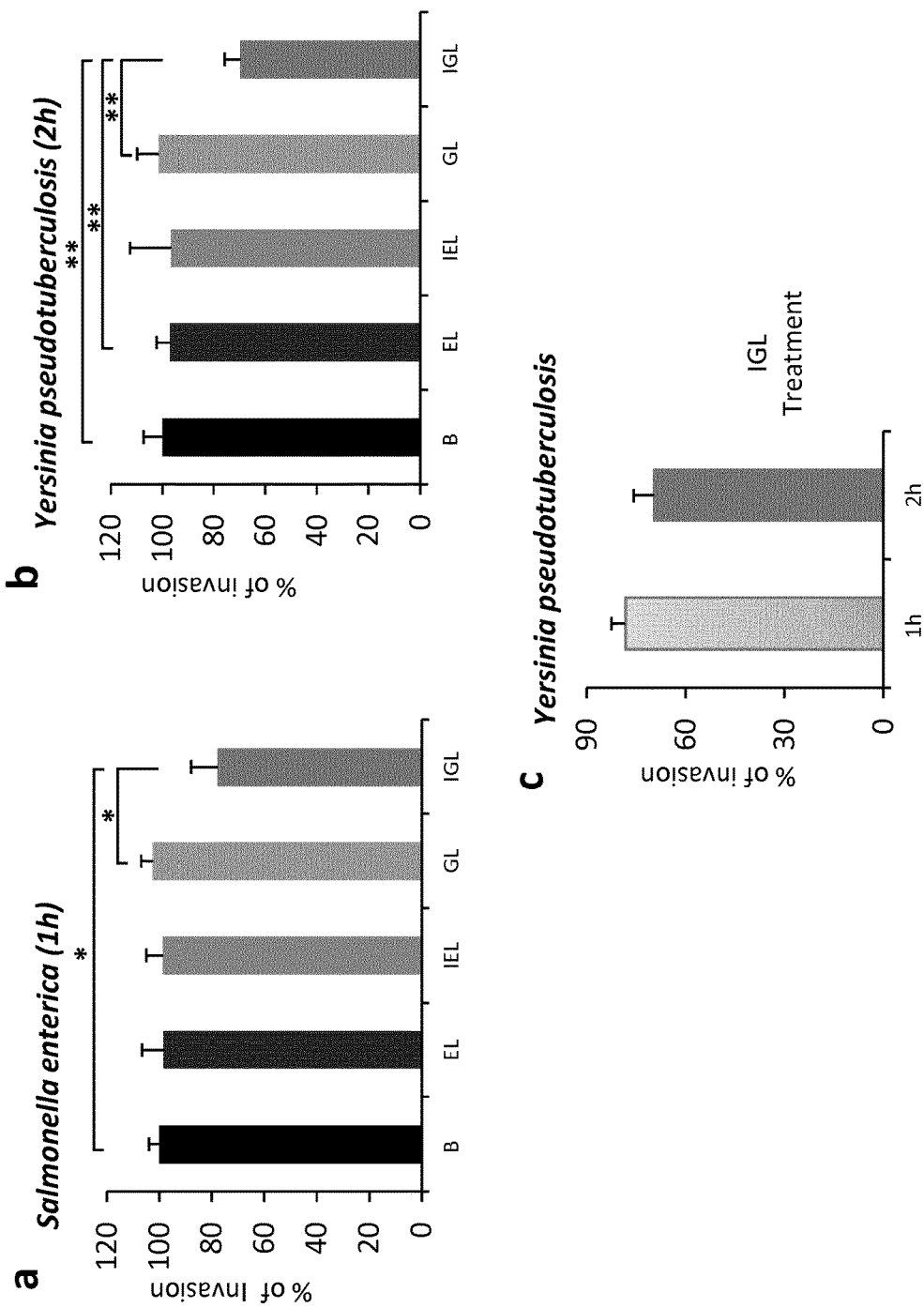

FIG. 15: Invasion assay—liposomal treatment of infected HEp-2 cells

As mentioned, gentamicin permeates very poorly through biological membranes due to its hydrophilicity. This limits its bactericidal action against intracellular bacteria. In this study, we tried to encapsulate gentamicin into liposomes and functionalize these particles with invasin to facilitate the interaction and the penetration of the liposomal gentamicin to infected HEp-2 cells. *Salmonella enterica* and *Yersinia pseudotuberculosis* were used to infect HEp-2 cells because they are intracellular bacteria. After infection with Salmonella enterica or *Yersinia pseudotuberculosis*, followed by incubation with pure gentamicin to kill extracellular bacteria, HEp-2 cells were treated with invasin-functionalized gentamicin-loaded liposomes (IGL) for 1 h. In *Salmonella enterica*-infected cells, we observed that treatment with IGL reduced significantly the intracellular bacterial load by 22%, when compared infected cells which were left untreated (blank −B) or which were treated with non-functionalized gentamicin-loaded liposomes (GL) (FIG. 15a). In the case of HEp-2 cells infected with *Yersinia pseudotuberculosis*, treatment with IGL also reduced the infection by 22% in comparison to control groups (FIG. 15c). Increasing the incubation time of IGL with infected cells from 1 h to 2 h resulted in a significant reduction of 30% in the infection load when compared to untreated cells as well as cells treated with empty liposomes (EL), invasin-functionalized empty liposomes (IEL) and GL. (FIG. 15b). The concentration of gentamicin used in the liposomal treatment was 50 mg/ml in 1.3 mM liposomes.

EXAMPLES

The following examples are for illustrative purposes only and do not limit the invention described above in any way.

Example 1: Lipid Film Hydration Method

Liposomes were prepared by the lipid film hydration (LFH) technique as previously described by Bangham and his colleagues. In a round bottomed flask and in a molar ratio of (6:0.6:3), DPPC, DPPE and cholesterol respectively were dissolved in 5 ml of chloroform: methanol (2:1). 10 µg/ml of Rh-DPPE was added to color the liposomes for the imaging experiment. The flask was then connected to a rotary evaporator (Buchi Switzerland) equipped with a vacuum controller set at 200 mbar, and a heating bath set at 70° C. for 1 h. This led to the formation of a dry lipid film. The vacuum controller was then set at 40 mbar for another 30 min to remove any residual traces of the organic solvent. A 5 ml volume of gentamicin solution (10 mg/ml) in phosphate buffered saline (PBS pH=7.4) was added to the dry lipid film and rotation was recommended at 50° C. for 1 h, leading to the hydration of the lipid film and the formation of MLV. The resulting MLV were then extruded 10 times through 200 nm pore size polycarbonate membranes (Polycarbonate track-Etch Membrane, Sartorius Germany) at 70° C. The final dispersion of liposomes was diluted 1:10 and stored at 4° C. In detail, 1,2-dipalmitoyl-sn-glycero-3-phosphocholine (DPPC) (Lipoid GmbH, Ludwigshafen, Germany), cholesterol (Sigma-Aldrich, Steinheirn Germany) and 1,2-dihexadecanoyl-sn-glycero-3-phosphoethanolamine-N-(glutaryl) (sodium salt) (DPPE) (Avanti Polar Lipids, Inc., Alabaster, USA) in a molar ratio of 6:3:0.6 were dissolved in 5 ml chloroform/methanol mixture, 2:1. A 100 µl of 0.5 mg/ml chloroformic solution of the fluorescent dye 1,2-dipalmitoyl-sn-glycero-3-phosphoethanolamine-N-(lissamine rhodamineB sulfonyl) (ammonium salt) (Rh-DPPE) (Avanti Polar Lipids, Inc., Alabaster, Ala., USA) was added. The final lipid mixture (19.2 mM) was dried in a rotary evaporator (Büchi, Essen, Germany) at 70° C. 200 mbar and 145 rpm for 1 h to form a thin uniform lipid film. Complete evaporation of the remaining solvents was achieved by further heating at the same temperature under a pressure of 40 mbar with 145 rpm for further 30 min. The lipid film was then hydrated with 5 ml PBS buffer, pH 7.4 at a speed of 55 rpm for 1 h at 50° C. Unilamellar liposomes were prepared by extruding the resulting multilamellar vesicles through 200 nm polycarbonate membrane (AMD Manufacturing Inc., Ontario, Canada) at 60° C. under high pressure using nitrogen flow in a sealed stainless steel jacketed extruder (LiposoFast L-50, Avestin, Mannheim, Germany). Liposomal dispersions were diluted 1:10 with PBS and stored in the fridge.

Example 2: Microencapsulation Vesicle Method (MCV)

Liposomes containing gentamicin were prepared in two steps via this method; emulsification, and dispersion with mechanical agitation. The emulsification step was done by dissolving DPPC:DPPE:cholesterol a in molar ratio of 6:0.6:3 in 10 ml dichloromethane, then 5 ml of PBS containing 10 mg/ml gentamicin was added. The mixture was emulsified with a homogenizer (Polytron PT 2500 E, Germany) at 7000 rpm for 10 min resulting in the formation of water in oil emulsion (W/O). The first emulsion was then diluted 1:3 in PBS and mixed at 520 rpm and 30° C. to form water in oil in water emulsion (W/O/W). Stirring was continued until the organic solvent was completely evaporated (60 min). The liposomal dispersion was finally extruded through 200 nm pore size polycarbonate membranes to form liposomes of optimal size.

Example 3: Liposome Loading: Active Loading—Ammonium Sulfate Liposomes (ASL)

In this method, gentamicin was introduced into liposomes by the use of a pH gradient as has been previously described for amphipathic drugs. Since the pKa of gentamicin is 8.2, gentamicin is uncharged when dissolved in basic solutions, allowing it to permeate through lipid membranes, such as those of liposomes. Once the gentamicin is inside the liposomes, it has to be transformed into a charged molecule which will not be able to leave the liposomes. Thus, liposomes are filled with an acidic solution to ensure the transformation of the uncharged gentamicin into a charged compound. Liposomes were prepared as described for LFH liposomes, but the hydration step was done with a 250 mM ammonium sulfate solution (pH 5.3) instead of PBS containing gentamicin. After liposome extrusion, the ammonium sulfate-containing liposomes were centrifuged at 13000 g for 45 min, and then the pelleted liposomes were re-suspended in carbonate buffer (pH 10.2) containing 10 mg/ml of gentamicin in the uncharged state, to facilitate its penetration into liposomes. The liposomes were incubated with gentamicin at 37° C. for 1 h with intermittent vortex mixing every 10 min.

Example 4: Functionalization of Liposomes

A covalent coupling of model or targeting protein to the surface of gentamicin-loaded liposomes was performed. A method has been developed that allows the crosslinking of the protein directly without incorporation of a crosslinking reagent in the final formulation. The employed crosslinking reagent EDC reacts with the surface-exposed carboxyl groups on liposomal DPPE, forming an unstable reactive O-acylsourea ester. NHS is then added in order to increase the stability and the coupling efficiency of EDC. This results in the formation of a semi-stable amine-reactive NHS ester; which can then react with the amine groups on the protein to be coupled resulting in the formation of a stable amide bond. After purification of liposome in order to remove the non-encapsulated gentamicin, gentamicin-loaded liposomes were functionalized using BSA as a model protein, or invasin. Briefly, 2 ml of the liposomal suspension was incubated with the crosslinking reagent solution of EDC and NHS in a molar ratio of (3:1) in an ice bath. For gentle mixing, the suspension was kept shaking (SM, Shaker Germany) for 3 h. Then liposomes were washed three times through Centrisart tubes to remove the excess of the crosslinking. Afterwards, 300 µl of BSA solution or invasin (1 mg/ml) was added to the liposomal suspension and the mixture was then kept in the ice bath overnight with gentle mixing. The degree of protein functionalization was then determined by BCA assay following liposomes purification.

Example 5: Liposome Purification

As a part of the functionalization procedure, and also before analysis of the different liposome content of both non-functionalized and functionalized liposomes, liposomal formulations were separated from any residual, non-incorporated components or other reagents which could affect the chemical characterization. In all cases, the separation process was carried out by centrifugal ultrafiltration using Centrisart tubes (Centrisart 1, Sartorius AG Germany) equipped with a 300 000 molecular weight cut off membrane (MWCO). Briefly, liposomal suspension was placed into a Centrisart tube followed by the filtration membrane, and then centrifuged at 3720 g and 4° C. for 30 min. The ultra-filtrate was then removed and the liposomes were re-suspended in fresh buffer. This procedure was repeated three times to ensure the complete removal of any residual non-liposomal material.

Example 6: Liposome Characterization

Liposomes were prepared by different techniques resulting in liposomes of different physicochemical characteristics. These differences may have an impact on in vitro and in vivo behavior. Therefore, liposomal characterization for the purpose of conducting an evaluation of these different liposome preparation methods was carried out, and can be classified into three categories: physical, chemical and biological characterization. As part of physical characterization, the size distribution and also surface charge of liposomes were evaluated. Chemical characterization of the liposomes included evaluation of various liposomal constituents. The biological characterization focused on the impact of the liposomes in an in vitro cell model.

Example 7: Size and Polydispersity Index

The mean diameter and the polydispersity index (PDI) of liposomes were measured by the dynamic light scattering (DLS) technique using a Zetasizer (Nano ZS Malvern Instruments). This technique is based on the measurement of the intensity of light scattered by the molecules in the sample as a function of time. When light is scattered by a molecule or particle some of the incident light is scattered. If the molecule was stationary then the amount of light scattered would be a constant. Since all molecules in solution diffuse with Brownian motion in relation to the detector there will be interference (constructive or destructive) which causes a change in light intensity. By measuring the time scale of light intensity fluctuations, DLS can provide information regarding the average size, size distribution, and polydispersity of molecules and particles in solution. The zeta potential analysis is applied as a tool for the determining of particle surface charge in solution. This is an important parameter for understanding and predicting the long term stability of particle. Laser-doppler micro-electrophoresis was used to measure the zeta potential of liposomes using a Zetasizer (Nano ZS Malvern Instruments). This measurement is based on the application of an electric field to a solution of molecules or dispersion of particles, resulting in movement of the particles due to the interaction between their surface charge and the applied field. The direction and the velocity of particle motion is a function of particle charge, the suspending medium, and the electric field strength. Particle velocity is then measured using a laser interferometric technique called phase analysis light scattering (M3-PALS), as the particle velocity is proportional to the electrical potential of the particle at the shear plane—that is, the zeta potential. Thus, this optical measurement of the particle motion under an applied field can be used to the determine zeta potential.

Example 8: Liposome Imaging: Scanning Electron Microscopy

Scanning electron microscopy (SEM) is based on the use of a focused beam of high energy electrons in order to generate a variety of signals at the surface of solid specimens. The signals that derive from electron-sample interactions reveal information about the sample including external morphology, chemical composition, and crystalline structure of the materials that make up the sample. In order to characterize the surface morphology of gentamicin-loaded liposomes, SEM imaging was conducted using Zeiss EVO HD15 (Germany) SEM. Briefly, gentamicin-loaded liposomes were washed with water to remove any traces of buffer and then a dilution of 1:20 was carried out in order to avoid the formation of aggregates or any interactions between the particles. A volume of 10 µl was mounted on aluminum stubs, using double-sided adhesive carbon tape and silicon wafers in 5×5 mm chips (TED PELLA, Inc. Canada, USA). After drying, samples were sputter-coated with thick gold film using a Quorum Q150R ES (Gala Instrumente GmbH) sputter-coater, under argon atmosphere for secondary electron emissive SEM and then observed for morphology at an acceleration voltage of 5000 kV. Images were processed with SmartSEM® software.

Example 9: Fluorescence Microscopy

Gentamicin-loaded liposomes functionalized with invasin and containing rhodamine were produced. Rhodamine can emit fluorescence upon an excitation at 560 nm, giving the opportunity to visualize such liposomes using fluorescence microscopy. The preparation of samples for fluorescence imaging was done by linking liposomes to poly-L glutamic acid-coated glass. Briefly, glass bottom dish chambers (3.5× 3.5 cm) were coated with 200 µl of 0.01% poly-L glutamic acid solution in distilled water for 5 min at room temperature. Chambers were washed with distilled water and incubated with 200 µl of 2 mM carbodiimide hydro-chloride (EDC) and 5 mM hydroxysuccinimide (NHS) in MES buffer (pH 6) for 15 min at room temperature to activate the carboxyl groups of poly-L glutamic acid. The non-bound crosslinking reagent EDC/NHS was removed and chambers were washed with MES buffer. Gentamicin-loaded liposomes functionalized with invasin, diluted 1:1, were then placed in the chambers and incubated for 2 h at room temperature in the dark. The crosslinking reaction was stopped using 50 mM TRIS-HCl buffer for 5 min, and then chambers were washed twice with MES buffer. Images were taken using Leica DMI6000B microscope, equipped with a metal halogenide lamp. The objective used was an oil immersion lens 63×, and images were processed using Leica Application Suite Advanced Fluorescence (LAS AF) software.

Example 10: Phospholipid, Cholesterol and Gentamicin Quantification

The Stewart assay, a simple and sensitive colorimetric method for the quantitative determination of phospholipids in liposomes was utilized in this study. This method is based on the ability of phospholipids to form a complex with ammonium ferrothiocyanate. Ferrothiocyanate reagent was prepared by dissolving 27.03 g of ferric 3-chloride-hexahydrate ($FeCl_3.6H_2O$) and 30.4 g of ammonium thiocyanate ($NH_4SCN$) in 1 l of distilled water. A lipid stock solution was prepared by dissolving 10 mg of DPPC in 100 ml chloroform (0.1 mg/ml). Duplicate volumes of this solution between 0.1 and 1 ml were then added to the volume of chloroform required to make the final volume to 2 ml. A 2 ml volume of the ammonium ferrothiocyanate solution was then added to each, in order to create a range of standard solutions in duplicate. Tubes of standard solutions were then vigorously vortexed for 20 sec and centrifuged for 10 min at 130 g (Rotina Centrifuge 420). A standard curve was constructed by measuring the optical density of the lower layer consisting of phospholipids and chloroform at 485 nm using a spectrophotometer (Lambda 35 UV/VIS Spectrophotometer, Perkin Elmer). The same procedure was used to determine the amount of phospholipids in liposomes by mixing 0.1 ml of liposomes with 1.9 ml of chloroform and 2 ml of the ferrothiocyanate reagent. The obtained absorbance was applied in the calibration equation to calculate the phospholipids concentration in liposomes. High performance liquid chromatography (HPLC) method for cholesterol quantification was used, with some modifications. Briefly, the Dionex HPLC system was used (Thermo Scientific, Germany) composed of a P680 pump, an Elite degassing System, an Asta-medica AG 80 column oven and a UV detector. The analytical column used was a LiChrospher® 100, RP-18 (5 µm), 125×4 column (Merck KGaA, Darmstadt, Germany). The oven temperature was set at 30° C. A mobile phase of acetonitrile: methanol (70:30 v/v) with a flow rate of 2 ml/min was used, with an analysis time of 15 min and an injection volume of 100 µl. All samples were analyzed in triplicate. Cholesterol was detected at a wavelength of 210 nm. Identification of the cholesterol peak in HPLC chromatograms was done by comparison of the retention times of the sample peak with those of the standards. Quantification of cholesterol in liposomes was done by comparison of sample peak area under the curve (AUC) with AUC values of standards. The standard curve was constructed using 7 standard concentrations, prepared using a stock solution of 200 µg/ml of cholesterol in 50:50 vol/vol of acetonitrile: methanol/ethylacetate (1:1), which was diluted in order to produce concentrations varying from 0 to 200 µg/ml cholesterol. For liposomes, a 400 µl volume of liposome formulation was mixed with 1 ml of 50:50 vol/vol acetonitrile: methanol/ethylacetate (1:1). A fluorometric procedure was used for gentamicin quantification. This method is based on the reaction of primary amine groups of gentamicin with the utilized reagent, O-phthaldialdehyde (OPA). Under basic pH conditions, this reaction produces a fluorescence which has a linear relationship with the gentamicin concentration, and which can be read directly on a simple fluorimeter (Tecan, Infinite M200, Germany) at an excitation wavelength of 344 nm and an emission wavelength of 450 nm. The preparation of the OPA reagent was performed by dissolving 0.2 g of OPA in 1 ml methanol and then adding 19 ml of boric acid (0.4 M, pH 10.4). The mixture was then stirred and 0.4 ml of 2-mercaptoethanol (14.3 M) was added. The pH was then re-adjusted to 10.4 using potassium hydroxide. Both boric acid and 2-mercaptoethanol were used in order to achieve high reaction efficiency and to stabilize the fluorescent product. Standards were prepared using 1 ml of gentamicin solution ranging in concentration from 0 to 30 µg/ml in PBS (pH 7.4). 0.6 ml of methanol was then mixed with each standard followed by the addition of 0.9 ml of the reagent solution (0.1 ml OPA reagent and 0.8 ml methanol). Quantification of the gentamicin in liposomes first required an extraction of the lipids due to their interference with this method. The extraction was done by adding 250 µl of dichloromethane to 200 µl of washed liposomal dispersion, followed by 500 µl of methanol. The mixture was then vigorously mixed until a clear solution was obtained. Afterwards 250 µl of NaOH solution (0.2 M) followed by 250 µl of dichloromethane were added to the mixture and mixed again. The resulting biphasic system was then centrifuged at 3720 g for 5 minutes, and 480 µl of the remaining upper layer was used for gentamicin quantification. This extracted 480 µl was made to a volume of 1 ml by adding PBS; 0.6 ml of methanol was then added, followed by 0.9 ml of the reagent solution (0.1 ml OPA reagent and 0.8 ml methanol). Standards and samples were then incubated for 10 min in dark, following which the fluorescence was measured in a plate reader with an excitation of 344 nm and emission of 450 nm. The amount of gentamicin entrapped within liposomes was then calculated by comparing the measured fluorescence of samples to that of standard solutions. The entrapped amount of gentamicin was then expressed as an Encapsulation Efficiency, in which the amount of entrapped gentamicin is given as a percentage of the initial amount of gentamicin added during liposome preparation (Equation 1). Using the measured amounts of gentamicin and the measured amounts of lipid components (actual loading) as well as the initial amounts of gentamicin and lipid components (initial loading), the Loading Efficiency of liposomes was also calculated (Equation 2):

Equation 1. Encapsulation efficiency.

$$\text{Encapsulation Efficiency \%} = \frac{\text{Actual amount of Gentamicin}}{\text{Initial amount of Gentamicin}} \times 100$$

Equation 2. Loading efficiency.

$$\text{Loading Efficiency \%} = \frac{\text{Actual Loading}^*}{\text{Initial Loading}^{**}} \times 100$$

$^*\text{Actual Loading} =$ $$\frac{\text{Actual amount of Gentamicin (µmol/100 µl)}}{\text{Actual amount of }(Phosph + Chol)\text{ (µmol/100 µl)}}$$

$^{**}\text{Initial Loading} = \frac{\text{Initial amount of Gentamicin (µmol/100 µl)}}{\text{Initial amount of }(Phosph + Chol)\text{ (µmol/100 µl)}}$ Example 11: Protein Quantification—BCA Assay The amount of protein attached to the liposomes was quantified using the bicinchoninic acid protein assay (BCA). The BCA assay combines a protein-induced biuret reaction with the highly sensitive and selective colorimetric detection of the resulting cuprous cation ($Cu^{1+}$) by bicinchoninic acid. A $Cu^{2+}$ protein complex is formed under alkaline conditions, followed by reduction of the $Cu^{2+}$ to $Cu^{1+}$. A purple-colored reaction product is formed by chelation of two molecules of bicinchoninic acid with one cuprous ion. The bicinchoninic acid-copper complex is water soluble and exhibits a linear absorbance at 562 nm over a board range of protein concentrations. This absorbance is proportional to the protein concentration. Standard curves were prepared in accordance with the utilized BCA assay kit (Quantipro BCA Assay Kit, Sigma-Aldrich). Standards were made using different concentrations from stock solutions of either invasin or BSA (50 µg/ml). The Quantipro Working Reagent was prepared by mixing 25 parts of Reagent QA (Solution of sodium carbonate, sodium tartrate, and sodium bicarbonate in 0.2 NaOH, pH 11.25) with 25 parts of Reagent QB (Solution of bicinchoninic acid 4% w/v, pH 8.5). After Reagents QA and QB were combined, 1 part of Reagent QC (4% w/v cupric sulfate and pentahydrate solution) was added and mixed until a homogenous green color was obtained. In glass tubes, 1 ml of the standards was mixed with 1 ml of the Quantipro Working Reagent. Mixtures were incubated at 60° C. for 1 hour. The UV absorbance was recorded in 96-well plates in a plate reader at 562 nm. As in the case of standards, 1 ml of liposome samples in glass tubes was combined with 1 ml of Quantipro working Reagent, and the UV absorbance measured at 562 nm. The concentration of liposome-bound protein was then calculated in reference to the created standard curve. Sodium dodecyl sulfate polyacrylamide gel electrophoresis (SDS-PAGE) was performed in order to confirm the results of the protein quantification by BCA assay. After loading protein-functionalized liposome samples, protein standards and a protein ladder (Thermo Scientific™ Spectra™ Multicolor Broad Range Protein Ladder), electrophoresis was carried out in electrode running buffer at 30 mA constant voltage for 45 min. The gel was washed and stained with Page Blue Protein Staining Solution (Fermentas, Lithuania). Images from the gel were taken by Gel Doc™ EZ Imager (Bio-Rad, Germany) and processed with Image Lab Software (Bio-Rad, Germany).

Example 12: Stability and Release Studies

Liposomes were stored at 4° C. for a period of 45 days, and at set time intervals samples were taken and analyzed in terms of size, PDI, zeta potential, as well as gentamicin and invasin content. In vitro release of gentamicin from the liposomes was investigated over a period of 3 h. Dialysis cellulose-ester membranes of 11.5 mm diameter and 10.000 MWCO (Biotech, USA) were soaked for 1 h before use in distilled water at room temperature to remove the preservative, followed by rinsing thoroughly in distilled water. Dialysis membranes containing 5 ml of gentamicin-loaded liposomes, invasin-functionalized, gentamicin-loaded liposomes or gentamicin solution were kept stirring at 200 rpm in separate beakers containing 60 ml of PBS (pH 7.4) and incubated at 37° C. (Binder Incubator, Germany) for 3 h. At predetermined time intervals, 1 ml aliquots of PBS solution were removed and substituted with an equal volume of fresh PBS. The amount of gentamicin in removed PBS aliquots was then quantified.

Example 13: Biological Characterization

Human Larynx Carcinoma cell line (HEp-2) cells were cultured in a 75 cm² flask using Roswell Park Memorial Institute (RPMI 1640) medium, supplemented with 7.5% newborn calf serum (NCS). Cells were incubated in a humidified incubator (Heraeus $CO_2$ Thermo Scientific Incubator) at 37° C. and 5% $CO_2$. Medium was changed every two days and cells were split when confluency was reached. For cellular invasion experiments, cells grown in 75 cm² flasks were washed with PBS (PBS Dulbecco, Biochrom Germany) and incubated with 3 ml of trypsin 0.5 g/l for 10 min to detach the cells. Afterwards, 7 ml RPMI medium supplemented with 7.5% NCS was added to the flask to inhibit the trypsin activity. Cells were then plated in 24 well plates at a density of 1×10⁵ cells per well and incubated in a humidified incubator at 37° C. and 5% $CO_2$ for 18 h to allow cells to adhere to the plate. HEp-2 cells infected with the pathogens Salmonella enterica serovar Typhimurium SL1344 and Yersinia pseudotuberculosis YPIII were used as an in vitro model to test the invasive ability and resulting efficacy of gentamicin-loaded liposomes. Bacteria were cultured 24 h prior to experiments in overnight tubes containing 5 ml of Lennox broth (LB) medium (Carl Roth GmbH, Germany). Tubes were kept overnight in a shaking incubator (Infors HT, Multitron) at 37° C. in the case of Salmonella enterica, and 25° C. for Yersinia pseudotuberculosis. Prior to invasion experiments, Salmonella enterica was freshly diluted 1:100 with LB medium and incubated at 37° C. for a further 3 h growing to late exponential phase in order to induce expression of pathogenicity island I (SPI1) proteins important for cell invasion. Afterwards, both bacteria were washed once and suspended in PBS (PBS tablets. Medicago, Sweden). The culture medium of HEp-2 cells (seeded one day before in a 24 well-plate) was then exchanged with binding buffer (RPMI 1640 medium with 20 mM Hydroxyethyl-piperazineethane-sulfonic acid buffer (HEPES) and 0.4% BSA) containing Salmonella enterica or Yersinia pseudotuberculosis at ratios of 1/10 and 1/25 Multiplicity of Infection (MOI); which is the ratio of infection targets to infectious agents (cell/bacteria). 24 well plates were then centrifuged at 1000 rpm for 5 min (Eppendorf 5810 R Centrifuge) to sediment the bacteria onto the cells. Cells and bacteria were then incubated for 1 h in a humidified incubator at 37° C. and 5% $CO_2$ atmosphere to allow binding and penetration of the bacteria into the cells. Cells were then washed twice with PBS and incubated for 1 h or 2 h with binding buffer containing 50 μg/ml of gentamicin (Sigma-Aldrich, Germany) to kill any extracellular located bacteria. The infected cells were then washed twice with PBS to eliminate the extracellular gentamicin and killed extracellular bacteria, leaving HEp-2 cells containing either intracellular Salmonella or intracellular Yersinia. Following the invasion protocol as above, infected cells were washed twice with PBS and lysed with 200 μl lysis buffer containing 0.1% Triton X-100. Cell lysate was then plated in sterile agar plates (2% LB and 1.8% agar) in serial dilutions (maximum dilution 1:625) and incubated overnight at 37° C. for Salmonella enterica and for 48 h at 25° C. for Yersinia pseudotuberculosis. Following incubation, bacterial colonies were counted and multiplied by the appropriate dilution factor. The number of colonies from the cell lysate was then expressed as a percentage of the number of colonies from the initial amount of bacteria used for the infection (inoculum), referred to as the percentage of invasion (Equation 3). The conditions (namely, cell: bacteria ratio) which were shown to result in the highest percentage of invasion were selected for use in further studies employing liposome treatment of infected cells:

Equation 3. Percentage of Invasion $$\% \text{ of Invasion} = \frac{N^{br} \text{ of colonies from cell lysate}}{N^{br} \text{ of colonies from inoculum}} \times 100$$

Infected cells were incubated with empty liposomes, invasin-functionalized empty liposomes, liposomes containing 50 μg/ml gentamicin and liposomes containing 50 μg/ml gentamicin functionalized with invasin, all of which were suspended in binding buffer. Cells containing intracellular Salmonella enterica were treated with liposome formulations for 1 h, while cells containing Yersinia pseudotuberculosis were treated with liposomes for either 1 h or 2 h. The analysis of liposomal treatment was carried out by calculating the percentage of invasion from each treatment condition according to (Equation 3). Then, the efficiency of treatment was assessed by measuring the percentage of decrease in invasion after normalizing the different treatments to the blank (un-treated).

Example 14: Overexpression and Purification of the Cell-Surface Exposed C-Terminal Domain of Invasin (InvA497) from *Y. pseudotuberculosis*

Two liters of *E. coli* BL21 expressing the His-tagged. C-terminal 497 amino acids of invasin ($His_6$-Inv497) from *Yersinia pseudotuberculosis* were grown at 37° C. in Luria Bertani broth medium to an $A_{600}$=0.4. The culture was shifted to 17° C. and grown to an $A_{6oo}$=0.6. Isopropyl-β-D-thiogalactopyranoside was added to a final concentration of 100 μM to induce the expression $His_6$-InvA497. The cells were grown overnight at 17° C. The cell pellet was resuspended in 50 ml cold lysis buffer containing 50 mM $NaH_2PO_4$, 300 mM NaCl, 10 mM imidazole (pH 8) plus protease inhibitor cocktail containing 5 mM phenylmethylsulfonyl fluoride, 10 mM pepstatin (Sigma, Steinheirn, Germany), 10 mM E64 protease inhibitor (Boehringer, Mannheim, Germany), 20 mM leupeptin (US Biochemical, Cleveland, Ohio, USA) and 10 mM chymostatin (Sigma, Steinheim, Germany). The cells were disrupted using a french press (2× at 1000 psi). The $His_6$-InvA497 protein was purified by affinity chromatography with Ni-NTA Agarose (Qiagen), eluted in elution buffer containing 50 mM $NaH_2PO_4$, 300 mM NaCl, 250 mM imidazol (pH 8) and dialyzed twice against 10 mM Tris buffer pH 8 containing 300 mM NaCl. Protein concentrations were determined by the Bradford protein assay (Pierce, Rockford, Ill., USA).

Example 15: Covalent Attachment of InvA497 on the Liposomal Surface

Invasin conjugation to the liposomal surface was based on covalent immobilization of the N-terminal of the protein to the carboxylic groups on the liposomal surface which were first activated using EDC/NHS (EDC: N-(3-dimethylaminopropyl)-N'-ethylcarbodiimide hydrochloride (Sigma Aldrich, Steinheim, Germany; NHS: N-hydroxysuccinimide, 99% (Carbolution Chemical GmbH, Saarbrücken, Germany). A volume of 300 μl of 48 mM EDC/19 mM NHS in 100 mM MES buffer (pH 6) was incubated overnight with a 2 ml liposomal dispersion with shaking at room temperature, centrifuged (Rotina 420R; Hettich Zentrifugen, Tuttlingen, Germany) in Centrisart® tubes 300,000 MWCO (Sartorius, Goettingen, Germany) at 3270 g, 4° C. for 30 min to remove excess free reagent followed by three successive washing steps during which the MES buffer was gradually exchanged with PBS, pH 7.4. The volume was then completed to 2.5 ml with PBS. 300 μl of 1 mg/ml invasin in PBS was added and coating process was continued overnight in ice bath with shaking. This was followed by centrifugation and washing steps in Centrisart® tubes 300,000 MWCO to remove unbound invasin. Covalent attachment of BSA (Sigma Aldrich, Steinheim, Germany) on liposomes followed the same protocol and served as controls for cell adhesion experiments.

Example 16: Cell Cultures and Treatments

HEp-2 cells (CCL-23™; ATCC, Manassas, Va., USA) were cultivated in RPMI (Gibco by life Technologies™, Paisley, UK) supplemented with 10% fetal calf serum (FCS) (Lonza, Cologne, Germany) and kept in culture for 2 months maximum after thawing. Caco-2 cells, clone C2Bbel (CRL-2102™; ATCC, Manassas, Va., USA) were cultivated in Dulbecco's modified Eagle's medium (DMEM) supplemented with 10% FCS and 1% non-essential amino acids (PAA cell culture company, Pasching, Austria) and used at passages 58-72.

Example 17: Cell Viability Assay: ATP (Vialight® Plus) Assay

This assay kit (Lonza) measures cytoplasmic adenosine triphosphate (ATP) to assess the functional integrity of living cells. This bioluminescent assay utilizes the enzyme luciferase to catalyze the formation of light from ATP and luciferin. The emitted light intensity is linearly related to ATP concentration. A volume of 100 μl of a series of 0.12-1.92 μM liposomal dispersions was tested on confluent HEp-2 cells, and confluent and 50% confluent Caco-2 cells seeded in 96-well plates (Greiner Bio One, Frickenhausen, Germany). Invasin-coated and uncoated liposomes were tested in parallel. Cells were incubated with the liposomes for 4-8h 50 μl/well of cell lysis reagent was added to extract ATP from the cells. A volume of 100 μl of each of the cell lysate and ATP monitoring reagent Plus8 were incubated in 96-well white walled luminometer plate (Optiplate™-96; Perkin Elmer Inc., Waltham, Mass., USA) for 2 min at room temperature in the dark. Bioluminescence was measured (Tecan Deutschland GmbH, Crailsheim, Germany). Cells grown in culture medium only were considered as high control (100% cell viability) and others incubated with Triton X-100 (2% w/v) were used as low control (0% cell viability). Percentage cell viability was calculated based on five replicates as follows:

$$\%\ \text{Cell viability} = \frac{Lum_{exp} - Lum_{low\ control}}{Lum_{high\ control} - Lum_{low\ control}} * 100$$

In parallel, ATP controls in concentrations of 1.5 and 0.015 μM were prepared. 50 μl of each of the control and the liposomes was incubated together with 100 μl ATP monitoring reagent Plus® and bioluminescence was measured to check for wavelength interference in absence of cells.

Example 18: Cell Adhesion Experiments

One day before adhesion experiments, HEp-2 cells were seeded in 8 well μ-slides (ibidi cell infocus, Martinsried, Germany) at a density of $1\times10^4$ cells/well. In parallel, constitutively GFP-expressing *Yersinia pseudotuberculosis* were grown in LB broth prior to infection. Two types of liposomes at a concentration of $4\times10^4$ liposomes/ml were tested: liposomes to which invasin was covalently coupled (invas-cov) versus liposomes to which invasin was physically adsorbed by incubation of the liposomes with 1 mg/ml invasin at 37° C. for 2 h (invasphys). For control liposomes BSA was covalently attached (BSA-cov) or physically adsorbed (BSA-phys). Three sets of experiments were performed in parallel: The first set resembles late infection stage where cells were infected with bacteria (50 μl of $1\times10^6$ bacteria per well) 30 min before addition of 50 μl/well of test liposomal dispersion. In the second set, resembling early infection stage, both bacteria and liposomes were applied together. For the third set (control), the liposomes were applied to cells without any pretreatment; i.e. representing the healthy state. Cells were washed three times with PBS and incubated in binding buffer (RPMI 1640 medium supplemented with 20 mM HEPES (pH 7) and 0.4% BSA) before addition of bacteria and liposomes. Cells were incubated for 1 h after liposomal application, after which the medium was removed and cells were washed three times with PBS. This was followed by cell fixation using 4% paraformaldehyde in PBS for 10 min, blocking and cell permeabilization with blocking buffer (5% goat serum, 0.1% Triton X-100 in 1×PBS) for 60 min and nuclei staining by DAPI mounting medium (Roth, Karlsruhe, Germany). Cell adhesion was examined using fluorescence microscopy (Zeiss Axioskope; Zeiss, Jena, Germany) followed by image analysis by ImageJ (http://rsbweb.nih.gov/ij/). Image analysis was based on a previously established method in which the number of pixels due to liposomal fluorescence was calculated. The number of liposomes was estimated based on the area of a single diffraction-limited fluorescent spot; $\pi(r_{xy})^2$, 0.359 $\mu m^2$ in this study based on $\lambda$ (emission wavelength for rhodamine)=564 nm and NA (numerical aperture of the optical lens)=1.1.

Example 19: Cell Uptake Assays

Cells were seeded in 24-well imaging plates (Zell-Kontakt, Nörten-Hardenberg, Germany) to 70-80% confluency for HEp-2 cells and 50%-90% confluency for Caco-2 cells. Liposomes, at a concentration of 1.92 μM, were used for cell uptake experiments. Liposomes were first centrifuged at 20000 g, at 4° C. for 30 min and redispersed in biological medium. Cells were washed with PBS after removing the biological medium and liposomes (500 ul/well) were incubated with the cells for 1, 4 or 5 h. In order to assess the uptake mechanism of invasin-coated liposomes (invas-cov) into HEp-2 cells, experiments were conducted at 37° C. or 4° C. for 4 h. In addition, the following inhibitors in RPMI supplemented with 20 mM HEPES buffer (pH 7) and 0.4% BSA were incubated with the cells for 1 h at 37° C.: anti-integrin $\beta_1$-antibody, 1:100 dilution (clone P4C10; Sigma Aldrich, Schnelldorf, Germany), 1 μM NPC-15437 dihydrochloride (Sigma Aldrich, Schnelldorf, Germany) and 25 μM Akt inhibitor VIII (Calbiochem; EMD Chemicals Inc., San Diego, Calif., USA). At the end of 1 h incubation, inhibitors were removed and cells were washed with PBS before incubation for further 4 h with liposomes. At the end, the biological media were removed and the cells were washed with PBS. Cell membrane was stained by 6.25 μg/ml fluorescein wheat germ agglutinin (Flu-WGA) (Vector Laboratories, Inc., Burlingame, Calif., USA). Cells were fixed with 4% formaldehyde. Nuclei were stained with DAPI (6.66 ng/ml) (Sigma Aldrich, Schnelldorf, Germany). Plates were protected from light and stored at 4° C. till further imaging. At least three replicates were performed. Uncoated liposomes were used as a control.

Example 20: Confocal-Multiphoton Laser Scanning Microscopy and Image Analysis Fluorescence imaging was performed using an inverted confocal/two photon microscope (ZEISS LSM 510 MTA, Carl Zeiss, Jena, Germany). The objective used was a water immersion lens 40+ (NA=1.1). Wavelengths of 543 nm, 488 nm and 720 nm were used for excitation of rhodamine-labelled liposomes, fluorescein-labeled cell membrane and DAPI-labeled nuclei, respectively. Z-stacks of the skin samples were taken with steps every 0.8 μm. Each optical scan is of a size of 0.22 μM×0.22 μM. The gain settings were adjusted for each measurement individually. For each captured z-stack optical layers encompassing only taken up liposomes were chosen and z-projection image of the red channel (red fluorescence due to liposomes) was developed using ImageJ. Number of pixels was computed and converted into weighed number of liposomes as described earlier.

Example 21: Live Cell-Imaging

HEp-2 cells were seeded in 8-well μ-slide chambers and used when 70-80% confluent. Liposomes were first redispersed in biological medium and sterilized upon filtration through 0.2 μm membrane filter. Cells were washed with the biological medium, stained with Flu-WGA for 5 min at 37° C. and washed again before application of liposomes. The whole setup was transferred into a special incubation chamber of the confocal microscope with a constant temperature of 37° C. and 5% $CO_2$ to maintain cell viability throughout the experiment. An area of interest was selected and imaging using the same optical settings was performed as indicated above, except for the size of the optical image; 0.27×0.27 $\mu m^2$. Z-stack was sequestered at different time intervals (1, 2, 3 and 4 h). The thickness of the optical layer was kept as 0.8 μm. ImageJ was then used to develop a z-projection image of the red channel of the optical layers in the sequestered z-stack followed by pixel analysis. The weighted number of liposomes was plotted versus time to determine cell-uptake kinetics of invasin-coated (invascov) versus uncoated liposomes. To get more information on the first hour kinetics, cell uptake experiments at 10 and 30 min for both liposomes were conducted in parallel using the same set-up, however the cells were fixed afterward and imaged similarly.

The invention claimed is:

1. A carrier system, comprising
   (i) a carrier,
   (ii) a pathogen entry protein or fragment thereof, which specifically binds to a molecule on the surface of a mammalian target cell of said pathogen and which is covalently linked to the surface of said carrier, and
   (iii) at least one hydrophilic antipathogenic agent,
   wherein the pathogen entry protein specifically binds to the extracellular domain of $\beta_1$-integrin receptor, and the pathogen entry protein is not SEQ ID NO:6.

2. The carrier system according to claim 1, wherein said carrier is selected from the group consisting of nanoparticles, preferably matrices of solid-lipid nanoparticles (SLN); polymer particles, preferably nanocapsules; vesicles, preferably liposomes and other artificially-prepared spherical or non— spherical vesicles.

3. The carrier system according to claim 2, wherein the liposome is unilamellar or multilamellar and/or the overall charge of the liposome is positive, neutral or negative.

4. The carrier system according to claim 1, wherein the molecule on the surface of a mammalian target cell is a receptor protein, preferably a $\beta_1$-integrin receptor.

5. The carrier system according to claim 1 wherein the pathogen entry protein is from a bacterium that sequesters in a non-phagocytic cell.

6. The carrier system according to claim 5, wherein the bacterium is a Gram-negative bacterium, preferably *Chlamydia, Coxiella burnetii, Ehrlichia, Rickettsia, Legionella, Salmonella, Shigella*, or *Yersinia*; or a Gram-positive bacterium, preferably *Mycobacterium leprae*, or *Mycobacterium tuberculosis*, more preferably *Yersinia*.

7. The carrier system according to claim 5, wherein the pathogen entry protein is selected from the group consisting of invasin, *Yersinia* adhesin A (YadA), internalin and other inv-type and related adhesive bacterial outer membrane molecules.

8. The carrier system according to claim 1, wherein the covalent link between the carrier and the pathogen entry protein is direct or via a linker.

9. The carrier system according to claim 1, wherein the pathogen entry protein is linked via its C-terminus, its N-terminus or a side chain of an amino acid of said pathogen entry protein, preferably its N-terminus.

10. The carrier system according to claim 7, wherein the invasin has an amino acid sequence selected from the group consisting of SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9 or variants thereof with at least 70% amino acid sequence identity and which specifically bind to the extracellular domain of $\beta_1$-integrin receptor.

11. The carrier system according to claim 1, wherein the fragment of the pathogen entry protein consists or essentially consists of the extracellular domain of pathogen entry protein.

12. The carrier system according to claim 11, wherein the hydrophilic antipathogenic agent is selected from the group consisting of small molecules; proteins; nucleic acids, preferably siRNA; nucleotides, preferably polynucleotides.

13. The carrier system according to claim 12, wherein the hydrophilic antipathogenic agent is an antibiotic or cytostatic.

14. The carrier according to claim 13, wherein
   (i) the antibiotic is selected from the group consisting of polypeptides, glycopeptides, aminoglycosides, lipopeptides, quinolones or β-lactam antibiotics and organic or anorganic salts thereof, (ii) the cytostatic is selected from the group consisting of alkylating substances, anti-metabolites, epothilones, nuclear receptor agonists and antagonists, anti-androgens, anti-estrogens, platinum compounds, hormones and antihormones, interferons and inhibitors of cell cycle-dependent protein kinases (CDKs), inhibitors of cyclooxygenases and/or lipoxygenases, biogenic fatty acids and fatty acid derivatives, including prostanoids and leukotrienes, inhibitors of protein kinases, inhibitors of protein phosphatases, inhibitors of lipid kinases, platinum coordination complexes, ethyleneamines, methylmelamines, trazines, vinca alkaloids, pyrimidine analogs, purine analogs, alkylsulfonates, folic acid analogs, anthracendiones, substituted urea, methylhydrazine derivatives, in particular acediasulfone, aclarubicine, ambazone, aminoglutethimide, L-asparaginase, azathioprine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin, dapsone, daunorubicin, dibrompropamidine, diethylstilbestrol, docetaxel, doxorubicin, enediynes, epirubicin, epothilone B, epothilone D, estramucin phosphate, estrogen, ethinylestradiol, etoposide, flavopiridol, floxuridine, fludarabine, fluorouracil, fluoxymesterone, flutamide, fosfestrol, furazolidone, gemcitabine, gonadotropin releasing hormone analog, hexamethylmelamine, hydroxycarbamide, hydroxymethylnitrofurantoin, hydroxyprogesteronecaproate, hydroxyurea, idarubicin, idoxuridine, ifosfamide, interferon α, irinotecan, leuprolide, lomustine, lurtotecan, mafenide sulfate olamide, mechlorethamine, medroxyprogesterone acetate, megastrol acetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, oleomucin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, scriflavinium chloride, semustine, streptozocin, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, tenipo side, tertipo side, testolactone, testosterone propionate, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin and organic or anorganic salts thereof.

15. A carrier system according to claim 1, wherein the hydrophilic antipathogenic agent exhibits a variable release kinetic from the carrier system.

16. A pharmaceutical composition comprising a carrier system according to claim 1 and a pharmaceutical acceptable excipient.

17. A pharmaceutical composition according to claim 16, wherein the carrier system is released from the pharmaceutical composition with a variable release kinetic.

18. A pharmaceutical according to claim 17, wherein the release kinetic is selected from the group of rapid release kinetics, sustained release kinetics or delayed release kinetics.

19. A method of manufacturing a carrier system according to claim 1, comprising the step of covalently linking the pathogen entry protein or part thereof to the carrier either prior or after contacting the carrier with at least one hydrophilic antipathogenic agent.

20. The method of claim 19, wherein the pathogen entry protein and/or at least one constituent of the carrier comprises an activatable group prior to covalent linking.

21. The method of claim 20, wherein the activatable group is activated with an activating reagent selected from the group consisting of carbodiimides, preferably N,N'-diisopropylcarbodiimide (DIC), N,N'-dicyclohexylcarbodiimide (DCC), more preferably N-(3-Dimethylaminopropyl)-N'-ethylcarbodiimide hydrochloride (EDC); succinimidylesters, preferably sulfosuccinimide, N-hydroxybenzotriazole, more preferably N-hydroxysuccinimid (NHS); triazine-based coupling reagents, preferably 4-(4,6-Dimethoxy-1,3,5-triazin-2-yl)-4-methylmorpholiniumchloride (DMTMM); maleidesters; and glutaraldehyde.

22. The method of claim 21, wherein the activating reagent is a mixture of N-(3-dimethylaminopropyl)-N'-ethylcarbodiimide hydrochloride (EDC) and N-hydroxysuccinimide (NHS), preferably EDC in a concentration of 5-100 mM, preferably 48 mM and NHS in a molar concentration range of 1-50 mM, preferably 19 mM.

23. Carrier system according to claim 1 for use as medicament.

24. Carrier system according to claim 1 for the treatment or prophylaxis of infectious diseases, preferably systemic infection.

25. Carrier system according to claim 24, wherein the infectious disease is an infection with a bacterium that sequesters in a non-phagocytic cells, preferably a Gram-negative bacterium, more preferably *Chlamydia, Coxiella burnetii, Ehrlichia, Rickettsia, Legionella, Salmonella, Shigella*, or *Yersinia*; or Gram-positive bacterium, more preferably *Mycobacterium leprae*, or *Mycobacterium tuberculosis*.

26. The carrier system according to claim 1, wherein the pathogen entry protein is YadA, preferably having SEQ ID NO: 8 or SEQ ID NO: 9, or a variant thereof with at least 70% amino acid sequence identity and which specifically binds to the extracellular domain of $\beta_1$-integrin receptor.

27. The carrier system according to claim 1, wherein the pathogen entry protein comprises an amino acid sequence consisting of amino acids 191 to 289 of SEQ ID NO:2.

* * * * *